US009040248B2

(12) United States Patent
Hager et al.

(10) Patent No.: US 9,040,248 B2
(45) Date of Patent: May 26, 2015

(54) KITS FOR DETECTING AND MONITORING ENDOCRINE DISRUPTING CHEMICALS (EDCS)

(71) Applicant: The United States of America, as represented by the Secretary, Department of Health and Human Services, Washington, DC (US)

(72) Inventors: Gordon L. Hager, Garrett Park, MD (US); Diana A. Stavreva, Arlington, VA (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 13/912,071

(22) Filed: Jun. 6, 2013

(65) Prior Publication Data

US 2013/0330741 A1 Dec. 12, 2013

Related U.S. Application Data

(60) Provisional application No. 61/656,473, filed on Jun. 6, 2012.

(51) Int. Cl.

| | |
|---|---|
| ***G01N 33/53*** | (2006.01) |
| ***G01N 21/64*** | (2006.01) |
| ***G01N 33/50*** | (2006.01) |

(52) U.S. Cl.

CPC ........ *G01N 21/6486* (2013.01); *G01N 33/5014* (2013.01); *G01N 33/5035* (2013.01); *G01N 2520/00* (2013.01)

(58) Field of Classification Search

None

See application file for complete search history.

(56) References Cited

U.S. PATENT DOCUMENTS

| | | | |
|---|---|---|---|
| 6,455,300 | B1 | 9/2002 | Htun et al. |
| 7,312,032 | B2 | 12/2007 | Htun et al. |
| 8,058,395 | B2 | 11/2011 | Htun et al. |
| 2003/0077645 | A1 | 4/2003 | Hager et al. |
| 2004/0147030 | A1 | 7/2004 | Nebert et al. |
| 2009/0181372 | A1 | 7/2009 | Htun et al. |

FOREIGN PATENT DOCUMENTS

| | | | |
|---|---|---|---|
| JP | 2003 329683 | | 11/2003 |
| JP | 3768916 | B9 | 4/2006 |
| WO | WO 97/20931 | | 6/1997 |
| WO | WO 03/027639 | A2 | 4/2003 |

OTHER PUBLICATIONS

Stavreva, et al., "Prevalent Glucocorticoid and Androgen Activity in US Water Sources," *Sci Rep.*, 2:937, doi: 10.1038/srep00937, Dec. 6, 2012 (8 pages).

Alvarez et al., "Reproductive health of bass in the Potomac, USA, drainage: Part 2. Seasonal occurrence of persistent and emerging organic contaminants," *Environ. Toxicol. Chem.* 28:1084-1095, 2009.

Balsiger et al., "A Four-Hour Yeast Bioassay for the Direct Measure of Estrogenic Activity in Wastewater without Sample Extraction, Concentration, or Sterilization," *Sci Total Environ.* 408(6):1422-1429, 2010.

Barnes et al., "Water-Quality Data for Pharmaceuticals, Hormones, and Other Organic Wastewater Contaminants in U.S. Streams, 1999-2000," *USGS* Open-File Report 02-94, 6 pages, 2002.

Buxton et al., "Pharmaceuticals, Hormones, and Other Organic Wastewater Contaminants in U.S. Streams," *USGS* Fact Sheet FS-027-02, 2 pages, 2002.

Chang et al., "Occurrence of Natural and Synthetic Glucocorticoids in Sewage Treatment Plants and Receiving River Waters," *Environ. Sci. Technol.* 41:3462-3468, 2007.

Chang et al., "Determination and source apportionment of five classes of steroid hormones in urban rivers," *Environ. Sci. Technol.* 43:7691-7698, 2009.

Chu et al., "Validation of a new yeast-based reporter assay consisting of human estrogen receptors alpha/beta and coactivator SRC-1: application for detection of estrogenic activity in environmental samples," *Environ Toxicol.* 24(5):513-521, 2009.

Chung, "Development of a Novel Ligand Binding Assay for Estrogen Receptor," *U.S. Army Medical Research and Materiel Command*, Fort Detrick, Maryland 21702-5012, Report Award Number: DAMD17-99-1-9068, 7 pages, Apr. 2002.

Ciparis et al., "Effects of watershed densities of animal feeding operations on nutrient concentrations and estrogenic activity in agricultural streams," *Sci. Total Environ.* 414:268-276, 2012.

Dixon et al., "The nuclear translocation assay for intracellular protein-protein interactions and is application to the Bcr coiled-coil domain," *Biotech.* 49(1);519-524, 2010.

Elbi et al., "Molecular chaperones function as steroid receptor nuclear mobility factors," *Proc Natl Acad Sci USA* 101(9):2876-2881, 2004.

Garcia-Reyero et al., "Monitoring of endocrine disruptors in surface waters by the yeast recombinant assay," *Environ. Chem.* 20(6):1152-1158, 2001.

Griekspoor et al., "Visualizing the action of steroid hormone receptors in living cells," *Nucl. Recept. Signal.* 5, e003, 2007 (9 pages).

(Continued)

*Primary Examiner* — Michael Pak

(74) *Attorney, Agent, or Firm* — Klarquist Sparkman, LLP

(57) ABSTRACT

Described herein are compositions, a system, and kits for detection of endocrine disruptor chemicals (EDCs) in environmental samples, such as samples of water including but not limited to waste water treatment plant effluent, using a live-cell fluorescence-based nuclear translocation reporter system. Upon binding of a ligand to a fluorescent-labeled reporter protein, the protein (and therefore the fluorescence) is translocated in a ligand level-dependent manner from the cytoplasm to the nucleus of live mammalian cells; this translocation is detectable as diffuse (cytoplasmic) fluorescence converting to localized, brightly fluorescent nuclei. The described kits can be used to reliably detect very low levels of EDC contamination, including in high throughput analysis systems as described.

8 Claims, 15 Drawing Sheets

(56) References Cited

OTHER PUBLICATIONS

Htun et al., "Visualization of glucocorticoid receptor translocation and intranuclear organization in living cells with a green fluorescent protein chimera," *Proc. Natl Acad. Sci USA* 93:4845-4850, 1996.
Htun et al., "Direct Visualization of the Human Estrogen Receptor α Reveals a Role for Ligand in the Nuclear Distribution of the Receptor," *Mol. Biol. Cell.* 10(2);471-486, 1999.
Iwanowicz et al., "Reproductive health of bass in the Potomac, USA, drainage: Part 1. Exploring the effects of proximity to wastewater treatment plant discharge," *Environ. Toxic Chem.* 28(5):1072-1083, 2009.
Janssen, "Chemical Exposure and Chronic Disease," Presentation, IPEN side event at IFCS, Budapest, Sep. 25, 2006, (40 pages).
Klokk et al., "Ligand-Specific Dynamics of the Androgen Receptor at Its Response Element in Living Cells," *Mol. Cell Biol.* 27(5):1823-1843, 2007.
Kugathas et al., "Synthetic Glucocorticoids in the Environment: First Results on Their Potential Impacts on Fish," *Environ. Sci. Technol.* 45(6):2377-2383, 2011.
Lee et al., "Employment of the Human Estrogen Receptor β Ligand-Binding Domain and Co-Activator SRC1 Nuclear Receptor-Binding Domain for the Construction of a Yeast Two-Hybrid Detection System for Endocrine Disrupters," *J. Biochem.* 131:399-405, 2002.
Lintelmann et al., "Endocrine Disruptors in the Environment" (IUPAC Technical Report), *Pure Appl. Chem.* 75(5):631-681, 2003.
Mackem et al., "A Glucocorticoid/Retinoic Acid Receptor Chimera That Displays Cytoplasmic/Nuclear Translocation in Response to Retinoic Acid," *J. Biol. Chem.* 276(49):45501-45504, 2001.
Mangelsdorf et al., "The Nuclear Superfamily: The Second Decade," *Cell* 83:835-839, 1995.
Mansilha et al., "Quantification of endocrine disruptors and pesticides in water by gas chromatography-tandem mass spectrometry. Method validation using weighted linear regression schemes," *J Chromatogr. A* 1217(43):6681-6691, 2010.
Martinez et al., "An estrogen receptor chimera senses ligands by nuclear translocation," *J. Steroid Biochem. Mol. Biol.* 97:307-321, 2005.
Miège et al., "Polar organic chemical integrative sampler (POCIS): application for monitoring organic micropollutants in wastewater effluent and surface water," *J. Environ. Monit.*, 14:626-635, 2012; epub Dec. 22, 2011.
Pillon et al., "Binding of Estrogenic Compounds to Recombinant Estrogen Receptor-α: Application to Environmental Analysis," *Environ. Health Pers.* 113(3):278-284, 2005.
Pratt et al., "Steroid receptor interactions with heat shock protein and immunophilin chaperones," *Endocr. Rev.* 18(3):306-360, 1997.
Pratt et al., "Chaperoning of glucocorticoid receptors," *Handb. Exp. Pharmacol.* 172:111-138, 2006.
Ramamoorthy et al., "Estrogenic Activity of a Dieldrin/Toxaphene Mixture in the Mouse Uterus, MCF-7 Human Breast Cancer Cells, and Yeast-Based Estrogen Receptor Assays: No Apparent Synergism," *Endocrin.* 138(4):1520-1527, 1997.
Rayasam et al., "Ligand-Specific Dynamics of the Progesterone Receptor in Living Cells and during Chromatin Remodeling In Vitro," *Mol Cell Biol* 25(6):2406-2418, 2005.
Roda et al., "Analytical approach for monitoring endocrine-disrupting compounds in urban waste water treatment plants" *Analytical and Bioanalytical Chemistry* 385(4):742-752, 2006 Abstract Only.
Roy et al., "A treatise on hazards of endocrine disruptors and tool to evaluate them," *Indian J. Exp. Biol.* 43(11):975-992, 2005.
Salste et al., "Determination of estrogens and estrogenic activity in wastewater effluent by chemical analysis and the bioluminescent yeast assay," *Sci. Total Environ.* 378:343-351, 2007.
Sanseverino et al., "Use of *Saccharomyces cerevisiae* BLYES Expressing Bacterial Bioluminescence for Rapid, Sensitive Detection of Estrogenic Compounds," *App. Environ. Microb.* 71(8):4455-4460, 2005.
Schriks et al., "High-resolution mass spectrometric identification and quantification of glucocorticoid compounds in various wastewaters in the Netherlands," *Environ. Sci. Technol.* 44(12):4766-4774, 2010.
Sutton et al., "Water pollution caused by cosmetic chemicals, cleaning supplies and plastics. Sources of Hormone-Disrupting Chemicals in San Francisco Bay" *Environmental Working Group,* Jul. 11, 2007, 39 pages.
Vandenberg et al., "Hormones and Endocrine-Disrupting Chemicals: Low-Dose Effects and Nonmonotonic Dose Responses," *Endocr. Rev.*, e-published Mar. 14, 2012 as doi:10.1210/er.2011-1050.
Walker et al., "Using inducible vectors to study intracellular trafficking of GFP-tagged steroid/nuclear receptors in living cells," *Methods* (*Comp. To Meth. Enzym.*) 19(3):386-393, 1999.
Wood et al., "Engineered Nuclear Hormone Receptor—Biosensors for Environmental Monitoring and Early Drug Discovery," in *Biosensors for Health, Environment and Biosecurity,* Jul. 2011 (26 pages) http://www.intechopen.com/articles/show/title/engineered-nuclear-hormone-receptor-biosensors-for-environmental-monitoring-and-early-drug-discovery.
The Organisation for Economic Co-operation and Development (OECD) Environment, Health and Safety Publications Series on Testing and Assessment, No. 133, "Peer Review Report for the H295R Cell-Based Assay for Steroidogenesis" Jul. 27, 2010 (107 pages), available on-line at http://www.oecd.org/officialdocuments/displaydocumentpdf/?cote=env/jm/mono(2010)32&doclanguage=en.
"Endocrine Disruptors: Methods for Monitoring EDCs in the Environment," University of Minnesota Department of Environmental & Occupational Health, Fall Semester 2003, *PubH 5103: Exposure to Environmental Hazards* (5 pages), available on-line at http://enhs.umn.edu/current/5103/endocrine/envmonitor.html.
RTI International *Endocrine Disruptor Screening Services,* Brochure (2 pages), available on-line at http://www.rti.org/brochures/rti_edsp.pdf, Feb. 15, 2012.
International Programme on Chemical Safety, "Global Assessment of the State-of-the-Science of Endocrine Disruptors," prepared on behalf of the World Health Organization (WHO), the International Labour Organisation, and the United Nations Environment Programme, 2002 (particularly Chapters 1-4 & 7), available on-line at http://www.who.int/ipcs/publications/new_issues/endocrine_disruptors/en/).
FOXNews.Com, Associated Press, "Study Finds Traces of Drugs in Drinking Water in 24 Major U.S. Regions," Mar. 10, 2008, 4 pages.
ENN: Environmental News Network, *Organic Consumers Association*, "Drinking Water of 41 Million Americans Contaminated with Pharmaceuticals," Aug. 26, 2008, 3 pages.
Water Systems Council (WSC), "Emerging Water Contaminants," Sep. 2005, 2 pages, available on-line at www.watersystemscouncil.org.
"Pharmaceuticals in Our Water Supplies: Are 'Drugged Waters' a Water Quality Threat?", *Arizona Water Resource, The University of Arizona,* Jul.-Aug. 2000. This article appeared on ag.arizona.edu/AZWATER on Jan. 15, 2011.
U.S. Geological Survey TWRI, Book 9, *Handbooks for Water-Resources Investigations, National Field Manual for the Collection of Water-Quality Data,* "Chapter A5. Processing of Water Samples," Version 2, 166 pages, 2002.
International Food Safety Authorities Network (INFOSAN), "Bisphenol A (BPA)—Current state of knowledge and future actions by WHO and FAO," INFOSAN Information Note No. 5/2009—Bisphenol A, 6 pages, Nov. 27, 2009, available on-line at www.who.int/foodsafety.

Peak 1

Peak 2

Peak 3

FIG. 4A
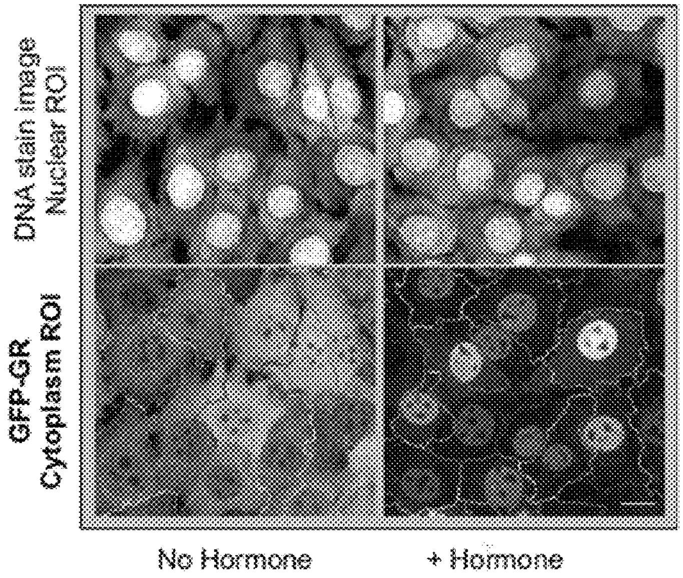
FIG. 4B
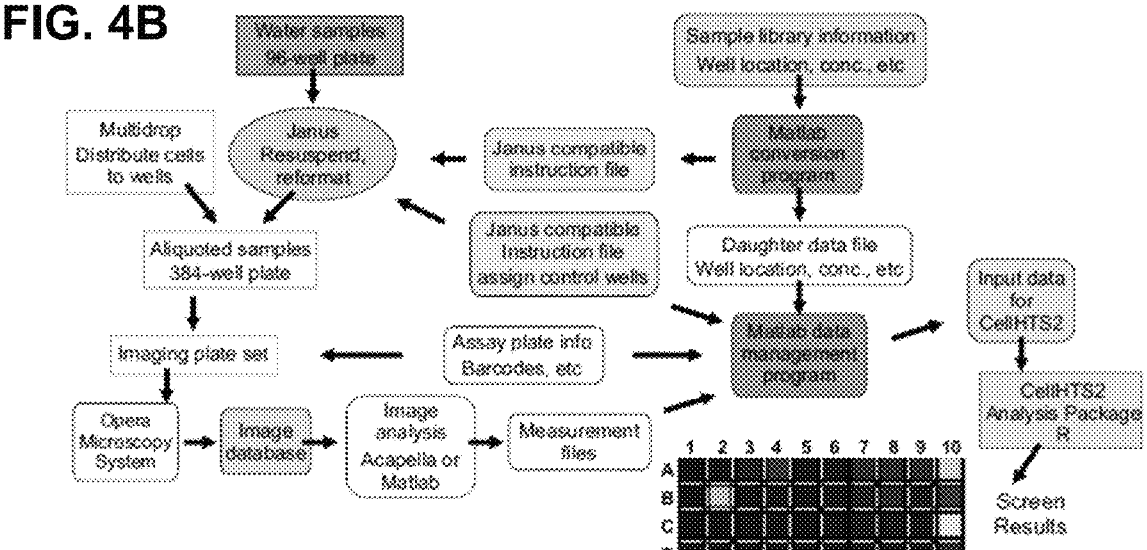
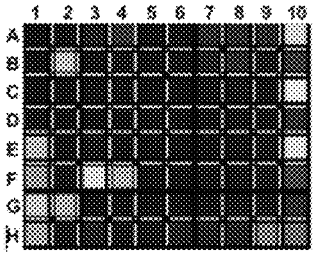
FIG. 4C

GFP-GR
DMSO
1X
10X
20X
50X
100X
100 nM Dexamethasone
Positive samples

GFP-AR
DMSO
1X
10X
20X
50X
100X
100 nM Testosterone
Positive samples

SEQUENCE LISTING

```
<160> NUMBER OF SEQ ID NOS: 22

<210> SEQ ID NO 1
<211> LENGTH: 3213
<212> TYPE: DNA
<213> ORGANISM: artificial sequence
<220> FEATURE:
<223> OTHER INFORMATION: pCI-nGFP-C656G encoding sequence

<400> SEQUENCE: 1
```

-continued

```
atggcccacc atcaccacca tcacggatat ccatacgacg tgccagatta cgctcagtcg     60
agtgccatga gtaaaggaga agaacttttc actggagttg tcccaattct tgttgaatta    120
gatggtgatg ttaatgggca caaattttct gtcagtggag agggtgaagg tgatgcaaca    180
tacggaaaac ttacccttaa atttatttgc actactggaa aactacctgt tccttggcca    240
acacttgtca ctactttcac ttatggtgtt caatgctttt caagataccc agatcatatg    300
aaacagcatg actttttcaa gagtgccatg cccgaaggtt atgtacagga aagaactata    360
tttttcaaag atgacgggaa ctacaagaca cgtgctgaag tcaagtttga aggtgatacc    420
cttgttaata gaatcgagtt aaaaggtatt gattttaaag aagatggaaa cattcttgga    480
cacaaattgg aatacaacta taactcacac aatgtataca tcatggcaga caaacaaaag    540
aatggaatca aagttaactt caaaattaga cacaacattg aagatggaag cgttcaacta    600
gcagaccatt atcaacaaaa tactccaatt ggcgatggcc ctgtcctttt accagacaac    660
cattacctgt ccacacaatc tgccctttcg aaagatccca acgaaaagag agaccacatg    720
gtccttcttg agtttgtaac agctgctggg attacacatg gcatggatga actatacaaa    780
ggcgccggcg ctggtgctgg tgctggcgcc atcagcgcgc tgatcctgga ctccaaagaa    840
tccttagctc cccctggtag agacgaagtc cctggcagtt tgcttggcca ggggaggggg    900
agcgtaatgg acttttataa aagcctgagg ggaggagcta cagtcaaggt ttctgcatct    960
tcgccctcag tggctgctgc ttctcaggca gattccaagc agcagaggat tctccttgat   1020
ttctcgaaag gctccacaag caatgtgcag cagcgacagc agcagcagca gcagcagcag   1080
cagcagcagc agcagcagca gcagcagcag cagccaggct tatccaaagc cgtttcactg   1140
tccatggggc tgtatatggg agagacagaa acaaaagtga tggggaatga cttgggctac   1200
ccacagcagg gccaacttgg cctttcctct ggggaaacag actttcggct tctggaagaa   1260
agcattgcaa acctcaatag gtcgaccagc gttccagaga accccaagag ttcaacgtct   1320
gcaactgggt gtgctacccc gacagagaag gagtttccca aaactcactc ggatgcatct   1380
tcagaacagc aaaatcgaaa aagccagacc ggcaccaacg gaggcagtgt gaaattgtat   1440
cccacagacc aaagcacctt tgacctcttg aaggatttgg agttttccgc tgggtcccca   1500
agtaaagaca caaacgagag tccctggaga tcagatctgt tgatagatga aaacttgctt   1560
tctcctttgg cgggagaaga tgatccattc cttctcgaag ggaacacgaa tgaggattgt   1620
aagcctctta ttttaccgga cactaaacct aaaattaagg atactggaga tacaatctta   1680
tcaagtccca gcagtgtggc actaccccaa gtgaaaacag aaaaagatga tttcattgaa   1740
ctttgcaccc ccggggtaat taagcaagag aaactgggcc cagtttattg tcaggcaagc   1800
ttttctggga caaatataat tggtaataaa atgtctgcca tttctgttca tggtgtgagt   1860
acctctggag gacagatgta ccactatgac atgaatacag catccctttc tcagcagcag   1920
gatcagaagc ctgtttttaa tgtcattcca ccaattcctg ttggttctga aaactggaat   1980
aggtgccaag gctccggaga ggacagcctg acttccttgg gggctctgaa cttcccaggc   2040
cggtcagtgt tttctaatgg gtactcaagc cctggaatga gaccagatgt aagctctcct   2100
ccatccagct cgtcagcagc cacgggacca cctcccaagc tctgcctggt gtgctccgat   2160
gaagcttcag gatgtcatta cggggtgctg acatgtggaa gctgcaaagt attctttaaa   2220
agagcagtgg aaggacagca caattacctt tgtgctggaa gaaacgattg catcattgat   2280
aaaattcgaa ggaaaaactg cccagcatgc cgctatcgga aatgtcttca ggctggaatg   2340
```

-continued

```
aaccttgaag ctcgaaaaac aaagaaaaaa atcaaaggga ttcagcaagc cactgcagga   2400

gtctcacaag acacttcgga aaatcctaac aaaacaatag ttcctgcagc attaccacag   2460

ctcaccccta ccttggtgtc actgctggag gtgattgaac ccgaggtgtt gtatgcagga   2520

tatgatagct ctgttccaga ttcagcatgg agaattatga ccacactcaa catgttaggt   2580

gggcgtcaag tgattgcagc agtgaaatgg gcaaaggcga tactaggctt gagaaactta   2640

cacctcgatg accaaatgac cctgctacag tactcatgga tgtttctcat ggcatttgcc   2700

ttgggttgga gatcatacag acaatcaagc ggaaacctgc tctgctttgc tcctgatctg   2760

attattaatg agcagagaat gtctctaccc ggcatgtatg accaatgtaa acacatgctg   2820

tttgtctcct ctgaattaca aagattgcag gtatcctatg aagagtatct ctgtatgaaa   2880

accttactgc ttctctcctc agttcctaag gaaggtctga agagccaaga gttatttgat   2940

gagattcgaa tgacttatat caaagagcta ggaaaagcca tcgtcaaaag ggaagggaac   3000

tccagtcaga actggcaacg gttttaccaa ctgacaaagc ttctggactc catgcatgag   3060

gtggttgaga atctccttac ctactgcttc cagacatttt tggataagac catgagtatt   3120

gaattcccag agatgttagc tgaaatcatc actaatcaga taccaaaata ttcaaatgga   3180

aatatcaaaa agcttctgtt tcatcaaaaa tga                                 3213
```

```
<210> SEQ ID NO 2
<211> LENGTH: 1070
<212> TYPE: PRT
<213> ORGANISM: artificial sequence
<220> FEATURE:
<223> OTHER INFORMATION: pCI-nGFP-C656G traceable fusion protein

<400> SEQUENCE: 2

Met Ala His His His His His His Gly Tyr Pro Tyr Asp Val Pro Asp
1               5                   10                  15

Tyr Ala Gln Ser Ser Ala Met Ser Lys Gly Glu Glu Leu Phe Thr Gly
            20                  25                  30

Val Val Pro Ile Leu Val Glu Leu Asp Gly Asp Val Asn Gly His Lys
        35                  40                  45

Phe Ser Val Ser Gly Glu Gly Glu Gly Asp Ala Thr Tyr Gly Lys Leu
    50                  55                  60

Thr Leu Lys Phe Ile Cys Thr Thr Gly Lys Leu Pro Val Pro Trp Pro
65                  70                  75                  80

Thr Leu Val Thr Thr Phe Thr Tyr Gly Val Gln Cys Phe Ser Arg Tyr
                85                  90                  95

Pro Asp His Met Lys Gln His Asp Phe Phe Lys Ser Ala Met Pro Glu
            100                 105                 110

Gly Tyr Val Gln Glu Arg Thr Ile Phe Phe Lys Asp Asp Gly Asn Tyr
        115                 120                 125

Lys Thr Arg Ala Glu Val Lys Phe Glu Gly Asp Thr Leu Val Asn Arg
    130                 135                 140

Ile Glu Leu Lys Gly Ile Asp Phe Lys Glu Asp Gly Asn Ile Leu Gly
145                 150                 155                 160

His Lys Leu Glu Tyr Asn Tyr Asn Ser His Asn Val Tyr Ile Met Ala
                165                 170                 175

Asp Lys Gln Lys Asn Gly Ile Lys Val Asn Phe Lys Ile Arg His Asn
            180                 185                 190

Ile Glu Asp Gly Ser Val Gln Leu Ala Asp His Tyr Gln Gln Asn Thr
        195                 200                 205
```

-continued

```
Pro Ile Gly Asp Gly Pro Val Leu Leu Pro Asp Asn His Tyr Leu Ser
    210                 215                 220

Thr Gln Ser Ala Leu Ser Lys Asp Pro Asn Glu Lys Arg Asp His Met
225                 230                 235                 240

Val Leu Leu Glu Phe Val Thr Ala Ala Gly Ile Thr His Gly Met Asp
                245                 250                 255

Glu Leu Tyr Lys Gly Ala Gly Ala Gly Ala Gly Ala Gly Ala Ile Ser
            260                 265                 270

Ala Leu Ile Leu Asp Ser Lys Glu Ser Leu Ala Pro Pro Gly Arg Asp
        275                 280                 285

Glu Val Pro Gly Ser Leu Leu Gly Gln Gly Arg Gly Ser Val Met Asp
    290                 295                 300

Phe Tyr Lys Ser Leu Arg Gly Gly Ala Thr Val Lys Val Ser Ala Ser
305                 310                 315                 320

Ser Pro Ser Val Ala Ala Ala Ser Gln Ala Asp Ser Lys Gln Gln Arg
                325                 330                 335

Ile Leu Leu Asp Phe Ser Lys Gly Ser Thr Ser Asn Val Gln Gln Arg
            340                 345                 350

Gln Gln Gln Gln Gln Gln Gln Gln Gln Gln Gln Gln Gln Gln Gln Gln
        355                 360                 365

Gln Gln Gln Pro Gly Leu Ser Lys Ala Val Ser Leu Ser Met Gly Leu
    370                 375                 380

Tyr Met Gly Glu Thr Glu Thr Lys Val Met Gly Asn Asp Leu Gly Tyr
385                 390                 395                 400

Pro Gln Gln Gly Gln Leu Gly Leu Ser Ser Gly Glu Thr Asp Phe Arg
                405                 410                 415

Leu Leu Glu Glu Ser Ile Ala Asn Leu Asn Arg Ser Thr Ser Val Pro
            420                 425                 430

Glu Asn Pro Lys Ser Ser Thr Ser Ala Thr Gly Cys Ala Thr Pro Thr
        435                 440                 445

Glu Lys Glu Phe Pro Lys Thr His Ser Asp Ala Ser Ser Glu Gln Gln
    450                 455                 460

Asn Arg Lys Ser Gln Thr Gly Thr Asn Gly Gly Ser Val Lys Leu Tyr
465                 470                 475                 480

Pro Thr Asp Gln Ser Thr Phe Asp Leu Leu Lys Asp Leu Glu Phe Ser
                485                 490                 495

Ala Gly Ser Pro Ser Lys Asp Thr Asn Glu Ser Pro Trp Arg Ser Asp
            500                 505                 510

Leu Leu Ile Asp Glu Asn Leu Leu Ser Pro Leu Ala Gly Glu Asp Asp
        515                 520                 525

Pro Phe Leu Leu Glu Gly Asn Thr Asn Glu Asp Cys Lys Pro Leu Ile
    530                 535                 540

Leu Pro Asp Thr Lys Pro Lys Ile Lys Asp Thr Gly Asp Thr Ile Leu
545                 550                 555                 560

Ser Ser Pro Ser Ser Val Ala Leu Pro Gln Val Lys Thr Glu Lys Asp
                565                 570                 575

Asp Phe Ile Glu Leu Cys Thr Pro Gly Val Ile Lys Gln Glu Lys Leu
            580                 585                 590

Gly Pro Val Tyr Cys Gln Ala Ser Phe Ser Gly Thr Asn Ile Ile Gly
        595                 600                 605

Asn Lys Met Ser Ala Ile Ser Val His Gly Val Ser Thr Ser Gly Gly
    610                 615                 620

Gln Met Tyr His Tyr Asp Met Asn Thr Ala Ser Leu Ser Gln Gln Gln
```

```
625                 630                 635                 640

Asp Gln Lys Pro Val Phe Asn Val Ile Pro Pro Ile Pro Val Gly Ser
                645                 650                 655

Glu Asn Trp Asn Arg Cys Gln Gly Ser Gly Glu Asp Ser Leu Thr Ser
            660                 665                 670

Leu Gly Ala Leu Asn Phe Pro Gly Arg Ser Val Phe Ser Asn Gly Tyr
        675                 680                 685

Ser Ser Pro Gly Met Arg Pro Asp Val Ser Ser Pro Pro Ser Ser Ser
    690                 695                 700

Ser Ala Ala Thr Gly Pro Pro Pro Lys Leu Cys Leu Val Cys Ser Asp
705                 710                 715                 720

Glu Ala Ser Gly Cys His Tyr Gly Val Leu Thr Cys Gly Ser Cys Lys
                725                 730                 735

Val Phe Phe Lys Arg Ala Val Glu Gly Gln His Asn Tyr Leu Cys Ala
            740                 745                 750

Gly Arg Asn Asp Cys Ile Ile Asp Lys Ile Arg Arg Lys Asn Cys Pro
        755                 760                 765

Ala Cys Arg Tyr Arg Lys Cys Leu Gln Ala Gly Met Asn Leu Glu Ala
    770                 775                 780

Arg Lys Thr Lys Lys Lys Ile Lys Gly Ile Gln Gln Ala Thr Ala Gly
785                 790                 795                 800

Val Ser Gln Asp Thr Ser Glu Asn Pro Asn Lys Thr Ile Val Pro Ala
                805                 810                 815

Ala Leu Pro Gln Leu Thr Pro Thr Leu Val Ser Leu Leu Glu Val Ile
            820                 825                 830

Glu Pro Glu Val Leu Tyr Ala Gly Tyr Asp Ser Ser Val Pro Asp Ser
        835                 840                 845

Ala Trp Arg Ile Met Thr Thr Leu Asn Met Leu Gly Gly Arg Gln Val
    850                 855                 860

Ile Ala Ala Val Lys Trp Ala Lys Ala Ile Leu Gly Leu Arg Asn Leu
865                 870                 875                 880

His Leu Asp Asp Gln Met Thr Leu Leu Gln Tyr Ser Trp Met Phe Leu
                885                 890                 895

Met Ala Phe Ala Leu Gly Trp Arg Ser Tyr Arg Gln Ser Ser Gly Asn
            900                 905                 910

Leu Leu Cys Phe Ala Pro Asp Leu Ile Ile Asn Glu Gln Arg Met Ser
        915                 920                 925

Leu Pro Gly Met Tyr Asp Gln Cys Lys His Met Leu Phe Val Ser Ser
    930                 935                 940

Glu Leu Gln Arg Leu Gln Val Ser Tyr Glu Glu Tyr Leu Cys Met Lys
945                 950                 955                 960

Thr Leu Leu Leu Leu Ser Ser Val Pro Lys Glu Gly Leu Lys Ser Gln
                965                 970                 975

Glu Leu Phe Asp Glu Ile Arg Met Thr Tyr Ile Lys Glu Leu Gly Lys
            980                 985                 990

Ala Ile Val Lys Arg Glu Gly Asn  Ser Ser Gln Asn Trp  Gln Arg Phe
        995                 1000                 1005

Tyr Gln  Leu Thr Lys Leu Leu  Asp Ser Met His Glu  Val Val Glu
    1010                 1015                 1020

Asn Leu  Leu Thr Tyr Cys Phe  Gln Thr Phe Leu Asp  Lys Thr Met
    1025                 1030                 1035

Ser Ile  Glu Phe Pro Glu Met  Leu Ala Glu Ile Ile  Thr Asn Gln
    1040                 1045                 1050
```

```
Ile Pro  Lys Tyr Ser Asn Gly  Asn Ile Lys Lys Leu  Leu Phe His
    1055                 1060                 1065

Gln Lys
    1070


<210> SEQ ID NO 3
<211> LENGTH: 3516
<212> TYPE: DNA
<213> ORGANISM: artificial sequence
<220> FEATURE:
<223> OTHER INFORMATION: eGFP-hAR encoding sequence

<400> SEQUENCE: 3

atggtgagca agggcgagga gctgttcacc ggggtggtgc ccatcctggt cgagctggac     60

ggcgacgtaa acggccacaa gttcagcgtg tccggcgagg gcgagggcga tgccacctac    120

ggcaagctga ccctgaagtt catctgcacc accggcaagc tgcccgtgcc ctggcccacc    180

ctcgtgacca ccctgaccta cggcgtgcag tgcttcagcc gctaccccga ccacatgaag    240

cagcacgact tcttcaagtc cgccatgccc gaaggctacg tccaggagcg caccatcttc    300

ttcaaggacg acggcaacta caagacccgc gccgaggtga agttcgaggg cgacaccctg    360

gtgaaccgca tcgagctgaa gggcatcgac ttcaaggagg acggcaacat cctggggcac    420

aagctggagt acaactacaa cagccacaac gtctatatca tggccgacaa gcagaagaac    480

ggcatcaagg tgaacttcaa gatccgccac aacatcgagg acggcagcgt gcagctcgcc    540

gaccactacc agcagaacac ccccatcggc gacggccccg tgctgctgcc cgacaaccac    600

tacctgagca cccagtccgc cctgagcaaa gaccccaacg agaagcgcga tcacatggtc    660

ctgctggagt tcgtgaccgc cgccgggatc actctcggca tggacgagct gtacaagtcc    720

ggactcagat ctcgagctca agcttcgaat tcgatggaag tgcagttagg gctgggaagg    780

gtctaccctc ggccgccgtc caagacctac cgaggagctt tccagaatct gttccagagc    840

gtgcgcgaag tgatccagaa cccgggcccc aggcacccag aggccgcgag cgcagcacct    900

cccggcgcca gtttgctgct gctgcagcag cagcagcagc agcagcagca gcagcagcag    960

cagcagcagc agcagcagca gcagcagcag caagagacta gccccaggca gcagcagcag   1020

cagcagggtg aggatggttc tccccaagcc catcgtagag gccccacagg ctacctggtc   1080

ctggatgagg aacagcaacc ttcacagccg cagtcggccc tggagtgcca ccccgagaga   1140

ggttgcgtcc cagagcctgg agccgccgtg gccgccagca aggggctgcc gcagcagctg   1200

ccagcacctc cggacgagga tgactcagct gccccatcca cgttgtccct gctgggcccc   1260

actttccccg gcttaagcag ctgctccgct gaccttaaag acatcctgag cgaggccagc   1320

accatgcaac tccttcagca acagcagcag gaagcagtat ccgaaggcag cagcagcggg   1380

agagcgaggg aggcctcggg ggctcccact tcctccaagg acaattactt agggggcact   1440

tcgaccattt ctgacaacgc caaggagttg tgtaaggcag tgtcggtgtc catgggcctg   1500

ggtgtggagg cgttggagca tctgagtcca ggggaacagc ttcgggggga ttgcatgtac   1560

gccccacttt tgggagttcc acccgctgtg cgtcccactc cttgtgcccc attggccgaa   1620

tgcaaaggtt ctctgctaga cgacagcgca ggcaagagca ctgaagatac tgctgagtat   1680

tccccttca agggaggtta caccaaaggg ctagaaggcg agagcctagg ctgctctggc   1740

agcgctgcag cagggagctc cgggacactt gaactgccgt ctaccctgtc tctctacaag   1800

tccggagcac tggacgaggc agctgcgtac cagagtcgcg actactacaa ctttccactg   1860
```

```
gctctggccg gaccgccgcc ccctccgccg cctccccatc cccacgctcg catcaagctg   1920

gagaacccgc tggactacgg cagcgcctgg gcggctgcgg cggcgcagtg ccgctatggg   1980

gacctggcga gcctgcatgg cgcgggtgca gcgggacccg gttctgggtc accctcagcc   2040

gccgcttcct catcctggca cactctcttc acagccgaag aaggccagtt gtatggaccg   2100

tgtggtggtg gtgggggtgg tggcggcggc ggcggcggcg gcggcggcgg cggcggcggc   2160

ggcggcggcg gcgaggcggg agctgtagcc ccctacggct acactcggcc ccctcagggg   2220

ctggcgggcc aggaaagcga cttcaccgca cctgatgtgt ggtaccctgg cggcatggtg   2280

agcagagtgc cctatcccag tcccacttgt gtcaaaagcg aaatgggccc ctggatggat   2340

agctactccg gaccttacgg ggacatgcgt ttggagactg ccagggacca tgttttgccc   2400

attgactatt actttccacc ccagaagacc tgcctgatct gtggagatga agcttctggg   2460

tgtcactatg gagctctcac atgtggaagc tgcaaggtct tcttcaaaag agccgctgaa   2520

gggaaacaga agtacctgtg cgccagcaga aatgattgca ctattgataa attccgaagg   2580

aaaaattgtc catcttgtcg tcttcggaaa tgttatgaag cagggatgac tctgggagcc   2640

cggaagctga agaaacttgg taatctgaaa ctacaggagg aaggagaggc ttccagcacc   2700

accagcccca ctgaggagac aacccagaag ctgacagtgt cacacattga aggctatgaa   2760

tgtcagccca tctttctgaa tgtcctggaa gccattgagc caggtgtagt gtgtgctgga   2820

cacgacaaca accagcccga ctcctttgca gccttgctct ctagcctcaa tgaactggga   2880

gagagacagc ttgtacacgt ggtcaagtgg gccaaggcct tgcctggctt ccgcaactta   2940

cacgtggacg accagatggc tgtcattcag tactcctgga tggggctcat ggtgtttgcc   3000

atgggctggc gatccttcac caatgtcaac tccaggatgc tctacttcgc ccctgatctg   3060

gttttcaatg agtaccgcat gcacaagtcc cggatgtaca gccagtgtgt ccgaatgagg   3120

cacctctctc aagagtttgg atggctccaa atcacccccc aggaattcct gtgcatgaaa   3180

gcactgctac tcttcagcat tattccagtg gatgggctga aaaatcaaaa attctttgat   3240

gaacttcgaa tgaactacat caaggaactc gatcgtatca ttgcatgcaa aagaaaaaat   3300

cccacatcct gctcaagacg cttctaccag ctcaccaagc tcctggactc cgtgcagcct   3360

attgcgagag agctgcatca gttcactttt gacctgctaa tcaagtcaca catggtgagc   3420

gtggactttc cggaaatgat ggcagagatc atctctgtgc aagtgcccaa gatcctttct   3480

gggaaagtca agcccatcta tttccacacc cagtga                             3516
```

<210> SEQ ID NO 4
<211> LENGTH: 1171
<212> TYPE: PRT
<213> ORGANISM: artificial sequence
<220> FEATURE:
<223> OTHER INFORMATION: eGFP-hAR traceable fusion protein

<400> SEQUENCE: 4

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
```

-continued

```
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly Leu Arg Ser Arg Ala Gln Ala Ser Asn Ser Met Glu Val Gln Leu
                245                 250                 255

Gly Leu Gly Arg Val Tyr Pro Arg Pro Pro Ser Lys Thr Tyr Arg Gly
            260                 265                 270

Ala Phe Gln Asn Leu Phe Gln Ser Val Arg Glu Val Ile Gln Asn Pro
        275                 280                 285

Gly Pro Arg His Pro Glu Ala Ala Ser Ala Ala Pro Pro Gly Ala Ser
    290                 295                 300

Leu Leu Leu Leu Gln Gln Gln Gln Gln Gln Gln Gln Gln Gln Gln Gln
305                 310                 315                 320

Gln Gln Gln Gln Gln Gln Gln Gln Gln Gln Gln Glu Thr Ser Pro Arg
                325                 330                 335

Gln Gln Gln Gln Gln Gln Gly Glu Asp Gly Ser Pro Gln Ala His Arg
            340                 345                 350

Arg Gly Pro Thr Gly Tyr Leu Val Leu Asp Glu Glu Gln Gln Pro Ser
        355                 360                 365

Gln Pro Gln Ser Ala Leu Glu Cys His Pro Glu Arg Gly Cys Val Pro
    370                 375                 380

Glu Pro Gly Ala Ala Val Ala Ala Ser Lys Gly Leu Pro Gln Gln Leu
385                 390                 395                 400

Pro Ala Pro Pro Asp Glu Asp Asp Ser Ala Ala Pro Ser Thr Leu Ser
                405                 410                 415

Leu Leu Gly Pro Thr Phe Pro Gly Leu Ser Ser Cys Ser Ala Asp Leu
            420                 425                 430

Lys Asp Ile Leu Ser Glu Ala Ser Thr Met Gln Leu Leu Gln Gln Gln
        435                 440                 445

Gln Gln Glu Ala Val Ser Glu Gly Ser Ser Ser Gly Arg Ala Arg Glu
    450                 455                 460

Ala Ser Gly Ala Pro Thr Ser Ser Lys Asp Asn Tyr Leu Gly Gly Thr
465                 470                 475                 480

Ser Thr Ile Ser Asp Asn Ala Lys Glu Leu Cys Lys Ala Val Ser Val
                485                 490                 495
```

```
Ser Met Gly Leu Gly Val Glu Ala Leu Glu His Leu Ser Pro Gly Glu
            500                 505                 510

Gln Leu Arg Gly Asp Cys Met Tyr Ala Pro Leu Leu Gly Val Pro Pro
        515                 520                 525

Ala Val Arg Pro Thr Pro Cys Ala Pro Leu Ala Glu Cys Lys Gly Ser
    530                 535                 540

Leu Leu Asp Asp Ser Ala Gly Lys Ser Thr Glu Asp Thr Ala Glu Tyr
545                 550                 555                 560

Ser Pro Phe Lys Gly Gly Tyr Thr Lys Gly Leu Glu Gly Glu Ser Leu
                565                 570                 575

Gly Cys Ser Gly Ser Ala Ala Ala Gly Ser Ser Gly Thr Leu Glu Leu
            580                 585                 590

Pro Ser Thr Leu Ser Leu Tyr Lys Ser Gly Ala Leu Asp Glu Ala Ala
        595                 600                 605

Ala Tyr Gln Ser Arg Asp Tyr Tyr Asn Phe Pro Leu Ala Leu Ala Gly
    610                 615                 620

Pro Pro Pro Pro Pro Pro Pro Pro His Pro His Ala Arg Ile Lys Leu
625                 630                 635                 640

Glu Asn Pro Leu Asp Tyr Gly Ser Ala Trp Ala Ala Ala Ala Ala Gln
                645                 650                 655

Cys Arg Tyr Gly Asp Leu Ala Ser Leu His Gly Ala Gly Ala Ala Gly
            660                 665                 670

Pro Gly Ser Gly Ser Pro Ser Ala Ala Ala Ser Ser Ser Trp His Thr
        675                 680                 685

Leu Phe Thr Ala Glu Glu Gly Gln Leu Tyr Gly Pro Cys Gly Gly Gly
    690                 695                 700

Gly Gly Gly Gly Gly Gly Gly Gly Gly Gly Gly Gly Gly Gly Gly Gly
705                 710                 715                 720

Gly Gly Gly Gly Glu Ala Gly Ala Val Ala Pro Tyr Gly Tyr Thr Arg
                725                 730                 735

Pro Pro Gln Gly Leu Ala Gly Gln Glu Ser Asp Phe Thr Ala Pro Asp
            740                 745                 750

Val Trp Tyr Pro Gly Gly Met Val Ser Arg Val Pro Tyr Pro Ser Pro
        755                 760                 765

Thr Cys Val Lys Ser Glu Met Gly Pro Trp Met Asp Ser Tyr Ser Gly
    770                 775                 780

Pro Tyr Gly Asp Met Arg Leu Glu Thr Ala Arg Asp His Val Leu Pro
785                 790                 795                 800

Ile Asp Tyr Tyr Phe Pro Pro Gln Lys Thr Cys Leu Ile Cys Gly Asp
                805                 810                 815

Glu Ala Ser Gly Cys His Tyr Gly Ala Leu Thr Cys Gly Ser Cys Lys
            820                 825                 830

Val Phe Phe Lys Arg Ala Ala Glu Gly Lys Gln Lys Tyr Leu Cys Ala
        835                 840                 845

Ser Arg Asn Asp Cys Thr Ile Asp Lys Phe Arg Arg Lys Asn Cys Pro
    850                 855                 860

Ser Cys Arg Leu Arg Lys Cys Tyr Glu Ala Gly Met Thr Leu Gly Ala
865                 870                 875                 880

Arg Lys Leu Lys Lys Leu Gly Asn Leu Lys Leu Gln Glu Glu Gly Glu
                885                 890                 895

Ala Ser Ser Thr Thr Ser Pro Thr Glu Glu Thr Thr Gln Lys Leu Thr
            900                 905                 910
```

```
Val Ser His Ile Glu Gly Tyr Glu Cys Gln Pro Ile Phe Leu Asn Val
        915                 920                 925

Leu Glu Ala Ile Glu Pro Gly Val Val Cys Ala Gly His Asp Asn Asn
    930                 935                 940

Gln Pro Asp Ser Phe Ala Ala Leu Leu Ser Ser Leu Asn Glu Leu Gly
945                 950                 955                 960

Glu Arg Gln Leu Val His Val Val Lys Trp Ala Lys Ala Leu Pro Gly
                965                 970                 975

Phe Arg Asn Leu His Val Asp Asp Gln Met Ala Val Ile Gln Tyr Ser
            980                 985                 990

Trp Met Gly Leu Met Val Phe Ala  Met Gly Trp Arg Ser  Phe Thr Asn
        995                 1000                1005

Val Asn  Ser Arg Met Leu Tyr  Phe Ala Pro Asp Leu  Val Phe Asn
    1010                1015                1020

Glu Tyr  Arg Met His Lys Ser  Arg Met Tyr Ser Gln  Cys Val Arg
    1025                1030                1035

Met Arg  His Leu Ser Gln Glu  Phe Gly Trp Leu Gln  Ile Thr Pro
    1040                1045                1050

Gln Glu  Phe Leu Cys Met Lys  Ala Leu Leu Leu Phe  Ser Ile Ile
    1055                1060                1065

Pro Val  Asp Gly Leu Lys Asn  Gln Lys Phe Phe Asp  Glu Leu Arg
    1070                1075                1080

Met Asn  Tyr Ile Lys Glu Leu  Asp Arg Ile Ile Ala  Cys Lys Arg
    1085                1090                1095

Lys Asn  Pro Thr Ser Cys Ser  Arg Arg Phe Tyr Gln  Leu Thr Lys
    1100                1105                1110

Leu Leu  Asp Ser Val Gln Pro  Ile Ala Arg Glu Leu  His Gln Phe
    1115                1120                1125

Thr Phe  Asp Leu Leu Ile Lys  Ser His Met Val Ser  Val Asp Phe
    1130                1135                1140

Pro Glu  Met Met Ala Glu Ile  Ile Ser Val Gln Val  Pro Lys Ile
    1145                1150                1155

Leu Ser  Gly Lys Val Lys Pro  Ile Tyr Phe His Thr  Gln
    1160                1165                1170
```

<210> SEQ ID NO 5
<211> LENGTH: 3261
<212> TYPE: DNA
<213> ORGANISM: artificial sequence
<220> FEATURE:
<223> OTHER INFORMATION: eGFP-GR-ER310 encoding sequence

<400> SEQUENCE: 5

```
atggtgagca agggcgagga gctgttcacc ggggtggtgc ccatcctggt cgagctggac     60

ggcgacgtaa acggccacaa gttcagcgtg tccggcgagg gcgagggcga tgccacctac    120

ggcaagctga ccctgaagtt catctgcacc accggcaagc tgcccgtgcc ctggcccacc    180

ctcgtgacca ccctgaccta cggcgtgcag tgcttcagcc gctaccccga ccacatgaag    240

cagcacgact tcttcaagtc cgccatgccc gaaggctacg tccaggagcg caccatcttc    300

ttcaaggacg acggcaacta caagacccgc gccgaggtga agttcgaggg cgacaccctg    360

gtgaaccgca tcgagctgaa gggcatcgac ttcaaggagg acggcaacat cctggggcac    420

aagctggagt acaactacaa cagccacaac gtctatatca tggccgacaa gcagaagaac    480

ggcatcaagg tgaacttcaa gatccgccac aacatcgagg acggcagcgt gcagctcgcc    540
```

```
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagggc    720
gctggagcag ggctggagc cggagctgac tccaaagaat cattaactcc tggtagagaa    780
gaaaacccca gcagtgtgct tgctcaggag aggggagatg tgatggactt ctataaaacc    840
ctaagaggag gagctactgt gaaggtttct gcgtcttcac cctcactggc tgtcgcttct    900
caatcagact ccaagcagcg aagacttttg gttgattttc caaaaggctc agtaagcaat    960
gcgcagcagc cagatctgtc caaagcagtt tcactctcaa tgggactgta tatgggagag   1020
acagaaacaa aagtgatggg aaatgacctg ggattcccac agcagggcca aatcagcctt   1080
tcctcggggg aaacagactt aaagcttttg gaagaaagca ttgcaaacct caataggtcg   1140
accagtgttc cagagaaccc caagagttca gcatccactg ctgtgtctgc tgcccccaca   1200
gagaaggagt ttccaaaaac tcactctgat gtatcttcag aacagcaaca tttgaagggc   1260
cagactggca ccaacggtgg caatgtgaaa ttgtatacca cagaccaaag cacctttgac   1320
attttgcagg atttggagtt ttcttctggg tccccaggta aagagacgaa tgagagtcct   1380
tggagatcag acctgttgat agatgaaaac tgtttgcttt ctcctctggc gggagaagac   1440
gattcattcc ttttggaagg aaactcgaat gaggactgca agcctctcat tttaccggac   1500
actaaaccca aaattaagga taatggagat ctggttttgt caagccccag taatgtaaca   1560
ctgccccaag tgaaaacaga aaaagaagat ttcatcgaac tctgcacccc tggggtaatt   1620
aagcaagaga aactgggcac agtttactgt caggcaagct ttcctggagc aaatataatt   1680
ggtaataaaa tgtctgccat ttctgttcat ggtgtgagta cctctggagg acagatgtac   1740
cactatgaca tgaatacagc atccctttct caacagcagg atcagaagcc tatttttaat   1800
gtcattccac caattcccgt tggttccgaa aattggaata ggtgccaagg atctggagat   1860
gacaacttga cttctctggg gactctgaac ttccctggtc gaacagtttt ttctaatggc   1920
tattcaagcc ccagcatgag accagatgta agctctcctc catccagctc ctcaacagca   1980
acaacaggac cacctcccaa actctgcctg gtgtgctctg atgaagcttc aggatgtcat   2040
tatggagtct taacttgtgg aagctgtaaa gttttcttca aaagagcagt ggaaggacag   2100
cacaattacc tatgtgctgg aaggaatgat tgcatcatcg ataaaattcg aagaaaaaac   2160
tgcccagcat gccgctatcg aaaatgtctt caggctggaa tgaacctgga agctcgaaaa   2220
acaaagaaaa aaataaaagg aattcagcag gccactacag gagtctcaca agaaacctct   2280
gaaaatcctg gtaacaaaac aatagttcct gcaacgttac cacaactcac ccctaccctg   2340
gtgtcactgt tggaggttat tgaacctgaa gtgttatatg caggatatga tagctctgtt   2400
ctgacggccg accagatggt cagtgccttg ttggatgctg agccccccat actctattcc   2460
gagtatgatc ctaccagacc cttcagtgaa gcttcgatga tgggcttact gaccaacctg   2520
gcagacaggg agctggttca catgatcaac tgggcgaaga gggtgccagg ctttgtggat   2580
ttgaccctcc atgatcaggt ccaccttcta gaatgtgcct ggctagagat cctgatgatt   2640
ggtctcgtct ggcgctccat ggagcaccca gggaagctac tgtttgctcc taacttgctc   2700
ttggacagga accagggaaa atgtgtagag ggcatggtgg agatcttcga catgctgctg   2760
gctacatcat ctcggttccg catgatgaat ctgcagggag aggagtttgt gtgcctcaaa   2820
tctattattt tgcttaattc tggagtgtac acatttctgt ccagcaccct gaagtctctg   2880
gaagagaagg accatatcca ccgagtcctg gacaagatca cagacacttt gatccacctg   2940
```

```
atggccaagg caggcctgac cctgcagcag cagcaccagc ggctggccca gctcctcctc   3000

atcctctccc acatcaggca catgagtaac aaaggcatgg agcatctgta cagcatgaag   3060

tgcaagaacg tggtgcccct ctatgacctg ctgctggaga tgctggacgc ccaccgccta   3120

catgcgccca ctagccgtgg aggggcatcc gtggaggaga cggaccaaag ccacttggcc   3180

actgcgggct ctacttcatc gcattccttg caaaagtatt acatcacggg ggaggcagag   3240

ggtttccctg ccacggtcta a                                             3261


<210> SEQ ID NO 6
<211> LENGTH: 1086
<212> TYPE: PRT
<213> ORGANISM: artificial sequence
<220> FEATURE:
<223> OTHER INFORMATION: eGFP-GR-ER310 traceable fusion protein

<400> SEQUENCE: 6

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Gly
225                 230                 235                 240

Ala Gly Ala Gly Ala Gly Ala Gly Ala Asp Ser Lys Glu Ser Leu Thr
                245                 250                 255

Pro Gly Arg Glu Glu Asn Pro Ser Ser Val Leu Ala Gln Glu Arg Gly
            260                 265                 270

Asp Val Met Asp Phe Tyr Lys Thr Leu Arg Gly Gly Ala Thr Val Lys
        275                 280                 285

Val Ser Ala Ser Ser Pro Ser Leu Ala Val Ala Ser Gln Ser Asp Ser
    290                 295                 300
```

```
Lys Gln Arg Arg Leu Leu Val Asp Phe Pro Lys Gly Ser Val Ser Asn
305                 310                 315                 320

Ala Gln Gln Pro Asp Leu Ser Lys Ala Val Ser Leu Ser Met Gly Leu
                325                 330                 335

Tyr Met Gly Glu Thr Glu Thr Lys Val Met Gly Asn Asp Leu Gly Phe
            340                 345                 350

Pro Gln Gln Gly Gln Ile Ser Leu Ser Ser Gly Glu Thr Asp Leu Lys
        355                 360                 365

Leu Leu Glu Glu Ser Ile Ala Asn Leu Asn Arg Ser Thr Ser Val Pro
    370                 375                 380

Glu Asn Pro Lys Ser Ser Ala Ser Thr Ala Val Ser Ala Ala Pro Thr
385                 390                 395                 400

Glu Lys Glu Phe Pro Lys Thr His Ser Asp Val Ser Ser Glu Gln Gln
                405                 410                 415

His Leu Lys Gly Gln Thr Gly Thr Asn Gly Gly Asn Val Lys Leu Tyr
            420                 425                 430

Thr Thr Asp Gln Ser Thr Phe Asp Ile Leu Gln Asp Leu Glu Phe Ser
        435                 440                 445

Ser Gly Ser Pro Gly Lys Glu Thr Asn Glu Ser Pro Trp Arg Ser Asp
    450                 455                 460

Leu Leu Ile Asp Glu Asn Cys Leu Leu Ser Pro Leu Ala Gly Glu Asp
465                 470                 475                 480

Asp Ser Phe Leu Leu Glu Gly Asn Ser Asn Glu Asp Cys Lys Pro Leu
                485                 490                 495

Ile Leu Pro Asp Thr Lys Pro Lys Ile Lys Asp Asn Gly Asp Leu Val
            500                 505                 510

Leu Ser Ser Pro Ser Asn Val Thr Leu Pro Gln Val Lys Thr Glu Lys
        515                 520                 525

Glu Asp Phe Ile Glu Leu Cys Thr Pro Gly Val Ile Lys Gln Glu Lys
    530                 535                 540

Leu Gly Thr Val Tyr Cys Gln Ala Ser Phe Pro Gly Ala Asn Ile Ile
545                 550                 555                 560

Gly Asn Lys Met Ser Ala Ile Ser Val His Gly Val Ser Thr Ser Gly
                565                 570                 575

Gly Gln Met Tyr His Tyr Asp Met Asn Thr Ala Ser Leu Ser Gln Gln
            580                 585                 590

Gln Asp Gln Lys Pro Ile Phe Asn Val Ile Pro Pro Ile Pro Val Gly
        595                 600                 605

Ser Glu Asn Trp Asn Arg Cys Gln Gly Ser Gly Asp Asp Asn Leu Thr
    610                 615                 620

Ser Leu Gly Thr Leu Asn Phe Pro Gly Arg Thr Val Phe Ser Asn Gly
625                 630                 635                 640

Tyr Ser Ser Pro Ser Met Arg Pro Asp Val Ser Ser Pro Pro Ser Ser
                645                 650                 655

Ser Ser Thr Ala Thr Thr Gly Pro Pro Pro Lys Leu Cys Leu Val Cys
            660                 665                 670

Ser Asp Glu Ala Ser Gly Cys His Tyr Gly Val Leu Thr Cys Gly Ser
        675                 680                 685

Cys Lys Val Phe Phe Lys Arg Ala Val Glu Gly Gln His Asn Tyr Leu
    690                 695                 700

Cys Ala Gly Arg Asn Asp Cys Ile Ile Asp Lys Ile Arg Arg Lys Asn
705                 710                 715                 720
```

-continued

```
Cys Pro Ala Cys Arg Tyr Arg Lys Cys Leu Gln Ala Gly Met Asn Leu
                725                 730                 735

Glu Ala Arg Lys Thr Lys Lys Lys Ile Lys Gly Ile Gln Gln Ala Thr
            740                 745                 750

Thr Gly Val Ser Gln Glu Thr Ser Glu Asn Pro Gly Asn Lys Thr Ile
        755                 760                 765

Val Pro Ala Thr Leu Pro Gln Leu Thr Pro Thr Leu Val Ser Leu Leu
    770                 775                 780

Glu Val Ile Glu Pro Glu Val Leu Tyr Ala Gly Tyr Asp Ser Ser Val
785                 790                 795                 800

Leu Thr Ala Asp Gln Met Val Ser Ala Leu Leu Asp Ala Glu Pro Pro
                805                 810                 815

Ile Leu Tyr Ser Glu Tyr Asp Pro Thr Arg Pro Phe Ser Glu Ala Ser
            820                 825                 830

Met Met Gly Leu Leu Thr Asn Leu Ala Asp Arg Glu Leu Val His Met
        835                 840                 845

Ile Asn Trp Ala Lys Arg Val Pro Gly Phe Val Asp Leu Thr Leu His
    850                 855                 860

Asp Gln Val His Leu Leu Glu Cys Ala Trp Leu Glu Ile Leu Met Ile
865                 870                 875                 880

Gly Leu Val Trp Arg Ser Met Glu His Pro Gly Lys Leu Leu Phe Ala
                885                 890                 895

Pro Asn Leu Leu Leu Asp Arg Asn Gln Gly Lys Cys Val Glu Gly Met
            900                 905                 910

Val Glu Ile Phe Asp Met Leu Leu Ala Thr Ser Ser Arg Phe Arg Met
        915                 920                 925

Met Asn Leu Gln Gly Glu Glu Phe Val Cys Leu Lys Ser Ile Ile Leu
    930                 935                 940

Leu Asn Ser Gly Val Tyr Thr Phe Leu Ser Ser Thr Leu Lys Ser Leu
945                 950                 955                 960

Glu Glu Lys Asp His Ile His Arg Val Leu Asp Lys Ile Thr Asp Thr
                965                 970                 975

Leu Ile His Leu Met Ala Lys Ala Gly Leu Thr Leu Gln Gln Gln His
            980                 985                 990

Gln Arg Leu Ala Gln Leu Leu Leu  Ile Leu Ser His Ile  Arg His Met
        995                 1000                1005

Ser Asn  Lys Gly Met Glu His  Leu Tyr Ser Met Lys  Cys Lys Asn
    1010                1015                1020

Val Val  Pro Leu Tyr Asp Leu  Leu Leu Glu Met Leu  Asp Ala His
    1025                1030                1035

Arg Leu  His Ala Pro Thr Ser  Arg Gly Gly Ala Ser  Val Glu Glu
    1040                1045                1050

Thr Asp  Gln Ser His Leu Ala  Thr Ala Gly Ser Thr  Ser Ser His
    1055                1060                1065

Ser Leu  Gln Lys Tyr Tyr Ile  Thr Gly Glu Ala Glu  Gly Phe Pro
    1070                1075                1080

Ala Thr  Val
    1085
```

<210> SEQ ID NO 7
<211> LENGTH: 3141
<212> TYPE: DNA
<213> ORGANISM: artificial sequence
<220> FEATURE:
<223> OTHER INFORMATION: eGFP-GR-TR216 encoding sequence

<400> SEQUENCE: 7

```
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgaccta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagggc    720
gctggagcag gggctggagc cggagctgac tccaaagaat cattaactcc tggtagagaa    780
gaaaacccca gcagtgtgct tgctcaggag aggggagatg tgatggactt ctataaaacc    840
ctaagaggag gagctactgt gaaggtttct gcgtcttcac cctcactggc tgtcgcttct    900
caatcagact ccaagcagcg aagacttttg gttgattttc caaaaggctc agtaagcaat    960
gcgcagcagc cagatctgtc caaagcagtt tcactctcaa tgggactgta tatgggagag   1020
acagaaacaa aagtgatggg aaatgacctg ggattcccac agcagggcca aatcagcctt   1080
tcctcggggg aaacagactt aaagcttttg gaagaaagca ttgcaaacct caataggtcg   1140
accagtgttc cagagaaccc caagagttca gcatccactg ctgtgtctgc tgcccccaca   1200
gagaaggagt ttccaaaaac tcactctgat gtatcttcag aacagcaaca tttgaagggc   1260
cagactggca ccaacggtgg caatgtgaaa ttgtatacca cagaccaaag cacctttgac   1320
attttgcagg atttggagtt ttcttctggg tccccaggta aagagacgaa tgagagtcct   1380
tggagatcag acctgttgat agatgaaaac tgtttgcttt ctcctctggc gggagaagac   1440
gattcattcc ttttggaagg aaactcgaat gaggactgca agcctctcat tttaccggac   1500
actaaaccca aaattaagga taatggagat ctggttttgt caagccccag taatgtaaca   1560
ctgccccaag tgaaaacaga aaaagaagat ttcatcgaac tctgcacccc tggggtaatt   1620
aagcaagaga aactgggcac agtttactgt caggcaagct ttcctggagc aaatataatt   1680
ggtaataaaa tgtctgccat ttctgttcat ggtgtgagta cctctggagg acagatgtac   1740
cactatgaca tgaatacagc atccctttct caacagcagg atcagaagcc tatttttaat   1800
gtcattccac caattcccgt tggttccgaa aattggaata ggtgccaagg atctggagat   1860
gacaacttga cttctctggg gactctgaac ttccctggtc gaacagtttt ttctaatggc   1920
tattcaagcc ccagcatgag accagatgta agctctcctc catccagctc ctcaacagca   1980
acaacaggac cacctcccaa actctgcctg gtgtgctctg atgaagcttc aggatgtcat   2040
tatggagtct taacttgtgg aagctgtaaa gttttcttca aaagagcagt ggaaggacag   2100
cacaattacc tatgtgctgg aaggaatgat tgcatcatcg ataaaattcg aagaaaaaac   2160
tgcccagcat gccgctatcg aaaatgtctt caggctggaa tgaacctgga agctcgaaaa   2220
acaaagaaaa aaataaaagg aattcagcag gccactacag gagtctcaca agaaacctct   2280
```

```
gaaaatcctg gtaacaaaac aatagttcct gcaacgttac cacaactcac ccctaccctg   2340

gtgtcactgt tggaggttat tgaacctgaa gtgttatatg caggatatga tagctctgtt   2400

gacgaggaat gggagctcat caaaactgtc accgaagccc atgtggcgac caacgcccaa   2460

ggcagccact ggaagcaaaa acggaaattc ctgccagaag acattggaca agcaccaata   2520

gtcaatgccc cagaaggtgg aaaggttgac ttggaagcct tcagccattt tacaaaaatc   2580

atcacaccag caattaccag agtggtggat tttgccaaaa agttgcctat gttttgtgag   2640

ctgccatgtg aagaccagat catcctcctc aaaggctgct gcatggagat catgtccctt   2700

cgcgctgctg tgcgctatga cccagaaagt gagactttaa ccttgaatgg ggaaatggca   2760

gtgacacggg gccagctgaa aaatgggggt cttggggtgg tgtcagacgc catctttgac   2820

ctgggcatgt ctctgtcttc tttcaacctg gatgacactg aagtagccct ccttcaggcc   2880

gtcctgctga tgtcttcaga tcgcccgggg cttgcctgtg ttgagagaat agaaaagtac   2940

caagatagtt tcctgctggc ctttgaacac tatatcaatt accgaaaaca ccacgtgaca   3000

cacttttggc caaaactcct gatgaaggtg acagatctgc ggatgatagg agcctgccat   3060

gccagccgct tcctgcacat gaaggtggaa tgccccacag aactcttccc ccctttgttc   3120

ttggaagtgt tcgaggatta a                                              3141
```

<210> SEQ ID NO 8
<211> LENGTH: 1046
<212> TYPE: PRT
<213> ORGANISM: artificial sequence
<220> FEATURE:
<223> OTHER INFORMATION: eGFP-GR-TR216 traceable fusion protein

<400> SEQUENCE: 8

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205
```

```
Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Gly
225                 230                 235                 240

Ala Gly Ala Gly Ala Gly Ala Gly Ala Asp Ser Lys Glu Ser Leu Thr
                245                 250                 255

Pro Gly Arg Glu Glu Asn Pro Ser Ser Val Leu Ala Gln Glu Arg Gly
            260                 265                 270

Asp Val Met Asp Phe Tyr Lys Thr Leu Arg Gly Gly Ala Thr Val Lys
        275                 280                 285

Val Ser Ala Ser Ser Pro Ser Leu Ala Val Ala Ser Gln Ser Asp Ser
    290                 295                 300

Lys Gln Arg Arg Leu Leu Val Asp Phe Pro Lys Gly Ser Val Ser Asn
305                 310                 315                 320

Ala Gln Gln Pro Asp Leu Ser Lys Ala Val Ser Leu Ser Met Gly Leu
                325                 330                 335

Tyr Met Gly Glu Thr Glu Thr Lys Val Met Gly Asn Asp Leu Gly Phe
            340                 345                 350

Pro Gln Gln Gly Gln Ile Ser Leu Ser Ser Gly Glu Thr Asp Leu Lys
        355                 360                 365

Leu Leu Glu Glu Ser Ile Ala Asn Leu Asn Arg Ser Thr Ser Val Pro
    370                 375                 380

Glu Asn Pro Lys Ser Ser Ala Ser Thr Ala Val Ser Ala Ala Pro Thr
385                 390                 395                 400

Glu Lys Glu Phe Pro Lys Thr His Ser Asp Val Ser Ser Glu Gln Gln
                405                 410                 415

His Leu Lys Gly Gln Thr Gly Thr Asn Gly Gly Asn Val Lys Leu Tyr
            420                 425                 430

Thr Thr Asp Gln Ser Thr Phe Asp Ile Leu Gln Asp Leu Glu Phe Ser
        435                 440                 445

Ser Gly Ser Pro Gly Lys Glu Thr Asn Glu Ser Pro Trp Arg Ser Asp
    450                 455                 460

Leu Leu Ile Asp Glu Asn Cys Leu Leu Ser Pro Leu Ala Gly Glu Asp
465                 470                 475                 480

Asp Ser Phe Leu Leu Glu Gly Asn Ser Asn Glu Asp Cys Lys Pro Leu
                485                 490                 495

Ile Leu Pro Asp Thr Lys Pro Lys Ile Lys Asp Asn Gly Asp Leu Val
            500                 505                 510

Leu Ser Ser Pro Ser Asn Val Thr Leu Pro Gln Val Lys Thr Glu Lys
        515                 520                 525

Glu Asp Phe Ile Glu Leu Cys Thr Pro Gly Val Ile Lys Gln Glu Lys
    530                 535                 540

Leu Gly Thr Val Tyr Cys Gln Ala Ser Phe Pro Gly Ala Asn Ile Ile
545                 550                 555                 560

Gly Asn Lys Met Ser Ala Ile Ser Val His Gly Val Ser Thr Ser Gly
                565                 570                 575

Gly Gln Met Tyr His Tyr Asp Met Asn Thr Ala Ser Leu Ser Gln Gln
            580                 585                 590

Gln Asp Gln Lys Pro Ile Phe Asn Val Ile Pro Pro Ile Pro Val Gly
        595                 600                 605

Ser Glu Asn Trp Asn Arg Cys Gln Gly Ser Gly Asp Asp Asn Leu Thr
    610                 615                 620

Ser Leu Gly Thr Leu Asn Phe Pro Gly Arg Thr Val Phe Ser Asn Gly
```

-continued

```
625                 630                 635                 640

Tyr Ser Ser Pro Ser Met Arg Pro Asp Val Ser Ser Pro Pro Ser Ser
                645                 650                 655

Ser Ser Thr Ala Thr Thr Gly Pro Pro Pro Lys Leu Cys Leu Val Cys
            660                 665                 670

Ser Asp Glu Ala Ser Gly Cys His Tyr Gly Val Leu Thr Cys Gly Ser
        675                 680                 685

Cys Lys Val Phe Phe Lys Arg Ala Val Glu Gly Gln His Asn Tyr Leu
    690                 695                 700

Cys Ala Gly Arg Asn Asp Cys Ile Ile Asp Lys Ile Arg Arg Lys Asn
705                 710                 715                 720

Cys Pro Ala Cys Arg Tyr Arg Lys Cys Leu Gln Ala Gly Met Asn Leu
                725                 730                 735

Glu Ala Arg Lys Thr Lys Lys Lys Ile Lys Gly Ile Gln Gln Ala Thr
            740                 745                 750

Thr Gly Val Ser Gln Glu Thr Ser Glu Asn Pro Gly Asn Lys Thr Ile
        755                 760                 765

Val Pro Ala Thr Leu Pro Gln Leu Thr Pro Thr Leu Val Ser Leu Leu
    770                 775                 780

Glu Val Ile Glu Pro Glu Val Leu Tyr Ala Gly Tyr Asp Ser Ser Val
785                 790                 795                 800

Asp Glu Glu Trp Glu Leu Ile Lys Thr Val Thr Glu Ala His Val Ala
                805                 810                 815

Thr Asn Ala Gln Gly Ser His Trp Lys Gln Lys Arg Lys Phe Leu Pro
            820                 825                 830

Glu Asp Ile Gly Gln Ala Pro Ile Val Asn Ala Pro Glu Gly Gly Lys
        835                 840                 845

Val Asp Leu Glu Ala Phe Ser His Phe Thr Lys Ile Ile Thr Pro Ala
    850                 855                 860

Ile Thr Arg Val Val Asp Phe Ala Lys Lys Leu Pro Met Phe Cys Glu
865                 870                 875                 880

Leu Pro Cys Glu Asp Gln Ile Ile Leu Leu Lys Gly Cys Cys Met Glu
                885                 890                 895

Ile Met Ser Leu Arg Ala Ala Val Arg Tyr Asp Pro Glu Ser Glu Thr
            900                 905                 910

Leu Thr Leu Asn Gly Glu Met Ala Val Thr Arg Gly Gln Leu Lys Asn
        915                 920                 925

Gly Gly Leu Gly Val Val Ser Asp Ala Ile Phe Asp Leu Gly Met Ser
    930                 935                 940

Leu Ser Ser Phe Asn Leu Asp Asp Thr Glu Val Ala Leu Leu Gln Ala
945                 950                 955                 960

Val Leu Leu Met Ser Ser Asp Arg Pro Gly Leu Ala Cys Val Glu Arg
                965                 970                 975

Ile Glu Lys Tyr Gln Asp Ser Phe Leu Leu Ala Phe Glu His Tyr Ile
            980                 985                 990

Asn Tyr Arg Lys His His Val Thr  His Phe Trp Pro Lys  Leu Leu Met
        995                 1000                 1005

Lys Val  Thr Asp Leu Arg Met  Ile Gly Ala Cys His  Ala Ser Arg
    1010                 1015                 1020

Phe Leu  His Met Lys Val Glu  Cys Pro Thr Glu Leu  Phe Pro Pro
    1025                 1030                 1035

Leu Phe  Leu Glu Val Phe Glu  Asp
    1040                 1045
```

<210> SEQ ID NO 9
<211> LENGTH: 22
<212> TYPE: DNA
<213> ORGANISM: Artificial Sequence
<220> FEATURE:
<223> OTHER INFORMATION: Synthetic primer

<400> SEQUENCE: 9
cttctggcaa tggcaaggac tc 22

<210> SEQ ID NO 10
<211> LENGTH: 24
<212> TYPE: DNA
<213> ORGANISM: Artificial Sequence
<220> FEATURE:
<223> OTHER INFORMATION: Synthetic primer

<400> SEQUENCE: 10
cagcatcatg ccatcataca caca 24

<210> SEQ ID NO 11
<211> LENGTH: 22
<212> TYPE: DNA
<213> ORGANISM: Artificial Sequence
<220> FEATURE:
<223> OTHER INFORMATION: Synthetic primer

<400> SEQUENCE: 11
tgtcaccagg gatgagagac gg 22

<210> SEQ ID NO 12
<211> LENGTH: 23
<212> TYPE: DNA
<213> ORGANISM: Artificial Sequence
<220> FEATURE:
<223> OTHER INFORMATION: Synthetic primer

<400> SEQUENCE: 12
tccaaatcac acctctccag gag 23

<210> SEQ ID NO 13
<211> LENGTH: 23
<212> TYPE: DNA
<213> ORGANISM: Artificial Sequence
<220> FEATURE:
<223> OTHER INFORMATION: Synthetic primer

<400> SEQUENCE: 13
acctctcatt tcttgcagtt ccg 23

<210> SEQ ID NO 14
<211> LENGTH: 24
<212> TYPE: DNA
<213> ORGANISM: Artificial Sequence
<220> FEATURE:
<223> OTHER INFORMATION: Synthetic primer

<400> SEQUENCE: 14
caggatggag gtgacattgt agct 24

<210> SEQ ID NO 15
<211> LENGTH: 21
<212> TYPE: DNA
<213> ORGANISM: Artificial Sequence
<220> FEATURE:

<223> OTHER INFORMATION: Synthetic primer

<400> SEQUENCE: 15
agtgtgacgt tgacatccgt a 21

<210> SEQ ID NO 16
<211> LENGTH: 22
<212> TYPE: DNA
<213> ORGANISM: Artificial Sequence
<220> FEATURE:
<223> OTHER INFORMATION: Synthetic primer

<400> SEQUENCE: 16
gccagagcag taatctcctt ct 22

<210> SEQ ID NO 17
<211> LENGTH: 20
<212> TYPE: DNA
<213> ORGANISM: Artificial Sequence
<220> FEATURE:
<223> OTHER INFORMATION: Synthetic primer

<400> SEQUENCE: 17
tgacagtggg ctgtttgttc 20

<210> SEQ ID NO 18
<211> LENGTH: 20
<212> TYPE: DNA
<213> ORGANISM: Artificial Sequence
<220> FEATURE:
<223> OTHER INFORMATION: Synthetic primer

<400> SEQUENCE: 18
aagaccccaa gtgcctttct 20

<210> SEQ ID NO 19
<211> LENGTH: 20
<212> TYPE: DNA
<213> ORGANISM: Artificial Sequence
<220> FEATURE:
<223> OTHER INFORMATION: Synthetic primer

<400> SEQUENCE: 19
tttcaaggat gctggctctt 20

<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20
ggcctcagct tgtcaaattc 20

<210> SEQ ID NO 21
<211> LENGTH: 21
<212> TYPE: DNA
<213> ORGANISM: Artificial Sequence
<220> FEATURE:
<223> OTHER INFORMATION: Synthetic primer

<400> SEQUENCE: 21
aaggtgaagg tcggagtcaa c 21

-continued

```
<210> SEQ ID NO 22
<211> LENGTH: 22
<212> TYPE: DNA
<213> ORGANISM: Artificial Sequence
<220> FEATURE:
<223> OTHER INFORMATION: Synthetic primer

<400> SEQUENCE: 22

ggggtcattg atggcaacaa ta                                              22
```

KITS FOR DETECTING AND MONITORING ENDOCRINE DISRUPTING CHEMICALS (EDCS)

CROSS REFERENCE TO RELATED APPLICATION(S)

This application claims the benefit of the earlier filing date of U.S. provisional application No. 61/656,473, filed Jun. 6, 2012, and the entire content thereof is incorporated herein by reference in its entirety.

FIELD

This disclosure relates to methods, systems and kits for monitoring, detecting and/or measuring chemicals, such as endocrine disruptor chemicals, in environmental samples. This disclosure further relates to genetically engineered constructs that encode traceable fusion proteins that translocate from the cytoplasm to the nucleus in the presence of an endocrine disrupting chemical, and mammalian cells expressing one or more of such constructs.

BACKGROUND

An endocrine disruptor chemical (EDC) is an exogenous substance that impacts at least one function of an animal's endocrine system and consequently causes adverse health effects in an intact organism, its progeny, or (sub)populations. EDCs can cause adverse biological effects in animals and humans (Diamanti-Kandarakis et al., *Horm. Metab Res* 42:543-552, 2010).

Contamination of the environment, particularly water sources, with EDCs is a major concern for human health and threatens the integrity of aquatic ecosystems (Diamanti-Kandarakis et al., *Endocr. Rev.* 30:293-342, 2009; Deblonde et al., *Int. J. Hyg. Environ. Health* 214:442-448, 2011). Harmful effects of synthetic progestogens (Zeilinger et al., *Environ. Toxicol. Chem.* 28:2663-2670, 2009; Paulos et al., *Aquat. Toxicol.* 99:256-262, 2010) and especially of estrogenic water contaminants (Iwanowicz et al., *Environ. Toxicol. Chem.* 28:1072-1083, 2009; Alvarez et al., *Environ. Toxicol. Chem.* 28:1084-1095, 2009; Caldwell et al., *Environ. Sci. Technol.* 42:7046-7054, 2008; Lange et al., *Environ. Toxicol. Chem.* 20:1216-1227, 2001; Blazer et al., *Environ. Monit. Assess.* DOI 10.1007/s10661-011-2266-5, 2011) on fish reproduction are well documented. In addition, there is growing concern that environmental contamination with EDCs has deleterious effects on human reproduction, breast development and cancer, prostate cancer, neuroendocrinology, thyroid metabolism and obesity, and cardiovascular endocrinology (Diamanti-Kandarakis et al., *Endocr. Rev.* 30:293-342, 2009).

Glucocorticoids act through the glucocorticoid and mineralocorticoids receptors (GR and MR, respectively). Glucocorticoid deficiency is associated with a number of complex symptoms and is a life-threatening condition (Arlt & Allolio, *Lancet* 361:1881-1893, 2003). Naturally occurring glucocorticoids are released in mammalian organisms during the circadian cycle. However, excess exposure to glucocorticoids is associated with immune suppression and variety of other deleterious side effects (Schacke et al., *Pharmacol. Ther.* 96:23-43, 2002). Unoccupied glucocorticoid receptor resides in the cytoplasm and is bound to various heat-shock proteins and immunophilins in a large multi-protein complex (Pratt & Toft, *Endocr. Rev.* 18:306-360, 1997; Pratt et al., *Handb. Exp. Pharmacol.* 172:111-138, 2006). Upon hormone binding, GR dissociates from the chaperones and translocates to the cell nucleus, where it interacts with GR regulatory elements (GREs) and elicits GR-specific transcription regulation (John et al., *Mol. Cell.* 29:611-624, 2008).

At present, nothing is known about the prevalence of GCs activity in US water sources. However, using chemical methods, a few reports on water contamination in the Netherlands and China have demonstrated detectable levels of glucocorticoids (Schriks et al., *Environ. Sci. Technol.* 44:4766-4774, 2010; Change et al., *Environ. Sci. Technol.* 41:3462-3468, 2007). Another recent study has demonstrated that environmentally relevant concentrations of synthetic GCs have deleterious effects on fish (Kugathas & Sumpter, *Environ. Sci. Technol.* 45:2377-2383, 2011). The anti-inflammatory properties of the glucocorticoids make them highly prescribed pharmaceuticals. They could readily enter water sources and there are few sparse reports on water contamination with glucocorticoids (Schriks et al., *Environ. Sci. Technol.* 44:4766-4774, 2010; Chang et al., *Environ. Sci. Technol.* 41:3462-3468, 2007). Moreover, waste water treatment plants (WWTP) are not capable of efficiently removing glucocorticoids; it is well documented that anti-inflammatory chemicals are among the most resistant to treatment (30-40% of removal rate).

In spite of their importance, the levels of EDCs, such as steroidal EDCs, in the environment currently are not efficiently monitored and/or regulated. One of the reasons is that no high-throughput, reliable, low-cost detection methods exist for monitoring of biologically active EDCs. Current EDC detection relies on chemical analysis techniques (e.g., mass spectrometry, HPLC, GC, and other purely chemical analytical procedures), in vitro biologically-based but cell-free analysis techniques (e.g., purified receptor binding assays and immunoaffinity chromatography), in vitro cell-based analyses (e.g., cell proliferation assays and receptor-dependent gene expression assays, in human cells, or engineered yeast or bacterial cells), and in vivo analyses (e.g., uterotrophic and other growth/development assays in live rats or other animals). It is crucial to develop and implement novel high-throughput and low-cost methods for detection of EDCs in the environment. The need of such methods is well recognized in the field (Roy et al., *J. Exp. Biol.* 43:975-992, 2005). Existing methods for EDC detection may be sensitive, and in some instances are specific for individual ligands, but in general they are expensive, time-consuming, and largely incompatible with a large-scale sample testing.

SUMMARY

Described herein are methods, systems and kits for monitoring, detecting and/or measuring EDCs in environmental samples. These methods, systems and kits employ live mammalian (for instance, human) cells engineered to express at least one traceable fusion protein that changes its sub-cellular localization, for example translocates from the cytoplasm to the nucleus of the cell in the presence of an EDC. Specifically provided are cells and kits that detect more than one EDC, more than one class of EDC, and in some examples an array of EDCs simultaneously. Also provided are methods, systems and kits tailored for high throughput detection (and optionally quantification) of EDCs in environmental samples, such as water samples.

Provided herein in a first set of embodiments are systems for detecting or quantifying a ligand (e.g., an agonist or an antagonist) of a superfamily receptor protein in an environmental sample. In examples thereof, the system comprises a first mammalian cell expressing a first traceable fusion protein; a second mammalian cell expressing a second traceable fusion protein; and a detection system for the detection of the cytoplasm-to-nuclear translocation of the marker proteins, wherein the first and second traceable fusion proteins independently comprise either: (1) a superfamily receptor protein, and a marker protein domain; or (2) the cytoplasmic/nuclear translocation domain of glucocorticoid receptor, the ligand binding domain of a superfamily receptor protein, and a marker protein domain. Optionally, the mammalian cells are human cells.

Also described are systems for detecting or quantifying a ligand of a superfamily receptor protein in an environmental sample, wherein the ligand for the first or second traceable fusion protein is a natural ligand for the superfamily receptor protein of the traceable fusion protein, or a natural or synthetic compound that binds competitively therewith.

Also provided are systems for detecting or quantifying a ligand of a superfamily receptor protein in an environmental sample that additionally comprise one or more compounds and/or compositions that stably associate with a traceable fusion protein in the absence of a ligand for the ligand binding domain of the traceable fusion protein, and which dissociates from the fusion protein in the presence of a ligand for the ligand binding domain of the traceable fusion protein.

The systems described herein are optionally provided as kits.

Also described are methods for detecting or quantifying an endocrine disruptor chemical (EDC) ligand in an environmental sample, which methods involve contacting with the environmental sample a human cell expressing in its cytoplasm a fusion protein comprising: a receptor for the ligand, which receptor translocates from the cytoplasm to the nucleus upon ligand binding; and a marker protein domain; and then detecting cytoplasmic to nuclear translocation of the fusion protein in response to a ligand of the ligand binding domain in the water sample.

Additional described methods of determining the concentration of an endocrine disruptor chemical (EDC) ligand in an environmental sample involve contacting with the environmental sample a population of eukaryotic cells expressing in their cytoplasm a fusion protein comprising: a receptor for the ligand, which receptor translocates from the cytoplasm to the nucleus upon ligand binding; and a marker protein domain; and scanning one or more test cell(s) to obtain signal data from the marker of the fusion protein; converting the signal data to obtain the cellular location of the labeled protein in the test cell(s); and analyzing the signal data using an analysis system having an algorithm to calculate changes in distribution of the labeled fusion protein between the cytoplasm and the nucleus of the test cell(s), the analysis system having the capability of providing an accurate reading of the concentration of the ligand.

In any of the systems, kits, and methods described herein, the environmental sample can include a water sample, soil sample, or air sample. By way of example, where the environmental sample comprises a water sample, the sample includes in various embodiments one or more of surface water, sub-surface (ground) water, rain, run-off, well water, spring water, drinking water (processed or not), river water, estuary water, ocean water, effluent, treated sewage or untreated sewage.

The foregoing and other objects, features, and advantages of the invention will become more apparent from the following detailed description, which proceeds with reference to the accompanying figures.

BRIEF DESCRIPTION OF THE DRAWINGS

At least some of the figures submitted herewith are provided in full or part color.

FIG. 1A is a schematic representation of the GFP-tagged GR and AR receptor translocation in response to corresponding hormonal treatment. FIG. 1B is a series of micrographs showing GFP-GR translocation in a mammalian cell line (Walker et al., *Methods* (*Comp. to Meth. Enzym.*) 19:386-393, 1999) upon stimulation with dexamethasone for 30 minutes. Nuclei are stained with DAPI. Scale bar, 5 μm. FIG. 1C illustrates transcriptional activation of the GR-regulated Per1 gene by 10 water samples collected using a polar organic chemical integrative sampler (POCIS) are compared to transactivation induced by corticosterone. Data is normalized to DMSO alone. Blank and SS83 are POCIS negative controls. Error bars represent the mean±s.e.m., n=3. One of the water samples, SS97, induces complete GFP-GR translocation (image) and transcriptional activation of Per1 gene at a level higher than the activation induced by 100 nM corticosterone (graph). Scale bar, 5 μm. FIG. 1D is a GC/MS total ion chromatogram of HPLC fractionated sample SS97 (fraction 74-A), which revealed the presence of a complex mixture of volatile hydrocarbons, as indicated by the peaks. Database searching of the extracted MS spectra corresponding to peaks 1-3 showed structural similarity to known androstane-type steroids. GC/MS analysis of these peaks is presented in FIG. 3 and Table 3. FIG. 1E is a series of representative images of GFP-AR nuclear translocation in response to 100 nM of testosterone, androst-4-ene-3,6-dione, and sample SS97 (100×). Scale bar, 5 μm.

FIG. 2A illustrates the geographic locations of the collection sites of the first sample set collected by POCIS. One of the samples (marked with red, SS97) tested positive for GFP-GR translocation, suggesting a presence of glucocorticoid activity. Negative samples are marked with green. FIG. 2B shows GFP-GR translocation in a mammalian cell line (Walker et al., *Methods* (*Comp. to Meth. Enzym.*) 19:386-393, 1999) upon stimulation with 100 nM corticosterone for 30 min. Nuclei are stained with DAPI. Scale bar, 5 μm. FIG. 2C is a series of micrographs illustrating testing of HPLC fractions of sample SS97 (Fractions A-K) for GFP-GR translocation to determine the presence of glucocorticoid activity. Four of 11 fractions tested positive for GFP-GR translocation (FIG. 2C). Because GC/MS analyses detected atrazine in sample SS97, we included it in our analysis (bottom right). However, atrazine did not induce GFP-GR translocation.

FIG. 4A-E illustrates water sample screening by high throughput automated image analysis. FIG. 4A contains examples of images scored for cytoplasmic and nuclear segmentation from control and corticosterone treated 3617 cells. FIG. 4B is an illustration of a workflow for image-based screening of environmental contaminants with glucocorticoid activity using the Perkin Elmer Opera Image Screening System. FIG. 4C illustrates the automated image analysis output for a representative experiment. In this series, eight water samples from a total of 69 (well positions 2B, 2G, 3F, 4F, 9H, 10A, 10C, and 10E corresponding to samples R4E, R4A, R16W, R27, LF1a, 2a, 3a, and 4a (FIG. 4D) tested positive for GFP-GR translocation as indicated by color changes. Wells 1A-D represent four negative (DMSO) controls. Wells 1E-H are positive controls for cells treated with 100 nM corticosterone, and wells 10D, 10F and 10H are positive controls for cells treated with 100 nM dexamethasone. FIG. 4D and FIG. 4E are bar graphs illustrating quantitative analysis for GFP-GR and GFP-AR nuclear translocation, respectively. Translocation was calculated as a ratio of the nuclear versus cytoplasmic intensity, and each value was normalized to the control. Samples positive for glucocorticoid activity are marked with asterisks ($P<0.01$, red asterisks and $P<0.05$, black asterisks). Error bars represent the mean value±s.e.m, n=4.

FIG. 5A is a bar graph illustrating that GFP-GR translocates to the nucleus in a concentration-dependent manner upon treatment with known concentrations of hydrocortisone, dexamethasone, or corticosterone. An algorithm for cytoplasm and nuclear segmentation of the cells was used to determine the mean GFP-GR intensity in both compartments and translocation was quantified as a ratio of these intensities. Each value was normalized to the control sample. Error bars represent the mean value±s.e.m, n=6 ($P<0.05$, asterisks). FIG. 5B is a bar graph illustrating that GFP-AR translocation in response to known concentrations of testosterone. Insert shows that testosterone concentrations as low as 0.1 nM induced a statistically significant increase in the GFP-AR translocation. Samples with $P<0.05$ are indicated by an asterisk. Error bars represent the mean value±s.e.m, n=6. FIG. 5C is a bar graph illustrating that androst-4-en-3,6-dione induces concentration-dependent translocation of the GFP-AR construct ($P<0.05$, asterisks). Error bars represent the mean value±s.e.m, n=6.

FIG. 6A is an image analysis plate map showing a portion of GFP-GR expressing cells plated on a 384 well plate. Twenty two samples out of 38 (58%) tested positive for GFP-GR nuclear translocation. Wells 10A-H are negative controls (DMSO). Wells 1A-H and 9D, 9F, 9H are positive controls treated with 100 nM corticosterone and 100 nM dexamethasone, respectively. FIG. 6B is a bar graph GFP-GR nuclear translocation results summary. All samples in the gray box are POCIS negative controls. Positive samples are marked with asterisks ($P<0.01$, red asterisks and $P<0.05$, black asterisks). Error bars represent the mean value±s.e.m, n=4.

FIG. 7A is an image analysis plate map showing a portion of GFP-AR expressing cells plated on a 384 well plate. Twenty one samples out of 40 (55%) tested positive for GFP-AR nuclear translocation. Wells 10A-H are negative controls (DMSO). Wells 1A-H are positive controls for cells treated with 100 nM testosterone. FIG. 7B is a bar graph GFP-AR nuclear translocation results summary. All samples in the gray box are POCIS negative controls. Positive samples are marked with asterisks ($P<0.01$, red asterisks and $P<0.05$, black asterisks). Error bars represent the mean value±s.e.m, n=4.

FIG. 9A and FIG. 9B are bar graphs illustrating concentration-dependent GFP-GRand GFP-AR translocation for sample SS97 four years after the initial collection. Translocation is calculated from the automatic image analysis and expressed as a ratio of nuclear versus cytoplasmic intensity normalized to DMSO treated control. Samples positive for glucocorticoid and androgen activities are marked with asterisks ($P<0.05$). Error bars represent the mean value±s.e.m, n=4. Significant increase in the GFP-GR translocation is detectable in 1× dilution for this sample (inset). While the lowest concentration inducing significant GFP-AR translocation was 10× (B, insert). FIG. 9C shows a representative heat-map for concentration-dependent GFP-GR translocation indicated as nuclear versus cytoplasmic intensity. Dex (dexamethasone, 100 nM), Cst (corticosterone, 100 nM), and HC (hydrocortisone, 100 nM) are included as positive controls as indicated on the bar graph above (FIG. 9A). FIG. 9D is a representative heat-map for the concentration-dependent GFP-AR translocation. Testosterone (Testo, 100 nM) was included as a positive control, as indicated on the bar graph above (FIG. 9B). FIG. 9E is a pair of bar graphs illustrating concentration-dependent transcriptional activation of the GR-regulated genes, Tgm2 and Lcn2. All tested concentrations (including 1×) induced transcriptional responses of both genes, presented as fold change from the vehicle (DMSO) treated control. Dex (dexamethasone, 100 nM), Cst (corticosterone, 100 nM), and HC (hydrocortisone, 100 nM) are included as positive controls. Error bars represent the mean±s.e.m, n=4. FIG. 4F is a pair of bar graphs illustrating concentration-dependent transcriptional activation of the AR-regulated genes, NKX2.1 and RHOU by sample SS7 in LNCaP cells. Gene transcription was induced by the concentrations 10×, 20×, and 50× ($P<0.05$, asterisks), whereas higher concentrations seemed to have an inhibitory activity. Data is presented as fold change in comparison to the vehicle (DMSO) treated control. Androst-4-en-3,6-dione (A-4) (100 nM) and testosterone (Testo, 100 nM) were included as positive controls. Error bars represent the mean±s.e.m, n=4.

FIG. 10A is a series of representative images for the concentration-dependent GFP-GR translocation in response to known concentrations of the water sample at site SS97. Scale bar, 10 μm. FIG. 10B is a series of representative images for concentration-dependent GFP-AR translocation in response to known concentrations of the water sample at site SS97. Scale bar, 10 μm.

FIG. 11A is a series of representative images for concentration-dependent GFP-GR translocation in response to known concentrations of the water sample at site GL2W. Scale bar, 10 μm. FIG. 11B is a series of representative images for the concentration-dependent GFP-AR translocation in response to known concentrations of the water sample at site GL2W. Scale bar, 10 μm.

FIG. 12A is a bar graph illustrating translocation of GFP-GR in response to newly collected sample from the same location as GL2W (see also FIG. 11A).

Translocation was calculated as a ratio of the nuclear versus cytoplasmic intensity and each value was further normalized to the value for the control sample. Samples positive for GFP-GR translocation are marked with asterisks ($P<0.05$). The lowest concentration inducing GFP-GR translocation is 10×. DMSO negative control, Dex (dexamethasone, 100 nM), Cst (corticosterone, 100 nM), and HC (hydrocortisone, 100 nM) were included as positive controls. Error bars represent the mean value±s.e.m, n=4. FIG. 12B is a representative raw data heat-map for GFP-GR translocation as in panel A. FIG. 12C is a series of bar graphs illustrating concentration-dependent transcriptional activation of three GR-regulated genes induced by newly collected sample from GL2W site. All concentrations induced transcriptional activation of at least one of the GR-regulated genes ($P<0.05$, asterisks). Transcription responses are presented as fold change in comparison to the vehicle control sample (DMSO). Dex (dexamethasone, 100 nM), Cst (corticosterone, 100 nM), and HC (hydrocortisone, 100 nM) are included as positive controls. Error bars represent the mean±s.e.m, n=4.

FIG. 13A is a bar graph illustrating quantification of the GFP-AR concentration-dependent translocation response for the newly collected water sample at the GL2W site (see also FIG. 11B). Translocation was calculated as a ratio of the nuclear versus cytoplasmic intensity and each value was further normalized to the value for the control sample. Samples positive for GFP-AR translocation are marked with asterisks ($P<0.05$). The lowest sample concentration inducing GFP-AR translocation is 10×. Testosterone (Testo, 100 nM) is included as a positive control. Error bars represent the mean value±s.e.m, n=4. FIG. 13B is a representative raw data heat-map for GFP-AR translocation as in panel A. FIG. 13C is a pair of graphs illustrating concentration-dependent transcriptional activation of AR-regulated genes induced by newly collected sample from GL2W site in LNCaP cells which express endogenous AR. Concentrations 10× to 50× induced transcriptional activation in the AR-regulated genes NKX2.1 and RHOU ($P<0.05$, asterisks). At 100× concentration, we observed a reduced NKX2.1 expression, and did not detect change in RHOU transcription, suggesting the presence of an inhibitory activity (possibly anti-androgenic) which is apparent at that concentration. Transcriptional responses are presented as fold change in comparison to the vehicle treated (DMSO) control sample. Androst-4-en-3,6-dione (100 nM) and testosterone (Testo, 100 nM) are included as positive controls. Error bars represent the mean±s.e.m, n=4.

SEQUENCE LISTING

Figure 1A:
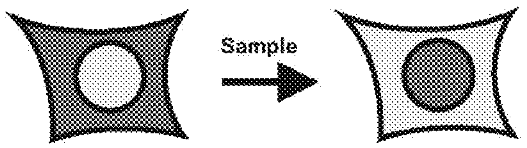
FIG. 1A-E illustrates analysis of water samples for glucocorticoid and androgen contamination.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file named Sequences.txt, created on Jun. 6, 2013, ~58 KB, which is incorporated by reference herein.

SEQ ID NO: 1 is the nucleic acid sequence which encodes traceable fusion protein pCI-nGFP-C656G. The sequence includes the following features at the indicated nucleotide positions:

```
6X His tag (8-24)

HA Tag (28-59)

GFP (60-780)

GA Linker (781-810)

Rat GR (829-3213), containing within it the C656G
mutation (single point mutation T->G, codon changes
from TGC->GGC) (2791; underlined)
ATGGCCCACCATCACCACCATCACGGATATCCATACGACGTGCCAGATTACGCTCAGTCG

AGTGCCATGAGTAAAGGAGAAGAACTTTTCACTGGAGTTGTCCCAATTCTTGTTGAATTA

GATGGTGATGTTAATGGGCACAAATTTTCTGTCAGTGGAGAGGGTGAAGGTGATGCAACA

TACGGAAAACTTACCCTTAAATTTATTTGCACTACTGGAAAACTACCTGTTCCTTGGCCA

ACACTTGTCACTACTTTCACTTATGGTGTTCAATGCTTTTCAAGATACCCAGATCATATG

AAACAGCATGACTTTTTCAAGAGTGCCATGCCCGAAGGTTATGTACAGGAAAGAACTATA

TTTTTCAAAGATGACGGGAACTACAAGACACGTGCTGAAGTCAAGTTTGAAGGTGATACC

CTTGTTAATAGAATCGAGTTAAAAGGTATTGATTTTAAAGAAGATGGAAACATTCTTGGA

CACAAATTGGAATACAACTATAACTCACACAATGTATACATCATGGCAGACAAACAAAAG

AATGGAATCAAAGTTAACTTCAAAATTAGACACAACATTGAAGATGGAAGCGTTCAACTA

GCAGACCATTATCAACAAAATACTCCAATTGGCGATGGCCCTGTCCTTTTACCAGACAAC

CATTACCTGTCCACACAATCTGCCCTTTCGAAAGATCCCAACGAAAAGAGAGACCACATG

GTCCTTCTTGAGTTTGTAACAGCTGCTGGGATTACACATGGCATGGATGAACTATACAAA

GGCGCCGGCGCTGGTGCTGGTGCTGGCGCCATCAGCGCGCTGATCCTGGACTCCAAAGAA
```

-continued

TCCTTAGCTCCCCCTGGTAGAGACGAAGTCCCTGGCAGTTTGCTTGGCCAGGGGAGGGGG

AGCGTAATGGACTTTTATAAAAGCCTGAGGGGAGGAGCTACAGTCAAGGTTTCTGCATCT

TCGCCCTCAGTGGCTGCTGCTTCTCAGGCAGATTCCAAGCAGCAGAGGATTCTCCTTGAT

TTCTCGAAAGGCTCCACAAGCAATGTGCAGCAGCGACAGCAGCAGCAGCAGCAGCAGCAG

CAGCAGCAGCAGCAGCAGCAGCAGCAGCAGCAGCCAGGCTTATCCAAAGCCGTTTCACTG

TCCATGGGGCTGTATATGGGAGAGACAGAAACAAAAGTGATGGGGAATGACTTGGGCTAC

CCACAGCAGGGCCAACTTGGCCTTTCCTCTGGGGAAACAGACTTTCGGCTTCTGGAAGAA

AGCATTGCAAACCTCAATAGGTCGACCAGCGTTCCAGAGAACCCCAAGAGTTCAACGTCT

GCAACTGGGTGTGCTACCCCGACAGAGAAGGAGTTTCCCAAAACTCACTCGGATGCATCT

TCAGAACAGCAAAATCGAAAAAGCCAGACCGGCACCAACGGAGGCAGTGTGAAATTGTAT

CCCACAGACCAAAGCACCTTTGACCTCTTGAAGGATTTGGAGTTTTCCGCTGGGTCCCCA

AGTAAAGACACAAACGAGAGTCCCTGGAGATCAGATCTGTTGATAGATGAAAACTTGCTT

TCTCCTTTGGCGGGAGAAGATGATCCATTCCTTCTCGAAGGGAACACGAATGAGGATTGT

AAGCCTCTTATTTTACCGGACACTAAACCTAAAATTAAGGATACTGGAGATACAATCTTA

TCAAGTCCCAGCAGTGTGGCACTACCCCAAGTGAAAACAGAAAAAGATGATTTCATTGAA

CTTTGCACCCCCGGGGTAATTAAGCAAGAGAAACTGGGCCCAGTTTATTGTCAGGCAAGC

TTTTCTGGGACAAATATAATTGGTAATAAAATGTCTGCCATTTCTGTTCATGGTGTGAGT

ACCTCTGGAGGACAGATGTACCACTATGACATGAATACAGCATCCCTTTCTCAGCAGCAG

GATCAGAAGCCTGTTTTTAATGTCATTCCACCAATTCCTGTTGGTTCTGAAAACTGGAAT

AGGTGCCAAGGCTCCGGAGAGGACAGCCTGACTTCCTTGGGGGCTCTGAACTTCCCAGGC

CGGTCAGTGTTTTCTAATGGGTACTCAAGCCCTGGAATGAGACCAGATGTAAGCTCTCCT

CCATCCAGCTCGTCAGCAGCCACGGGACCACCTCCCAAGCTCTGCCTGGTGTGCTCCGAT

GAAGCTTCAGGATGTCATTACGGGGTGCTGACATGTGGAAGCTGCAAAGTATTCTTTAAA

AGAGCAGTGGAAGGACAGCACAATTACCTTTGTGCTGGAAGAAACGATTGCATCATTGAT

AAAATTCGAAGGAAAAACTGCCCAGCATGCCGCTATCGGAAATGTCTTCAGGCTGGAATG

AACCTTGAAGCTCGAAAAACAAAGAAAAAAATCAAAGGGATTCAGCAAGCCACTGCAGGA

GTCTCACAAGACACTTCGGAAAATCCTAACAAAACAATAGTTCCTGCAGCATTACCACAG

CTCACCCCTACCTTGGTGTCACTGCTGGAGGTGATTGAACCCGAGGTGTTGTATGCAGGA

TATGATAGCTCTGTTCCAGATTCAGCATGGAGAATTATGACCACACTCAACATGTTAGGT

GGGCGTCAAGTGATTGCAGCAGTGAAATGGGCAAAGGCGATACTAGGCTTGAGAAACTTA

CACCTCGATGACCAAATGACCCTGCTACAGTACTCATGGATGTTTCTCATGGCATTTGCC

TTGGGTTGGAGATCATACAGACAATCAAGCGGAAACCTGCTCTGCTTTGCTCCTGATCTG

ATTATTAATGAGCAGAGAATGTCTCTACCCGGCATGTATGACCAATGTAAACACATGCTG

TTTGTCTCCTCTGAATTACAAAGATTGCAGGTATCCTATGAAGAGTATCTCTGTATGAAA

ACCTTACTGCTTCTCTCCTCAGTTCCTAAGGAAGGTCTGAAGAGCCAAGAGTTATTTGAT

GAGATTCGAATGACTTATATCAAAGAGCTAGGAAAAGCCATCGTCAAAAGGGAAGGGAAC

TCCAGTCAGAACTGGCAACGGTTTTACCAACTGACAAAGCTTCTGGACTCCATGCATGAG

GTGGTTGAGAATCTCCTTACCTACTGCTTCCAGACATTTTTGGATAAGACCATGAGTATT

GAATTCCCAGAGATGTTAGCTGAAATCATCACTAATCAGATACCAAAATATTCAAATGGA

AATATCAAAAAGCTTCTGTTTCATCAAAAATGA

SEQ ID NO: 2 is the amino acid sequence of traceable fusion protein pCI-nGFP-C656G. The sequence includes the following features at the indicated amino acid positions:

```
6X His tag (3-8)

HA Tag (10-18)

GFP (23-260)

GA Linker (261-270)

Rat GR (277-1070)

C656G mutation (Cysteine to Glycine) (931; underlined)
MAHHHHHHGYPYDVPDYAQSSAMSKGEELFTGVVPILVELDGDVNGHKFSVSGEGEGDAT

YGKLTLKFICTTGKLPVPWPTLVTTFTYGVQCFSRYPDHMKQHDFFKSAMPEGYVQERTI

FFKDDGNYKTRAEVKFEGDTLVNRIELKGIDFKEDGNILGHKLEYNYNSHNVYIMADKQK

NGIKVNFKIRHNIEDGSVQLADHYQQNTPIGDGPVLLPDNHYLSTQSALSKDPNEKRDHM

VLLEFVTAAGITHGMDELYKGAGAGAGAGAISALILDSKESLAPPGRDEVPGSLLGQGRG

SVMDFYKSLRGGATVKVSASSPSVAAASQADSKQQRILLDFSKGSTSNVQQRQQQQQQQQ

QQQQQQQQQQQPGLSKAVSLSMGLYMGETETKVMGNDLGYPQQGQLGLSSGETDFRLLEE

SIANLNRSTSVPENPKSSTSATGCATPTEKEFPKTHSDASSEQQNRKSQTGTNGGSVKLY

PTDQSTFDLLKDLEFSAGSPSKDTNESPWRSDLLIDENLLSPLAGEDDPFLLEGNTNEDC

KPLILPDTKPKIKDTGDTILSSPSSVALPQVKTEKDDFIELCTPGVIKQEKLGPVYCQAS

FSGTNIIGNKMSAISVHGVSTSGGQMYHYDMNTASLSQQQDQKPVFNVIPPIPVGSENWN

RCQGSGEDSLTSLGALNFPGRSVFSNGYSSPGMRPDVSSPPSSSSAATGPPPKLCLVCSD

EASGCHYGVLTCGSCKVFFKRAVEGQHNYLCAGRNDCIIDKIRRKNCPACRYRKCLQAGM

NLEARKTKKKIKGIQQATAGVSQDTSENPNKTIVPAALPQLTPTLVSLLEVIEPEVLYAG

YDSSVPDSAWRIMTTLNMLGGRQVIAAVKWAKAILGLRNLHLDDQMTLLQYSWMFLMAFA

LGWRSYRQSSGNLLCFAPDLIINEQRMSLPGMYDQCKHMLFVSSELQRLQVSYEEYLCMK

TLLLLSSVPKEGLKSQELFDEIRMTYIKELGKAIVKREGNSSQNWQRFYQLTKLLDSMHE

VVENLLTYCFQTFLDKTMSIEFPEMLAEIITNQIPKYSNGNIKKLLFHQK*
```

SEQ ID NO: 3 is the nucleic acid sequence which encodes traceable fusion protein eGFP-hAR. The sequence includes the following features at the indicated nucleotide positions:

```
EGFP (1-717)

Vector polylinker (718-752

hAR (753-3516)

ATGGTGAGCAAGGGCGAGGAGCTGTTCACCGGGGTGGTGCCCATCCTGGTCGAGCTGGAC

GGCGACGTAAACGGCCACAAGTTCAGCGTGTCCGGCGAGGGCGAGGGCGATGCCACCTAC

GGCAAGCTGACCCTGAAGTTCATCTGCACCACCGGCAAGCTGCCCGTGCCCTGGCCCACC

CTCGTGACCACCCTGACCTACGGCGTGCAGTGCTTCAGCCGCTACCCCGACCACATGAAG

CAGCACGACTTCTTCAAGTCCGCCATGCCCGAAGGCTACGTCCAGGAGCGCACCATCTTC

TTCAAGGACGACGGCAACTACAAGACCCGCGCCGAGGTGAAGTTCGAGGGCGACACCCTG

GTGAACCGCATCGAGCTGAAGGGCATCGACTTCAAGGAGGACGGCAACATCCTGGGGCAC

AAGCTGGAGTACAACTACAACAGCCACAACGTCTATATCATGGCCGACAAGCAGAAGAAC

GGCATCAAGGTGAACTTCAAGATCCGCCACAACATCGAGGACGGCAGCGTGCAGCTCGCC
```

-continued

GACCACTACCAGCAGAACACCCCCATCGGCGACGGCCCCGTGCTGCTGCCCGACAACCAC

TACCTGAGCACCCAGTCCGCCCTGAGCAAAGACCCCAACGAGAAGCGCGATCACATGGTC

CTGCTGGAGTTCGTGACCGCCGCCGGGATCACTCTCGGCATGGACGAGCTGTACAAGTCC

GGACTCAGATCTCGAGCTCAAGCTTCGAATTCGATGGAAGTGCAGTTAGGGCTGGGAAGG

GTCTACCCTCGGCCGCCGTCCAAGACCTACCGAGGAGCTTTCCAGAATCTGTTCCAGAGC

GTGCGCGAAGTGATCCAGAACCCGGGCCCCAGGCACCCAGAGGCCGCGAGCGCAGCACCT

CCCGGCGCCAGTTTGCTGCTGCTGCAGCAGCAGCAGCAGCAGCAGCAGCAGCAGCAGCAG

CAGCAGCAGCAGCAGCAGCAGCAGCAGCAGCAAGAGACTAGCCCCAGGCAGCAGCAGCAG

CAGCAGGGTGAGGATGGTTCTCCCCAAGCCCATCGTAGAGGCCCCACAGGCTACCTGGTC

CTGGATGAGGAACAGCAACCTTCACAGCCGCAGTCGGCCCTGGAGTGCCACCCCGAGAGA

GGTTGCGTCCCAGAGCCTGGAGCCGCCGTGGCCGCCAGCAAGGGGCTGCCGCAGCAGCTG

CCAGCACCTCCGGACGAGGATGACTCAGCTGCCCCATCCACGTTGTCCCTGCTGGGCCCC

ACTTTCCCCGGCTTAAGCAGCTGCTCCGCTGACCTTAAAGACATCCTGAGCGAGGCCAGC

ACCATGCAACTCCTTCAGCAACAGCAGCAGGAAGCAGTATCCGAAGGCAGCAGCAGCGGG

AGAGCGAGGGAGGCCTCGGGGGCTCCCACTTCCTCCAAGGACAATTACTTAGGGGGCACT

TCGACCATTTCTGACAACGCCAAGGAGTTGTGTAAGGCAGTGTCGGTGTCCATGGGCCTG

GGTGTGGAGGCGTTGGAGCATCTGAGTCCAGGGGAACAGCTTCGGGGGGATTGCATGTAC

GCCCCACTTTTGGGAGTTCCACCCGCTGTGCGTCCCACTCCTTGTGCCCCATTGGCCGAA

TGCAAAGGTTCTCTGCTAGACGACAGCGCAGGCAAGAGCACTGAAGATACTGCTGAGTAT

TCCCCTTTCAAGGGAGGTTACACCAAAGGGCTAGAAGGCGAGAGCCTAGGCTGCTCTGGC

AGCGCTGCAGCAGGGAGCTCCGGGACACTTGAACTGCCGTCTACCCTGTCTCTCTACAAG

TCCGGAGCACTGGACGAGGCAGCTGCGTACCAGAGTCGCGACTACTACAACTTTCCACTG

GCTCTGGCCGGACCGCCGCCCCCTCCGCCGCCTCCCCATCCCCACGCTCGCATCAAGCTG

GAGAACCCGCTGGACTACGGCAGCGCCTGGGCGGCTGCGGCGGCGCAGTGCCGCTATGGG

GACCTGGCGAGCCTGCATGGCGCGGGTGCAGCGGGACCCGGTTCTGGGTCACCCTCAGCC

GCCGCTTCCTCATCCTGGCACACTCTCTTCACAGCCGAAGAAGGCCAGTTGTATGGACCG

TGTGGTGGTGGTGGGGGTGGTGGCGGCGGCGGCGGCGGCGGCGGCGGCGGCGGCGGCGGC

GGCGGCGGCGGCGAGGCGGGAGCTGTAGCCCCCTACGGCTACACTCGGCCCCCTCAGGGG

CTGGCGGGCCAGGAAAGCGACTTCACCGCACCTGATGTGTGGTACCCTGGCGGCATGGTG

AGCAGAGTGCCCTATCCCAGTCCCACTTGTGTCAAAAGCGAAATGGGCCCCTGGATGGAT

AGCTACTCCGGACCTTACGGGGACATGCGTTTGGAGACTGCCAGGGACCATGTTTTGCCC

ATTGACTATTACTTTCCACCCCAGAAGACCTGCCTGATCTGTGGAGATGAAGCTTCTGGG

TGTCACTATGGAGCTCTCACATGTGGAAGCTGCAAGGTCTTCTTCAAAAGAGCCGCTGAA

GGGAAACAGAAGTACCTGTGCGCCAGCAGAAATGATTGCACTATTGATAAATTCCGAAGG

AAAAATTGTCCATCTTGTCGTCTTCGGAAATGTTATGAAGCAGGGATGACTCTGGGAGCC

CGGAAGCTGAAGAAACTTGGTAATCTGAAACTACAGGAGGAAGGAGAGGCTTCCAGCACC

ACCAGCCCCACTGAGGAGACAACCCAGAAGCTGACAGTGTCACACATTGAAGGCTATGAA

TGTCAGCCCATCTTTCTGAATGTCCTGGAAGCCATTGAGCCAGGTGTAGTGTGTGCTGGA

CACGACAACAACCAGCCCGACTCCTTTGCAGCCTTGCTCTCTAGCCTCAATGAACTGGGA

GAGAGACAGCTTGTACACGTGGTCAAGTGGGCCAAGGCCTTGCCTGGCTTCCGCAACTTA

-continued

CACGTGGACGACCAGATGGCTGTCATTCAGTACTCCTGGATGGGGCTCATGGTGTTTGCC

ATGGGCTGGCGATCCTTCACCAATGTCAACTCCAGGATGCTCTACTTCGCCCCTGATCTG

GTTTTCAATGAGTACCGCATGCACAAGTCCCGGATGTACAGCCAGTGTGTCCGAATGAGG

CACCTCTCTCAAGAGTTTGGATGGCTCCAAATCACCCCCCAGGAATTCCTGTGCATGAAA

GCACTGCTACTCTTCAGCATTATTCCAGTGGATGGGCTGAAAAATCAAAAATTCTTTGAT

GAACTTCGAATGAACTACATCAAGGAACTCGATCGTATCATTGCATGCAAAAGAAAAAAT

CCCACATCCTGCTCAAGACGCTTCTACCAGCTCACCAAGCTCCTGGACTCCGTGCAGCCT

ATTGCGAGAGAGCTGCATCAGTTCACTTTTGACCTGCTAATCAAGTCACACATGGTGAGC

GTGGACTTTCCGGAAATGATGGCAGAGATCATCTCTGTGCAAGTGCCCAAGATCCTTTCT

GGGAAAGTCAAGCCCATCTATTTCCACACCCAGTGA

SEQ ID NO: 4 is the amino acid sequence of traceable fusion protein eGFP-hAR. The sequence includes the following features at the indicated amino acid positions:

EGFP (1-239)

Vector polylinker (240-251)

hAR (252-1171)

MVSKGEELFTGVVPILVELDGDVNGHKFSVSGEGEGDATYGKLTLKFICTTGKLPVPWPT

LVTTLTYGVQCFSRYPDHMKQHDFFKSAMPEGYVQERTIFFKDDGNYKTRAEVKFEGDTL

VNRIELKGIDFKEDGNILGHKLEYNYNSHNVYIMADKQKNGIKVNFKIRHNIEDGSVQLA

DHYQQNTPIGDGPVLLPDNHYLSTQSALSKDPNEKRDHMVLLEFVTAAGITLGMDELYKS

GLRSRAQASNSMEVQLGLGRVYPRPPSKTYRGAFQNLFQSVREVIQNPGPRHPEAASAAP

PGASLLLLQQQQQQQQQQQQQQQQQQQQQQQQETSPRQQQQQQGEDGSPQAHRRGPTGYLV

LDEEQQPSQPQSALECHPERGCVPEPGAAVAASKGLPQQLPAPPDEDDSAAPSTLSLLGP

TFPGLSSCSADLKDILSEASTMQLLQQQQQEAVSEGSSSGRAREASGAPTSSKDNYLGGT

STISDNAKELCKAVSVSMGLGVEALEHLSPGEQLRGDCMYAPLLGVPPAVRPTPCAPLAE

CKGSLLDDSAGKSTEDTAEYSPFKGGYTKGLEGESLGCSGSAAAGSSGTLELPSTLSLYK

SGALDEAAAYQSRDYYNFPLALAGPPPPPPPPHPHARIKLENPLDYGSAWAAAAAQCRYG

DLASLHGAGAAGPGSGSPSAAASSSWHTLFTAEEGQLYGPCGGGGGGGGGGGGGGGGGGG

GGGGEAGAVAPYGYTRPPQGLAGQESDFTAPDVWYPGGMVSRVPYPSPTCVKSEMGPWMD

SYSGPYGDMRLETARDHVLPIDYYFPPQKTCLICGDEASGCHYGALTCGSCKVFFKRAAE

GKQKYLCASRNDCTIDKFRRKNCPSCRLRKCYEAGMTLGARKLKKLGNLKLQEEGEASST

TSPTEETTQKLTVSHIEGYECQPIFLNVLEAIEPGVVCAGHDNNQPDSFAALLSSLNELG

ERQLVHVVKWAKALPGFRNLHVDDQMAVIQYSWMGLMVFAMGWRSFTNVNSRMLYFAPDL

VFNEYRMHKSRMYSQCVRMRHLSQEFGWLQITPQEFLCMKALLLFSIIPVDGLKNQKFFD

ELRMNYIKELDRIIACKRKNPTSCSRRFYQLTKLLDSVQPIARELHQFTFDLLIKSHMVS

VDFPEMMAEIISVQVPKILSGKVKPIYFHTQ*

SEQ ID NO: 5 is the nucleic acid sequence which encodes traceable fusion protein eGFP-GR-ER310. The sequence includes the following features at the indicated nucleotide positions:

EGFP (1-717)

GA Linker (718-747)

hGR (748-2400)

hER (2401-3261)

ATGGTGAGCAAGGGCGAGGAGCTGTTCACCGGGGTGGTGCCCATCCTGGTCGAGCTGGAC

GGCGACGTAAACGGCCACAAGTTCAGCGTGTCCGGCGAGGGCGAGGGCGATGCCACCTAC

GGCAAGCTGACCCTGAAGTTCATCTGCACCACCGGCAAGCTGCCCGTGCCCTGGCCCACC

CTCGTGACCACCCTGACCTACGGCGTGCAGTGCTTCAGCCGCTACCCCGACCACATGAAG

CAGCACGACTTCTTCAAGTCCGCCATGCCCGAAGGCTACGTCCAGGAGCGCACCATCTTC

TTCAAGGACGACGGCAACTACAAGACCCGCGCCGAGGTGAAGTTCGAGGGCGACACCCTG

GTGAACCGCATCGAGCTGAAGGGCATCGACTTCAAGGAGGACGGCAACATCCTGGGGCAC

AAGCTGGAGTACAACTACAACAGCCACAACGTCTATATCATGGCCGACAAGCAGAAGAAC

GGCATCAAGGTGAACTTCAAGATCCGCCACAACATCGAGGACGGCAGCGTGCAGCTCGCC

GACCACTACCAGCAGAACACCCCCATCGGCGACGGCCCCGTGCTGCTGCCCGACAACCAC

TACCTGAGCACCCAGTCCGCCCTGAGCAAAGACCCCAACGAGAAGCGCGATCACATGGTC

CTGCTGGAGTTCGTGACCGCCGCCGGGATCACTCTCGGCATGGACGAGCTGTACAAGGGC

GCTGGAGCAGGGGCTGGAGCCGGAGCTGACTCCAAAGAATCATTAACTCCTGGTAGAGAA

GAAAACCCCAGCAGTGTGCTTGCTCAGGAGAGGGGAGATGTGATGGACTTCTATAAAACC

CTAAGAGGAGGAGCTACTGTGAAGGTTTCTGCGTCTTCACCCTCACTGGCTGTCGCTTCT

CAATCAGACTCCAAGCAGCGAAGACTTTTGGTTGATTTTCCAAAAGGCTCAGTAAGCAAT

GCGCAGCAGCCAGATCTGTCCAAAGCAGTTTCACTCTCAATGGGACTGTATATGGGAGAG

ACAGAAACAAAAGTGATGGGAAATGACCTGGGATTCCCACAGCAGGGCCAAATCAGCCTT

TCCTCGGGGGAAACAGACTTAAAGCTTTTGGAAGAAAGCATTGCAAACCTCAATAGGTCG

ACCAGTGTTCCAGAGAACCCCAAGAGTTCAGCATCCACTGCTGTGTCTGCTGCCCCCACA

GAGAAGGAGTTTCCAAAAACTCACTCTGATGTATCTTCAGAACAGCAACATTTGAAGGGC

CAGACTGGCACCAACGGTGGCAATGTGAAATTGTATACCACAGACCAAAGCACCTTTGAC

ATTTTGCAGGATTTGGAGTTTTCTTCTGGGTCCCCAGGTAAAGAGACGAATGAGAGTCCT

TGGAGATCAGACCTGTTGATAGATGAAAACTGTTTGCTTTCTCCTCTGGCGGGAGAAGAC

GATTCATTCCTTTTGGAAGGAAACTCGAATGAGGACTGCAAGCCTCTCATTTTACCGGAC

ACTAAACCCAAAATTAAGGATAATGGAGATCTGGTTTTGTCAAGCCCCAGTAATGTAACA

CTGCCCCAAGTGAAAACAGAAAAAGAAGATTTCATCGAACTCTGCACCCCTGGGGTAATT

AAGCAAGAGAAACTGGGCACAGTTTACTGTCAGGCAAGCTTTCCTGGAGCAAATATAATT

GGTAATAAAATGTCTGCCATTTCTGTTCATGGTGTGAGTACCTCTGGAGGACAGATGTAC

CACTATGACATGAATACAGCATCCCTTTCTCAACAGCAGGATCAGAAGCCTATTTTTAAT

GTCATTCCACCAATTCCCGTTGGTTCCGAAAATTGGAATAGGTGCCAAGGATCTGGAGAT

GACAACTTGACTTCTCTGGGGACTCTGAACTTCCCTGGTCGAACAGTTTTTTCTAATGGC

TATTCAAGCCCCAGCATGAGACCAGATGTAAGCTCTCCTCCATCCAGCTCCTCAACAGCA

ACAACAGGACCACCTCCCAAACTCTGCCTGGTGTGCTCTGATGAAGCTTCAGGATGTCAT

TATGGAGTCTTAACTTGTGGAAGCTGTAAAGTTTTCTTCAAAAGAGCAGTGGAAGGACAG

-continued

CACAATTACCTATGTGCTGGAAGGAATGATTGCATCATCGATAAAATTCGAAGAAAAAAC

TGCCCAGCATGCCGCTATCGAAAATGTCTTCAGGCTGGAATGAACCTGGAAGCTCGAAAA

ACAAAGAAAAAAATAAAAGGAATTCAGCAGGCCACTACAGGAGTCTCACAAGAAACCTCT

GAAAATCCTGGTAACAAAACAATAGTTCCTGCAACGTTACCACAACTCACCCCTACCCTG

GTGTCACTGTTGGAGGTTATTGAACCTGAAGTGTTATATGCAGGATATGATAGCTCTGTT

CTGACGGCCGACCAGATGGTCAGTGCCTTGTTGGATGCTGAGCCCCCCATACTCTATTCC

GAGTATGATCCTACCAGACCCTTCAGTGAAGCTTCGATGATGGGCTTACTGACCAACCTG

GCAGACAGGGAGCTGGTTCACATGATCAACTGGGCGAAGAGGGTGCCAGGCTTTGTGGAT

TTGACCCTCCATGATCAGGTCCACCTTCTAGAATGTGCCTGGCTAGAGATCCTGATGATT

GGTCTCGTCTGGCGCTCCATGGAGCACCCAGGGAAGCTACTGTTTGCTCCTAACTTGCTC

TTGGACAGGAACCAGGGAAAATGTGTAGAGGGCATGGTGGAGATCTTCGACATGCTGCTG

GCTACATCATCTCGGTTCCGCATGATGAATCTGCAGGGAGAGGAGTTTGTGTGCCTCAAA

TCTATTATTTTGCTTAATTCTGGAGTGTACACATTTCTGTCCAGCACCCTGAAGTCTCTG

GAAGAGAAGGACCATATCCACCGAGTCCTGGACAAGATCACAGACACTTTGATCCACCTG

ATGGCCAAGGCAGGCCTGACCCTGCAGCAGCAGCACCAGCGGCTGGCCCAGCTCCTCCTC

ATCCTCTCCCACATCAGGCACATGAGTAACAAAGGCATGGAGCATCTGTACAGCATGAAG

TGCAAGAACGTGGTGCCCCTCTATGACCTGCTGCTGGAGATGCTGGACGCCCACCGCCTA

CATGCGCCCACTAGCCGTGGAGGGGCATCCGTGGAGGAGACGGACCAAAGCCACTTGGCC

ACTGCGGGCTCTACTTCATCGCATTCCTTGCAAAAGTATTACATCACGGGGGAGGCAGAG

GGTTTCCCTGCCACGGTCTAA

SEQ ID NO: 6 is the amino acid sequence of traceable fusion protein eGFP-GR-ER310. The sequence includes the following features at the indicated amino acid positions:

EGFP (1-239)

GA Linker (240-249)

hGR (250-800)

hER (801-1086)

MVSKGEELFTGVVPILVELDGDVNGHKFSVSGEGEGDATYGKLTLKFICTTGKLPVPWPT

LVTTLTYGVQCFSRYPDHMKQHDFFKSAMPEGYVQERTIFFKDDGNYKTRAEVKFEGDTL

VNRIELKGIDFKEDGNILGHKLEYNYNSHNVYIMADKQKNGIKVNFKIRHNIEDGSVQLA

DHYQQNTPIGDGPVLLPDNHYLSTQSALSKDPNEKRDHMVLLEFVTAAGITLGMDELYKG

AGAGAGAGADSKESLTPGREENPSSVLAQERGDVMDFYKTLRGGATVKVSASSPSLAVAS

QSDSKQRRLLVDFPKGSVSNAQQPDLSKAVSLSMGLYMGETETKVMGNDLGFPQQGQISL

SSGETDLKLLEESIANLNRSTSVPENPKSSASTAVSAAPTEKEFPKTHSDVSSEQQHLKG

QTGTNGGNVKLYTTDQSTFDILQDLEFSSGSPGKETNESPWRSDLLIDENCLLSPLAGED

DSFLLEGNSNEDCKPLILPDTKPKIKDNGDLVLSSPSNVTLPQVKTEKEDFIELCTPGVI

KQEKLGTVYCQASFPGANIIGNKMSAISVHGVSTSGGQMYHYDMNTASLSQQQDQKPIFN

VIPPIPVGSENWNRCQGSGDDNLTSLGTLNFPGRTVFSNGYSSPSMRPDVSSPPSSSSTA

TTGPPPKLCLVCSDEASGCHYGVLTCGSCKVFFKRAVEGQHNYLCAGRNDCIIDKIRRKN

CPACRYRKCLQAGMNLEARKTKKKIKGIQQATTGVSQETSENPGNKTIVPATLPQLTPTL

-continued

VSLLEVIEPEVLYAGYDSSVLTADQMVSALLDAEPPILYSEYDPTRPFSEASMMGLLTNL

ADRELVHMINWAKRVPGFVDLTLHDQVHLLECAWLEILMIGLVWRSMEHPGKLLFAPNLL

LDRNQGKCVEGMVEIFDMLLATSSRFRMMNLQGEEFVCLKSIILLNSGVYTFLSSTLKSL

EEKDHIHRVLDKITDTLIHLMAKAGLTLQQQHQRLAQLLLILSHIRHMSNKGMEHLYSMK

CKNVVPLYDLLLEMLDAHRLHAPTSRGGASVEETDQSHLATAGSTSSHSLQKYYITGEAE

GFPATV*

SEQ ID NO: 7 is the nucleic acid sequence which encodes traceable fusion protein eGFP-GR-TR216. The sequence includes the following features at the indicated nucleotide positions:

EGFP (1-717)

GA Linker (718-747)

hGR (748-2400)

hTR (2401-3141)

ATGGTGAGCAAGGGCGAGGAGCTGTTCACCGGGGTGGTGCCCATCCTGGTCGAGCTGGAC

GGCGACGTAAACGGCCACAAGTTCAGCGTGTCCGGCGAGGGCGAGGGCGATGCCACCTAC

GGCAAGCTGACCCTGAAGTTCATCTGCACCACCGGCAAGCTGCCCGTGCCCTGGCCCACC

CTCGTGACCACCCTGACCTACGGCGTGCAGTGCTTCAGCCGCTACCCCGACCACATGAAG

CAGCACGACTTCTTCAAGTCCGCCATGCCCGAAGGCTACGTCCAGGAGCGCACCATCTTC

TTCAAGGACGACGGCAACTACAAGACCCGCGCCGAGGTGAAGTTCGAGGGCGACACCCTG

GTGAACCGCATCGAGCTGAAGGGCATCGACTTCAAGGAGGACGGCAACATCCTGGGGCAC

AAGCTGGAGTACAACTACAACAGCCACAACGTCTATATCATGGCCGACAAGCAGAAGAAC

GGCATCAAGGTGAACTTCAAGATCCGCCACAACATCGAGGACGGCAGCGTGCAGCTCGCC

GACCACTACCAGCAGAACACCCCCATCGGCGACGGCCCCGTGCTGCTGCCCGACAACCAC

TACCTGAGCACCCAGTCCGCCCTGAGCAAAGACCCCAACGAGAAGCGCGATCACATGGTC

CTGCTGGAGTTCGTGACCGCCGCCGGGATCACTCTCGGCATGGACGAGCTGTACAAGGGC

GCTGGAGCAGGGGCTGGAGCCGGAGCTGACTCCAAAGAATCATTAACTCCTGGTAGAGAA

GAAAACCCCAGCAGTGTGCTTGCTCAGGAGAGGGGAGATGTGATGGACTTCTATAAAACC

CTAAGAGGAGGAGCTACTGTGAAGGTTTCTGCGTCTTCACCCTCACTGGCTGTCGCTTCT

CAATCAGACTCCAAGCAGCGAAGACTTTTGGTTGATTTTCCAAAAGGCTCAGTAAGCAAT

GCGCAGCAGCCAGATCTGTCCAAAGCAGTTTCACTCTCAATGGGACTGTATATGGGAGAG

ACAGAAACAAAAGTGATGGGAAATGACCTGGGATTCCCACAGCAGGGCCAAATCAGCCTT

TCCTCGGGGGAAACAGACTTAAAGCTTTTGGAAGAAAGCATTGCAAACCTCAATAGGTCG

ACCAGTGTTCCAGAGAACCCCAAGAGTTCAGCATCCACTGCTGTGTCTGCTGCCCCCACA

GAGAAGGAGTTTCCAAAAACTCACTCTGATGTATCTTCAGAACAGCAACATTTGAAGGGC

CAGACTGGCACCAACGGTGGCAATGTGAAATTGTATACCACAGACCAAAGCACCTTTGAC

ATTTTGCAGGATTTGGAGTTTTCTTCTGGGTCCCCAGGTAAAGAGACGAATGAGAGTCCT

TGGAGATCAGACCTGTTGATAGATGAAAACTGTTTGCTTTCTCCTCTGGCGGGAGAAGAC

GATTCATTCCTTTTGGAAGGAAACTCGAATGAGGACTGCAAGCCTCTCATTTTACCGGAC

ACTAAACCCAAAATTAAGGATAATGGAGATCTGGTTTTGTCAAGCCCCAGTAATGTAACA

CTGCCCCAAGTGAAAACAGAAAAAGAAGATTTCATCGAACTCTGCACCCCTGGGGTAATT

-continued

AAGCAAGAGAAACTGGGCACAGTTTACTGTCAGGCAAGCTTTCCTGGAGCAAATATAATT

GGTAATAAAATGTCTGCCATTTCTGTTCATGGTGTGAGTACCTCTGGAGGACAGATGTAC

CACTATGACATGAATACAGCATCCCTTTCTCAACAGCAGGATCAGAAGCCTATTTTTAAT

GTCATTCCACCAATTCCCGTTGGTTCCGAAAATTGGAATAGGTGCCAAGGATCTGGAGAT

GACAACTTGACTTCTCTGGGGACTCTGAACTTCCCTGGTCGAACAGTTTTTTCTAATGGC

TATTCAAGCCCCAGCATGAGACCAGATGTAAGCTCTCCTCCATCCAGCTCCTCAACAGCA

ACAACAGGACCACCTCCCAAACTCTGCCTGGTGTGCTCTGATGAAGCTTCAGGATGTCAT

TATGGAGTCTTAACTTGTGGAAGCTGTAAAGTTTTCTTCAAAAGAGCAGTGGAAGGACAG

CACAATTACCTATGTGCTGGAAGGAATGATTGCATCATCGATAAAATTCGAAGAAAAAAC

TGCCCAGCATGCCGCTATCGAAAATGTCTTCAGGCTGGAATGAACCTGGAAGCTCGAAAA

ACAAAGAAAAAAATAAAAGGAATTCAGCAGGCCACTACAGGAGTCTCACAAGAAACCTCT

GAAAATCCTGGTAACAAAACAATAGTTCCTGCAACGTTACCACAACTCACCCCTACCCTG

GTGTCACTGTTGGAGGTTATTGAACCTGAAGTGTTATATGCAGGATATGATAGCTCTGTT

GACGAGGAATGGGAGCTCATCAAAACTGTCACCGAAGCCCATGTGGCGACCAACGCCCAA

GGCAGCCACTGGAAGCAAAAACGGAAATTCCTGCCAGAAGACATTGGACAAGCACCAATA

GTCAATGCCCCAGAAGGTGGAAAGGTTGACTTGGAAGCCTTCAGCCATTTTACAAAAATC

ATCACACCAGCAATTACCAGAGTGGTGGATTTTGCCAAAAAGTTGCCTATGTTTTGTGAG

CTGCCATGTGAAGACCAGATCATCCTCCTCAAAGGCTGCTGCATGGAGATCATGTCCCTT

CGCGCTGCTGTGCGCTATGACCCAGAAAGTGAGACTTTAACCTTGAATGGGGAAATGGCA

GTGACACGGGGCCAGCTGAAAAATGGGGGTCTTGGGGTGGTGTCAGACGCCATCTTTGAC

CTGGGCATGTCTCTGTCTTCTTTCAACCTGGATGACACTGAAGTAGCCCTCCTTCAGGCC

GTCCTGCTGATGTCTTCAGATCGCCCGGGGCTTGCCTGTGTTGAGAGAATAGAAAAGTAC

CAAGATAGTTTCCTGCTGGCCTTTGAACACTATATCAATTACCGAAAACACCACGTGACA

CACTTTTGGCCAAAACTCCTGATGAAGGTGACAGATCTGCGGATGATAGGAGCCTGCCAT

GCCAGCCGCTTCCTGCACATGAAGGTGGAATGCCCCACAGAACTCTTCCCCCCTTTGTTC

TTGGAAGTGTTCGAGGATTAA

SEQ ID NO: 8 is the amino acid sequence of traceable fusion protein eGFP-GR-TR216. The sequence includes the following features at the indicated amino acid positions:

EGFP (1-290)

GA Linker (240-249)

hGR (250-800)

hTR (801-1046)

MVSKGEELFTGVVPILVELDGDVNGHKFSVSGEGEGDATYGKLTLKFICTTGKLPVPWPT

LVTTLTYGVQCFSRYPDHMKQHDFFKSAMPEGYVQERTIFFKDDGNYKTRAEVKFEGDTL

VNRIELKGIDFKEDGNILGHKLEYNYNSHNVYIMADKQKNGIKVNFKIRHNIEDGSVQLA

DHYQQNTPIGDGPVLLPDNHYLSTQSALSKDPNEKRDHMVLLEFVTAAGITLGMDELYKG

AGAGAGAGADSKESLTPGREENPSSVLAQERGDVMDFYKTLRGGATVKVSASSPSLAVAS

QSDSKQRRLLVDFPKGSVSNAQQPDLSKAVSLSMGLYMGETETKVMGNDLGFPQQGQISL

SSGETDLKLLEESIANLNRSTSVPENPKSSASTAVSAAPTEKEFPKTHSDVSSEQQHLKG

-continued

```
QTGTNGGNVKLYTTDQSTFDILQDLEFSSGSPGKETNESPWRSDLLIDENCLLSPLAGED

DSFLLEGNSNEDCKPLILPDTKPKIKDNGDLVLSSPSNVTLPQVKTEKEDFIELCTPGVI

KQEKLGTVYCQASFPGANIIGNKMSAISVHGVSTSGGQMYHYDMNTASLSQQQDQKPIFN

VIPPIPVGSENWNRCQGSGDDNLTSLGTLNFPGRTVFSNGYSSPSMRPDVSSPPSSSSTA

TTGPPPKLCLVCSDEASGCHYGVLTCGSCKVFFKRAVEGQHNYLCAGRNDCIIDKIRRKN

CPACRYRKCLQAGMNLEARKTKKKIKGIQQATTGVSQETSENPGNKTIVPATLPQLTPTL

VSLLEVIEPEVLYAGYDSSVDEEWELIKTVTEAHVATNAQGSHWKQKRKFLPEDIGQAPI

VNAPEGGKVDLEAFSHFTKIITPAITRVVDFAKKLPMFCELPCEDQIILLKGCCMEIMSL

RAAVRYDPESETLTLNGEMAVTRGQLKNGGLGVVSDAIFDLGMSLSSFNLDDTEVALLQA

VLLMSSDRPGLACVERIEKYQDSFLLAFEHYINYRKHHVTHFWPKLLMKVTDLRMIGACH

ASRFLHMKVECPTELFPPLFLEVFED*
```

SEQ ID NOs: 9-22 are the following primer sequences used for Q-PCR analysis:

| | Sequence | SEQ ID NO: |
|---|---|---|
| Mouse cells (3134) | | |
| Per1 For | CTTCTGGCAATGGCAAGGACTC | 9 |
| Per1 Rev | CAGCATCATGCCATCATACACACA | 10 |
| Tgm2 For | TGTCACCAGGGATGAGAGACGG | 11 |
| Tgm2 Rev | TCCAAATCACACCTCTCCAGGAG | 12 |
| Lcn2 For | ACCTCTCATTTCTTGCAGTTCCG | 12 |
| Lcn2 Rev | CAGGATGGAGGTGACATTGTAGCT | 13 |
| β-Actin For | AGTGTGACGTTGACATCCGTA | 15 |
| β-Actin Rev | GCCAGAGCAGTAATCTCCTTCT | 16 |
| Human cells (LNCaP) | | |
| hNKX3.1 For | TGACAGTGGGCTGTTTGTTC | 17 |
| hNKX3.1 Rev | AAGACCCCAAGTGCCTTTCT | 18 |
| hRHOU For | TTTCAAGGATGCTGGCTCTT | 19 |
| hRHOU Rev | GGCCTCAGCTTGTCAAATTC | 20 |
| GAPDH For | AAGGTGAAGGTCGGAGTCAAC | 21 |
| GAPDH Rev | GGGGTCATTGATGGCAACAATA | 22 |

DETAILED DESCRIPTION

I. Abbreviations

AhR aryl hydrocarbon receptor
AR androgen receptor
ATRA all-trans retinoic acid
CAR constitutive androstane receptor
cst corticosterone
dex dexamethasone
ER estrogen receptor protein (α, β)
ERR estrogen-related receptor (α, β, γ)
FP fluorescent protein
FXR farnesoid X receptor
GCNF germ cell nuclear factor
GFP green fluorescent protein
GFP-AhR chimera w/aryl hydrocarbon receptor and GFP
GFP-AR chimera w/androgen receptor and GFP
GFP-GR chimera w/ GR (or GR*) and GFP (also, GR-GFP)
GFP-GR-ER chimera w/ GR translocation domain, estrogen receptor, and GFP
GFP-GR-RAR chimera w/ GR translocation domain, retinoic acid receptor, and GFP
GFP-GR-TR chimera w/ GR translocation domain, thyroid hormone receptor, and GFP
GFP-PR-B chimera w/ GR translocation domain, progesterone B receptor, and GFP
GR glucocorticoid receptor
GR* modified GR with increased ligand binding affinity
HNF4 hepatocyte nuclear factor-4 (α, γ)
Hsp heat shock protein
LBD ligand binding domain (of a receptor protein)
LCA lithocholic acid
LRH-1 liver receptor homolog-1
LTR long terminal repeat
LXR liver X receptor (α, β)
MR mineralocorticoid receptor
MMTV mouse mammary tumor virus
NF1 nuclear factor 1
NHRs nuclear hormone receptors
NRNC Nuclear Receptors Nomenclature Committee
OTF1 octomer transcription factor 1
POCIS polar organic chemical integrative samplers
PPAR peroxisome proliferator-activated receptor (α, β/δ, γ)
PR progesterone receptor
PXR pregnane X receptor
RAR retinoic acid receptor
ROR RAR-related orphan receptor (α, β, γ)
RRE Rev Responsive Element
RxR retinoid-X receptor (α, β, γ)
SF1 steroidogenic factor 1
SHP small heterodimer partner
SRC1 steroid receptor coactivator 1
TR thyroid hormone receptor (α, β)
$T_3$ triiodothyronine
$T_4$ thyroxine
UDCA ursodeoxycholic acid
VDR vitamin D receptor
WWTP waste water treatment plant II. Terms Unless otherwise noted, technical terms are used according to conventional usage. In order to facilitate review of the various embodiments of the invention, the following explanations of specific terms are provided:

Cell-based System: A system based employing live cells derived, isolated, or otherwise acquired from a living organism. This term includes, for example, a cell culture.

Chimera/Chimeric: A recombinant nucleic acid molecule generated by cloning portion(s) of one or more nucleic acid sequence(s) in-frame to one or more other nucleic acid sequence(s) to produce a single nucleic acid sequence capable of being transcribed into a polypeptide. A polypeptide expressed from such a nucleic acid sequence chimera is referred to as a "chimeric protein" or "protein chimera".

Contacting: To place in direct physical association, including in solid or in liquid form. Contacting can occur in vivo, for example by administering an agent to a subject, or in vitro for example with isolated cells or cell-cultures.

Control: Samples believed to be normal (e.g., representative of an activity or function in the absence of the variable being tested), as well as laboratory values, even though possibly arbitrarily set, keeping in mind that such values can vary from laboratory to laboratory. A control sample or group is practically identical to the test sample or group, except for the variable(s) of interest the effect of which is being tested, which is only applied to or found in the test group. A difference between a test sample and a control can be an increase or a decrease. The difference can be a qualitative difference or a quantitative difference, for example a statistically significant difference. In some examples, a difference is an increase or decrease, relative to a control, of at least about 10%, such as at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Detect: To determine if an agent (such as a bacterium) is present or absent. In some examples this can further include quantification. For example, use of the disclosed methods permits detection of one or more target bacterium, such as by flow cytometry or fluorescence microscopy. Detection can be in bulk, so that a macroscopic number of molecules can be observed contemporaneously or simultaneously. Detection can also include detection of single events, such as a single bacterium.

Emission or emission signal: The light of a particular wavelength generated from a source. In particular examples, an emission signal is emitted from a fluorophore, such as a fluorescent protein, after the fluorophore absorbs light at its excitation wavelength(s).

Environmental sample: A sample obtained from the environment, for instance a water sample (e.g., of surface, subsurface (ground), rain, run-off, well, spring, drinking, river, estuary, ocean, effluent, treated or untreated sewage, etc. water), soil sample (including soil samples that contain water), air sample, or a sample of another substance.

Excitation or excitation signal: The light of a particular wavelength necessary and/or sufficient to excite an electron transition to a higher energy level. In particular examples, an excitation is the light of a particular wavelength necessary and/or sufficient to excite a fluorophore, such as a fluorescent protein, to a state such that the fluorophore will emit a different (such as a longer) wavelength of light then the wavelength of light from the excitation signal.

Fluorescent property: A characteristic of a fluorescent molecule, such as a fluorescent protein, for example green fluorescent protein, red fluorescent protein, yellow fluorescent protein, cyan fluorescent protein and the like. Examples of fluorescent properties include the molar extinction coefficient at an appropriate excitation wavelength, the fluorescence quantum efficiency, the shape of the excitation spectrum or emission spectrum (the "fluorescence spectrum," the excitation wavelength maximum and emission wavelength maximum, the ratio of excitation amplitudes at two different wavelengths, the ratio of emission amplitudes at two different wavelengths, the excited state lifetime, or the fluorescence anisotropy. Quantifying fluorescence refers to the determination of the amount of fluorescence generated by a fluorophore, for example a fluorescent protein, which can be the quantity of photons emitted by a fluorophore. In some examples, fluorescence is quantified by measuring the intensity of a fluorescence signal at a particular wavelength, for example the wavelength of the emission maxima of a particular fluorophore, such as a fluorescent protein. Fluorescence intensity can also be quantified at a wavelength that is not the emission maxima of a particular fluorophore, for example to avoid emission spectra that overlap and thereby interfere with the emission maxima of a particular fluorophore, such as a particular fluorescent protein. In some examples, a fluorescence signal is emitted by a population of fluorescent proteins, for example fluorescent proteins present in a population of cells containing such fluorescent proteins. Such a signal can be quantified, for example to determine the number, or relative number of cells that emit such a fluorescent signal. Detecting a pattern of fluorescence refers to the correlation of a fluorescent signal to a specific location to determine the location where a fluorescence signal, such as a fluorescent signal of a particular wavelength, originates. In some examples, a pattern of fluorescence determines the location and or shape of the cells that emit a fluorescence signal, such as cells containing a fluorescent protein, including for example to sub-cellular localization of the fluorescent protein (e.g., cytoplasmic or nuclear) as well as the absolute or relative quantitative distribution between sub-cellular compartments and organelles.

Fluorescent protein: A protein capable of emission of a detectable (and therefore traceable) fluorescent signal. Fluorescent proteins can be characterized by the wavelength of their emission spectrum. For example, wildtype green fluorescent protein (GFP) has a fluorescent emission spectrum in the green part of the visible spectrum. In addition to green-fluorescent proteins, fluorescent proteins are well known that fluoresce in other regions of the visible spectrum, for example blue-fluorescent proteins, cyan-fluorescent proteins, yellow-fluorescent proteins, orange-fluorescent proteins, red-fluorescent proteins, and far-red fluorescent proteins. Non-limiting examples of fluorescent proteins can be found in the following patent documents: U.S. Pat. Nos. 5,804,387; 6,090,919; 6,096,865; 6,054,321; 5,625,048; 5,874,304; 5,777,079; 5,968,750; 6,020,192; 6,146,826; 6,969,597; 7,150,979; 7,157,565; and 7,166,444; and published international patent applications WO 07/085,923; WO 07/052,102, WO 04/058973, WO 04/044203, WO 03/062270; and WO 99/64592. Additional examples of fluorescent proteins are available from Clontech, Laboratories, Inc. (Mountain View, Calif.) under the trade name Living Colors®. Nucleic acids encoding such fluorescent proteins can be incorporated into mammalian expression vectors for use in producing the disclosed fluorescent traceable proteins and fluorescent cell-lines.

Fusion protein: Proteins that have at least two domains fused together, at least one domain comprising traceable (marker) feature (such as a fluorescent protein domain) and another domain or set of domains that provides translocation of the fusion protein from one cellular compartment or organelle to another in a cell in which it is expressed upon the specific binding of a ligand (EDC) to the fusion protein. Optionally the translocation and ligand binding features may be provided from the same source protein (e.g., in a GFP-GR traceable translocation fusion protein). In other embodiments, the translocation and ligand binding features are provided from two different source proteins (thus making a "chimeric receptor" portion of the fusion protein), such that the resultant traceable translocating fusion protein contains domains or subdomains from at least three different source proteins. An example of such a three-component fusion protein is the GFP-GR-ER protein which contains GFP, translocating features of or derived from GR, and the ligand binding domain of an estrogen receptor.

In general, the domains of the disclosed fusions are genetically fused together, in that nucleic acid molecules that encode each protein domain (or subdomain) are functionally linked together, for instance directly or through the use of a linker oligonucleotide, thereby producing a single fusion-encoding (chimeric) nucleic acid molecule. The translated product of such a fusion-encoding (chimeric) nucleic acid molecule is the traceable translocating fusion protein.

High throughput technique: A fast, automated or semi-automated analysis process, for instance to analyze many samples at once in order to detect or measure the presence (or absence) of a substance. In certain examples, combining modern robotics, data processing and control software, liquid handling devices, and sensitive detectors, high throughput techniques allows the rapid screening of many (e.g., hundreds or thousands) samples in a short period of time and often in a highly parallel manner.

Traceable marker protein domain: A protein domain that is detectable based on its inherent structural or functional characteristics, such as fluorescence.

Nuclear hormone receptor family: Nuclear hormone receptors (NHRs) function as ligand-activated transcription factors and have roles in diverse cellular processes ranging from mammalian development and differentiation to metabolic homeostasis (Mangelsdorf et al., *Cell,* 83(6):835-839, 1995; Adams et al., *Science,* 287:2185-2195, 2000). NHRs bind to sequence-specific DNA response elements on target gene promoters as homodimers, heterodimers, or monomers. Structural and functional analyses of the NHR family have demonstrated that the receptors are comprised of functional modular domains. The DNA binding domain (DBD) consists of a well characterized zinc finger motif which recognizes a degenerate six to eight nucleotide sequence on the target DNA. The ligand binding domain (LBD) resides in the C-terminal portion of the protein and shares a common, predominantly alpha helical fold (Mangelsdorf et al., *Cell,* 83(6):835-839, 1995). As implied, this domain of the receptor is where cognate ligands of the receptors interact and induce conformational changes associated with transcriptional activation. Many of the known ligands for these receptors are essential metabolic products including retinoids, thyroid hormone, vitamin D3, bile acids, oxysterols, and prostenoids that act through their cognate receptors to control metabolic homeostasis in the body (Gudas, *J. Biol. Chem.,* 269(22):15399-15402, 1994). In addition, NHRs are also instrumental in the ability of the body to respond to and adapt to complex environmental cues.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Non-naturally occurring synthetic analogs include, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand (the nucleotide sequence of which is identical to the mRNA sequence and is usually provided in sequence listings) and non-coding strand (used as the template for transcription) of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

A first sequence is an "antisense" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence (for example a coding sequence of an antibody or fragment therefore herein disclosed) if the promoter affects the transcription or expression of the coding sequence. Generally, operably linked DNA sequences are contiguous and, where necessary to join two protein-coding regions, in the same reading frame.

ORF (open reading frame): A series of nucleotide triplets (codons) coding for amino acids without any termination codons. These sequences are usually translatable into a peptide. In some examples an open reading frame encodes an antibody or antibody fragment, such as those disclosed herein.

Polypeptide: A polymer in which the monomers are amino acid residues that are joined together through amide bonds, for example γ amide bonds (for example from the γ position of a glutamic acid side chain) or a amide bonds. When the amino acids are alpha-amino acids, either the L-optical isomer or the D-optical isomer can be used. The terms "polypeptide" or "protein" as used herein is intended to encompass any amino acid sequence and include modified sequences such as glycoproteins. The term "polypeptide" is specifically intended to cover naturally occurring proteins, as well as those that are recombinantly or synthetically produced.

The term "polypeptide fragment" refers to a portion of a polypeptide which exhibits at least one useful epitope. The term "functional fragments of a polypeptide" refers to all fragments of a polypeptide that retain an activity of the polypeptide. Biologically functional fragments, for example, can vary in size from a polypeptide fragment as small as an epitope capable of binding an antibody molecule to a large polypeptide capable of participating in the characteristic induction or programming of phenotypic changes within a cell.

Sample: A material to be analyzed, for example to determine if it contains one or more target. Includes but is not limited to biological samples (e.g., obtained from a human or veterinary subject); food samples (e.g., vegetable, dairy, fruit or meat sample); environmental samples (e.g., soil, air, water, surfaces), and the like.

Sewage: Water-based fluid containing organic matter and solutes. Sewage may include feces and urine from human and non-human animals. Sewage may include waste from human activities, for example, blackwater (e.g., toilet and dishwasher waste) and grey water (e.g. waste water generated from washing activities). Residential, institutional, commercial and industrial establishments may produce sewage, including waste from toilets, baths, showers, kitchens, sinks, etc. Typically, sewage is waste intended to be carried away from the source of the waste, for example, carried to a sewage treatment facility.

Receptor Superfamily: Family of steroid, nuclear, and orphan receptor proteins having an identifiable ligand binding domain. The term as used herein is intended to encompass the known classic nuclear receptors, hormone receptors, and orphan receptors, as well as proteins having an identifiable ligand binding domain which may discovered in the future.

TABLE 1

Representative Nuclear Receptors

| Sub-family and Group | NR/ Gene | Literature Names | Accession Number |
|---|---|---|---|
| 1A | NR1A1 | TRα, c-erbA-1, THRA | M24748 |
| | NR1A2 | TRβ, c-erbA-2, THRB | X04707 |
| 1B | NR1B1 | RARα | X06538 |
| | NR1B2 | RARβ, HAP | Y00291 |
| | NR1B3 | RARγ, RARD | M57707 |
| 1C | NR1C1 | PPARα | L02932 |
| | NR1C2 | PPARβ, NUC1, PPARδ, FAAR | L07592 |
| | NR1C3 | PPARγ | L40904 |

TABLE 1-continued

Representative Nuclear Receptors

| Sub-family and Group | NR/ Gene | Literature Names | Accession Number |
|---|---|---|---|
| 1D | NR1D1 | REVERBα, EAR1, EAR1A | M24898 |
| | NR1D2 | REVERBβ, EAR1β, BD73, RVR, HZF2 | L31785 |
| | NR1D3 | E75 | X51548 |
| 1E | NR1E1 | E78, DR-78 | U01087 |
| IF | NR1F1 | RORα, RZRα | U04897 |
| | NR1F2 | RORβ, RZRβ | Y08639 |
| | NR1F3 | RORγ, TOR | U16997 |
| | NR1F4 | HR3, DHR3, MHR3, GHR3, CNR3, CHR3 | M90806 U13075 |
| 1G | NR1G1 | CNR14 | U13074 |
| 1H | NR1H1 | ECR | M74078 |
| | NR1H2 | UR, OR-1, NER1, RIP15, LXRβ | U07132 |
| | NR1H3 | RLD1, LXR, LXRα | U22662 |
| | NR1H4 | FXR, RIP14, HRR1 | U09416 |
| 1I | NR1I1 | VDR | J03258 |
| | NR1I2 | ONR1, PXR, SXR, BXR | X75163 |
| | NR113 | MB67, CAR1, CARα | Z30425 |
| | NR1I4 | CAR2, CARβ | AF00932 |
| 1J | NR1J1 | DHR96 | U36792 |
| 1K | NR1K1 | NHR1 | U19360 |
| 2A | NR2A1 | HNF4 | X76930 |
| | NR2A2 | HNF4G | Z49826 |
| | NR2A3 | HNF4B | Z49827 |
| | NR2A4 | DHNF4, HNF4D | U70874 |
| 2B | NR2B1 | RXRA | X52773 |
| | NR2B2 | RXRB, H-2RIIBP, RCoR-1 | M84820 |
| | NR2B3 | RXRG | X66225 |
| | NR2B4 | USP, Ultraspiracle, 2C1, CF1 | X52591 |
| 2C | NR2C1 | TR2, TR2-11 | M29960 |
| | NR2C2 | TR4, TAK1 | L27586 |
| 2D | NR2D1 | DHR78 | U36791 |
| 2E | NR2E1 | TLL, TLX, XTLL | S72373 |
| | NR2E2 | TLL, Tailless | M34639 |
| 2F | NR2F1 | COUP-TFI, COUPTFA, EAR3, SVP44 | X12795 |
| | NR2F2 | COUP-TFII, COUPTFB, ARP1, SVP40 | M64497 |
| | NR2F3 | SVP, COUP-TF | M28863 |
| | NR2F4 | COUP-TFIII, COUPTFG | X63092 |
| | NR2F5 | SVP46 | X70300 |
| | NR2F6 | EAR2 | X12794 |
| 3A | NR3A1 | ERα | X03635 |
| | NR3A2 | ERβ | U57439 |
| 3B | NR3B1 | ERR1, ERRα | X51416 |
| | NR3B2 | ERR2, ERRβ | X51417 |
| 3C | NR3C1 | GR | X03225 |
| | NR3C2 | MR | M16801 |
| | NR3C3 | PR | M15716 |
| | NR3C4 | AR | M20132 |
| 4A | NR4A1 | NGFIB, TR3, N10, NUR77, NAK1 | L13740 |
| | NR4A2 | NURR1, NOT, RNR1, HZF-3, TINOR | X75918 |
| | NR4A3 | NOR1, MINOR | D38530 |
| | NR4A4 | DHR38, NGFIB | U36762 |
| | | CNR8, C48D5 | U13076 |
| 5A | NR5A1 | SF1, ELP, FTZ-F1, AD4BP | D88155 |
| | NR5A2 | LRH1, xFF1rA, xFF1rB, FFLR, PHR, FTF | U93553 |
| | NR5A3 | FTZ-F1 | M63711 |
| 5B | NR5B1 | DHR39, FTZF1B | L06423 |
| 6A | NR6A1 | GCNF1, RTR | U14666 |
| 0A | NR0A1 | KNI, Knirps | X13331 |
| | NR0A2 | KNRL, Knirps related | X14153 |
| | NR0A3 | EGON, Embryonic gonad, EAGLE | X16631 |
| | NR0A4 | ODR7 | U16708 |
| | NR0A5 | Trithorax | M31617 |
| 0B | NR0B1 | DAX1, AHCH | S74720 |
| | NR0B2 | SHP | L76571 |

[#] Derived from *A unified nomenclature system for the nuclear receptor superfamily* (*Nuclear Receptors Nomenclature Committee, Cell* 97(2):161-163, 1999).

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and"

unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, sequences defined by accession number, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Provided herein in a first set of embodiments are systems for detecting or quantifying a ligand (e.g., an agonist or an antagonist) of a superfamily receptor protein in an environmental sample. In examples thereof, the system comprises a first mammalian cell expressing a first traceable fusion protein; a second mammalian cell expressing a second traceable fusion protein; and a detection system for the detection of the cytoplasm-to-nuclear translocation of the marker proteins, wherein the first and second traceable fusion proteins independently comprise either: (1) a superfamily receptor protein, and a marker protein domain; or (2) the cytoplasmic/nuclear translocation domain of glucocorticoid receptor, the ligand binding domain of a superfamily receptor protein, and a marker protein domain. Optionally, the mammalian cells are human cells.

In examples of the described system for detecting or quantifying a ligand of a superfamily receptor protein in an environmental sample, the first traceable fusion protein binds a different ligand than the second traceable fusion protein.

In examples of the described system for detecting or quantifying a ligand of a superfamily receptor protein in an environmental sample, the marker protein domain is different in the first and second traceable fusion proteins. This enables differential detection of the two fusion proteins, for instance in the same analysis system or sample.

In any of the described system for detecting or quantifying a ligand of a superfamily receptor protein in an environmental sample, the marker protein domain may optionally be a fluorescent protein domain.

Also described are systems for detecting or quantifying a ligand of a superfamily receptor protein in an environmental sample, wherein the ligand for the first or second traceable fusion protein is a natural ligand for the superfamily receptor protein of the traceable fusion protein, or a natural or synthetic compound that binds competitively therewith.

Also provided are systems for detecting or quantifying a ligand of a superfamily receptor protein in an environmental sample that additionally comprise one or more compounds and/or compositions that stably associate with a traceable fusion protein in the absence of a ligand for the ligand binding domain of the traceable fusion protein, and which dissociates from the fusion protein in the presence of a ligand for the ligand binding domain of the traceable fusion protein.

Yet another embodiment provides a system for detecting or quantifying a ligand of a superfamily receptor protein in an environmental sample, which system includes at least four mammalian cell lines each expressing a different traceable fusion protein, wherein at least one traceable fusion protein binds a glucocorticoid, at least one traceable fusion protein binds an androgen, at least one traceable fusion protein binds a progestin, and at least one traceable fusion protein binds an aryl hydrocarbon.

The systems described herein are optionally provided as kits.

Also described are methods for detecting or quantifying an endocrine disruptor chemical (EDC) ligand in an environmental sample, which methods involve contacting with the environmental sample a human cell expressing in its cytoplasm a fusion protein comprising: a receptor for the ligand, which receptor translocates from the cytoplasm to the nucleus upon ligand binding; and a marker protein domain; and then detecting cytoplasmic to nuclear translocation of the fusion protein in response to a ligand of the ligand binding domain in the water sample.

Also described are methods of determining the concentration of an endocrine disruptor chemical (EDC) ligand in an environmental sample, which methods involve contacting with the environmental sample a population of eukaryotic cells expressing in their cytoplasm a fusion protein comprising: a receptor for the ligand, which receptor translocates from the cytoplasm to the nucleus upon ligand binding; and a marker protein domain; and scanning one or more test cell(s) to obtain signal data from the marker of the fusion protein; converting the signal data to obtain the cellular location of the labeled protein in the test cell(s); and analyzing the signal data using an analysis system having an algorithm to calculate changes in distribution of the labeled fusion protein between the cytoplasm and the nucleus of the test cell(s), the analysis system having the capability of providing an accurate reading of the concentration of the ligand.

In any of the provided systems, kits, and methods, the environmental sample can include a water sample, soil sample, or air sample. By way of example, where the environmental sample comprises a water sample, the sample includes in various embodiments one or more of surface water, sub-surface (ground) water, rain, run-off, well water, spring water, drinking water (processed or not), river water, estuary water, ocean water, effluent, treated sewage or untreated sewage.

Yet further embodiments are described herein.

IV. Systems and Kits for Detection of EDCs

Disclosed herein is use of a highly sensitive cytoplasm-to-nucleus translocation assay to monitor one or more EDC level or activity, for instance in water samples. A high throughput screen of water samples is described, using in one example a cell line expressing GFP-tagged glucocorticoid receptor (GR) (GFP-GR); the detected output that signals presence of EDC/ligand (such as glucocorticoid) in the sample is accumulation of fluorescence in the cell nucleus (that is, migration of the fluorescent fusion protein from the cytoplasm into the nucleus). By way of example, an automated imaging system (such as the PerkinElmer Opera® High Content Imaging system) can be used to image the change in fluorescence localization in individual cells; also contemplated are non-automated, direct microscopic examination embodiments.

Though the high-throughput, low cost, high sensitivity EDC detection system is described in detail with regard to a few exemplary traceable cytoplasm-to-nuclear marker proteins, it will be apparent to one of ordinary skill based on the teachings herein that the provided principles can be applied to the detection of other EDC compounds though use of different receptor fusions. Thus, specifically contemplated herein are methods and kits that employ cell lines expressing one or more of the following detector fusions: GFP-GR, GFP-AR, GFP-AhR, GFP-PR-B, GFP-GR-ER, GFP-GR-RAR, and GFP-GR-TR, as well as fusions in which the GFP is replaced with a different fluorescent domain that emits light at a different wavelength. Specifically contemplated are kits that include cell lines expressing two or more traceable fusion, where each is responsive to a different EDC and contains a differentially fluorescing traceable domain. Kits containing multiple cell lines, each of which expresses a different cytoplasm-to-nuclear traceable fusion protein are also contemplated. Also envisioned are GFP fusions to mutant, variant, or modified forms of nuclear receptors that manifest detectable subcellular relocalization in response to ligand.

A. Traceable Translocating Fusion Proteins with Non-Chimeric Receptors

Embodiments provided herein employ cells that express a traceable fusion protein, which changes its sub-cellular localization (for example, translocates from the cytoplasm into the nucleus) upon binding of an EDC ligand compound. Examples of such traceable translocating fusion proteins comprise a traceable marker domain (exemplified by a fluorescent protein domain, such as GFP) functionally fused to a nuclear superfamily receptor domain that is sufficient for both recognition of the EDC ligand and for consequent translocation of the fusion protein from the cytoplasm into the nucleus.

Cell lines expressing other "non-chimeric" receptors (that is, not needing to be fused to the translocation domain of GR) such as GFP-AR (Klokk, et al., *Mol. Cell. Biol.* 27:1823-1843, 2007), GFP-AhR (Elbi et al., *Proc Natl Acad Sci USA* 101(9):2876-2881, 2004), GFP-PR-B (Rayasam et al., *Mol Cell Biol* 25(6):2406-2418, 2005) have been generated previously in our laboratory. In addition to the GFP-GR, which could detect biologically active glucocorticoids in water samples, GFP-AR was used for the detection of androgen activity and positive results were obtained for many of the tested water samples.

A fluorescent protein (or protein domain) is a protein (or portion of a protein) that fluoresces in cells without adding exogenous cofactors. That is, it is a protein that can be expressed in cells and detected in these cells simply by exciting the protein with light and visualizing the resultant fluorescence. An example of such a fluorescent protein is the green fluorescent protein (GFP) originally isolated from the jellyfish *Aequorea victoria*. Another example of a fluorescent protein as defined herein is the green fluorescent protein originally isolated from *Renilla reniforms*, which exhibits a single absorption peak at 498 nm and an emission peak at 509 nm (Cubitt et al. *TIBS* 20: 448-455, 1995). It is also contemplated that modifications may be made to a fluorescent protein, as long as the resulting protein fluoresces when expressed in cells. The art recognizes many modifications that can be (and have been) made to existing fluorescent proteins, for instance to provide different excitation and emission peaks, to increase stability, that speed up the rate of the oxidation step of chromophore formation, that increase brightness at longer wavelengths, and that reduce pohotoisomerization and/or photobleaching.

Optionally, the fusion protein can include a linking peptide sequence between the traceable (e.g., fluorescent protein) domain and the steroid or other receptor domain. For example, a sequence of the amino acids glycine and alanine, or a sequence of alanine alone can be used; however, any sequence of amino acids and any length can be used that does not interfere with the binding of the receptor domain to its response element and that does not prevent fluorescence of the fluorescent protein. Typically, a linker peptide will range from two to about ten amino acids but maybe shorter or longer. Of course, certain linker peptides maybe preferred over others, e.g., the presence of four basic amino acids in a string of six might suffice as a nuclear localization signal so as to mislocate the uninduced state of the factor. A linker peptide can be used to separate the fluorescent protein structurally from the response element and can function to allow the fluorescent protein independently of the remaining portion of the chimeric protein. Typically, the traceable protein domain (e.g., fluorescent protein) can be fused to either the C-terminus or the N-terminus of the ligand receptor domain; however, the preferable construction for any specific fusion protein can readily be determined. Linker peptides can readily be introduced between the two protein domains in the fusion protein by producing a nucleic acid that encodes the fusion protein having the linker sequence between the detectable protein component and ligand responsive/translocation component.

The ligand binding domain (e.g., transcription factor component) of the traceable fusion protein can be derived from any selected mammal. Additionally, fusion proteins utilizing a transcription factor from one mammal can often be used in a cell from another mammal. F or example, the glucocorticoid receptor amino acid sequence is highly conserved, particularly in the binding region among rat, human and mouse, and, for example, the rat glucocorticoid receptor binds with high affinity to the human glucocorticoid response element. However, in various embodiments provided herein, the ligand-binding and/or translocation component(s) of the traceable fusion proteins are based on human proteins.

Additional information regarding the construction of traceable translocating fusion proteins useful in the described methods and kits is provided in WO 97/20931 and U.S. Pat. Nos. 6,455,300, 7,312,032 and 8,058,395, each of which is incorporated by reference herein.

B. Traceable Translocating Fusion Proteins with Chimeric Receptors

Also contemplated are cell lines, methods, systems and kits that employ traceable chimeric receptors, that is traceable receptors that include a portion of a nuclear receptor for example responsible for cytoplasmic/nuclear translocation activity functionally fused to the ligand-binding portion of another superfamily receptor. A representative example is the GR-ER chimera (Martinez et al., *J. Ster. Biochem Mol. Biol.* 97:307-321, 2005), which contains the rat GR (rGR) N-terminus, DNA binding domain (DBD) and hinge regions upstream of a hybrid ligand binding domain (LBD) composed of GR helix 1 and partial loop 1-3 sequences linked to human ER alpha (hER$\alpha$) LBD sequences starting with the C-terminus of loop 1-3.

The construction of examples of such chimeric traceable receptors is described in U.S. Patent Publication No. 2003/0077645, Mackem et al. (*J. Biol. Chem.* 276(49):45501-45504, 2001), and Martinez et al. (*J. Ster. Biochem Mol. Biol.* 97:307-321, 2005), each of which is incorporated herein by reference. These references describe production of fluorescently tagged fusion proteins that contain a chimera between the translocation features of glucocorticoid receptor and another nuclear superfamily receptor, such as the estrogen receptor, a retinoic acid receptor, and so forth. In each case, the labeled chimera is found in the cytoplasm in the absence of its cognate ligand), and is rapidly translocated to the nucleus in a dose-dependent manner upon exposure of the cell to ligand.

C. Additional Chimeric Receptors

GFP-GR (pCI-nGFP-C656G) and GFP-AR (eGFP-hAR) fusion proteins have been published ((Walker et al., *Methods* (*Comp. to Meth. Enzym.*) 19:386-393, 1999; Klokk et al., *Mol. Cell. Biol.* 27:1823-1843, 2007) and have proven useful in detecting biologically active glucocorticoid and androgens in water samples, as described below in Example 1. Additional chimeras (eGFP-GR-ER310 and eGFP-GR-TR216) have been constructed. Mammalian cell lines can be readily prepared which express each of these chimeras under tetracycline regulation. The nucleotide sequences of pCI-nGFP-C656G (SEQ ID NO: 1), eGFP-hAR (SEQ ID NO: 3), eGFP-GR-ER310 (SEQ ID NO: 5), and eGFP-GR-TR216 (SEQ ID NO: 7) are provided.

D. Detection Cell Lines

The methods and kits described herein employ cell lines that express at least one traceable translocating fusion protein as described herein. For detection of the translocation of the labeled fusion protein from one sub-cellular compartment or organelle to another, any eukaryotic cell can be utilized, though mammalian cells and particularly human cells are contemplated. Representative methods for the construction of cell lines useful in the described methods and kits, as well as examples of such cell lines, are provided in WO 97/20931, U.S. Pat. Nos. 6,455,300, 7,312,032 and 8,058,395; U.S. Patent Publication No. 2003/0077645, Mackem et al. (*J. Biol. Chem.* 276(49):45501-45504, 2001), and Martinez et al. (*J. Ster. Biochem Mol. Biol.* 97:307-321, 2005), each of which is incorporated by reference herein.

In addition to steroid receptors, there are other ligand-dependent receptors (such as thyroid hormone receptor, retinoic acid receptor, retinoid X receptor, TCCD (dioxin) receptor (AhR), fatty acid activatable receptors, etc.) and stimulus-dependent receptors (such as peroxisome proliferator activated receptor, growth factor-dependent receptors such as epidermal growth factor, nerve growth factor, etc.), and factors (such as CREB, NFAT, NFkB/IkB, etc.), and other receptors whose ligand remains to be defined (such as mammalian homologs of the Drosophila tailless, knirps, sevenup, FTZF1 genes, etc.). Many of these receptors or factors can be found listed in Parker, Steroid Hormone Action (Oxford University Press, New York, pp. 210, 1993), in Tsai & O'Malley (*Annu. Rev. Biochem.* 63:451-486, 1994), and in GenBank and other publicly available sequence databases, which contain additional receptors as well as the complete nucleotide sequences of the genes and cDNAs.

E. Methods for Detecting and/or Quantifying EDC(s) in Environmental Samples

The present disclosure provides methods of detecting in an environmental sample the presence of an agonist or antagonist of a nuclear superfamily receptor comprising contacting the sample with a cell expressing at least one traceable translocating fusion protein and directly detecting the sub-cellular location of fluorescence (or other appropriate label) within the cell, the location of fluorescence aggregated in the nucleus indicating the presence in the environmental sample of at least one agonist or antagonist of the ligand-binding EDC receptor domain of the traceable translocation fusion protein. In addition to the exemplary methods described herein, methods generally applicable for detecting or quantifying a ligand using a traceable translocation fusion protein can be found in WO 97/20931, U.S. Pat. Nos. 6,455,300, 7,312,032 and 8,058,395; U.S. Patent Publication No. 2003/0077645, Mackem et al. (*J. Biol. Chem.* 276(49):45501-45504, 2001), and Martinez et al. (*J. Ster. Biochem Mol. Biol.* 97:307-321, 2005), each of which is incorporated by reference herein.

Direct detection means detection of the fluorescence emitted from the site in the cells when excited by (ultraviolet or visible) light, without the need for any additional chemical reactions or treatment of the cells. The fluorescence is directly detected by any device capable of detecting fluorescence, such as a fluorescent microscope, as visualized by the eye of the operator of the microscope at the time or as recorded from the microscope such as by photography of the field of view or through the use of photosensitive detectors.

A fluorescent microscope, such as a confocal laser scanning microscope or an epifluorescent microscope, can be used, as is known in the art.

There is no requirement that cells be, e.g., fixed or stained or contacted by any additional reagents, in order to detect the translocation. Thus living cells can be assayed, and results obtained, shortly (for instance, about 30 minutes) after being contacted with a test sample. Furthermore, screening nuclear localization of fluorescence (translocation) can readily be adapted to high throughput computerized image analysis. Thus, the analysis of large numbers of samples can be automated, for instance for the repetitive examination of multiple environmental samples (for instance, from multiple sources or locations) as well as for the large-scale screening of sets of samples for multiple EDC contaminants.

Also provided is a method of detecting or monitoring the level of agonists and antagonists of a steroid receptor in an environmental sample, comprising obtaining periodic samples from a source or location over time (e.g., on a daily, weekly, monthly, bi-annually, annually, or longer basis), contacting the samples with cell(s) expressing one or more of the herein-described traceable translocating fusion proteins, and detecting the location of fluorescence within the cells. Optionally, the cells each or collectively express a set of two or more different traceable translocating fusion proteins that are responsive to different ligands (e.g., different EDCs known to or suspected of being contaminants in the environment being sampled). The amount or magnitude of fluorescence migration from the cytoplasm to the nucleus can be compared between the periodic samples, in order to monitor trends (upwards or downwards) in the levels of EDC contamination at a single location or set of locations over time. Decrease in the nuclear translocation in a later-obtained sample relative to an earlier-obtained sample indicating a decrease in level of the EDC agonist or antagonist of the receptor in the sample, while an increase in translocation into the nucleus in a later-obtained sample relative to an earlier-obtained sample indicates an increase in level of the EDC agonist or antagonist of the steroid receptor in the sample.

F. Automated High Throughput Analysis Systems and Image Analysis Software

Described herein is one embodiment of automated high throughput analysis of the presence of EDCs in environmental samples, using the PerkinElmer Opera® High Content Image Screening System and accompanying software package. With this teaching, additional high throughput applications of the herein described EDC detection and measuring methods are now enabled.

Contemplated herein is the use of "arrays" of cells that express one or more traceable translocating fusion protein, which cells are placed into an array such as a microchannel array, microtiter plate or other array system that permits separate cell samples to be contacted separately with different test samples (e.g., environmental samples, such as water samples, to be analyzed for the presence or level of one or more EDCs).

Arrays, as the term is used herein, are arrangements of addressable locations on a substrate; each address may contain a sample of one or more cells or cell lines. A "microarray" is an array that is miniaturized so as to require microscopic examination for evaluation of hybridization or other detection signals. "Macroarrays" are somewhat larger, such that at least the spot at each address is recognizable by the naked human eye. Primary examination for the presence and location of cellular fluorescence (or other traceable signals) in cells of the array is usually carried out using a microscope or other magnifying device.

Within an array, each arrayed cell sample is addressable, in that its location can be reliably and consistently determined within the at least the two dimensions of the array surface. Thus, in ordered arrays the location of each cell sample is assigned to the sample at the time when it is applied to the array and usually a key is provided in order to correlate each location with the appropriate "target" cell sample. Often, ordered arrays are arranged in a symmetrical grid pattern, but samples could be arranged in other patterns (e.g., in radially distributed lines or ordered clusters).

The data generated using an array according to this invention (e.g., subcellular localization of one or more traceable translocating fusion proteins) can be analyzed using computerized systems. For instance, the array can be read by a computerized "reader" or scanner and the quantification of the location traceable signal to individual cells and/or subcellular compartments within cells on the array carried out using computer algorithms. Such analysis of the array can be referred to as "automated detection" in that the data is being gathered by an automated reader system.

In the case of labels that emit detectable electromagnetic waves or particles, the emitted light (e.g., fluorescence or luminescence) or radioactivity can be detected by sensitive cameras, confocal scanners, image analysis devices, radioactive film or a Phosphoimager, which capture the signals (such as a color image or artificial color image) from the array. A computer with image analysis software then detects this image, and analyzes the intensity and/or pattern of the signal for each cell sample location (address), and optionally individual cells within a location, in the array. Signals can be compared between locations on a single array, or between arrays (such as a single array that is sequentially analyzed at different wavelengths in order to detect the localization of different traceable fusion proteins).

Computer algorithms can also be used for comparison between spots on a single array or on multiple arrays. In addition, the data from an array can be stored in a computer readable form.

Certain examples of automated array readers (scanners) will be controlled by a computer and software programmed to direct the individual components of the reader (e.g., mechanical components such as motors, analysis components such as signal interpretation and background subtraction). Optionally software may also be provided reader to control a graphic user interface and one or more systems for sorting, categorizing, storing, analyzing, or otherwise processing the data output of the reader.

By way of example, to "read" an array that contains cells expressing a traceably labeled translocating protein (e.g., a fusion protein that contains a GFP or other fluorescent protein domain), the array can be placed into (or onto, or below, etc., depending on the location of the detector system) the reader and a traceable signal detected by the reader. These detectable signals could be associated with an address identifier signal. The reader gathers information from each of the addresses, associates it with the address identifier signal, and recognizes addresses with a detectable signal (including a particular type of signal, such as relatively intense fluorescence localized to the nucleus of the cell) as distinct from those not producing such a signal (or producing a different kind of signal, such as diffuse fluorescence in the cytoplasm of cells). Certain readers are also capable of detecting intermediate levels of signal, between no signal at all and a high signal, such that quantification of signals at individual addresses is enabled. In particularly beneficial embodiments, the reader is equipped with software that enables it to map individual cells and cell nuclei in order to determine and measure the subcellular localization of the traceable signal.

Certain readers that can be used to collect data from the arrays used with the described methods, especially those that use a fluorescently tagged fusion protein, will include a light source for optical radiation emission. The wavelength of the excitation light will usually be in the UV or visible range, but in some situations may be extended into the infra-red range. A beam splitter can direct the reader-emitted excitation beam into the object lens, which for instance may be mounted such that it can move in the x, y and z directions in relation to the surface of the array substrate. The objective lens focuses the excitation light onto the array, and more particularly onto the (microbial cell) targets on the array. Light at longer wavelengths than the excitation light is emitted from addresses on the array that contain fluorescently-labeled probe molecules (i.e., those addresses containing a cell to which the probe binds).

In certain embodiments of the invention, the array may be movably disposed within the reader as it is being read, such that the array itself moves (for instance, rotates) while the reader detects information from each address. Alternatively, the array may be stationary within the reader while the reader detection system moves across or above or around the array to detect information from the addresses of the array. Specific movable-format array readers are known and described, for instance in U.S. Pat. No. 5,922,617, hereby incorporated in its entirety by reference. Examples of methods for generating optical data storage focusing and tracking signals are also known (see, for example, U.S. Pat. No. 5,461,599).

G. Kits for Screening an Environmental Sample, and Methods of Use Thereof

It is contemplated that the fusion proteins and cells described herein can be used to screen environmental samples for the presence and/or level of one or more EDCs, which methods optionally may be carried out using kits.

In one specific contemplated example, the kits are very simple—comprising one or more water-tight container(s) in which water or other environmental samples are collected (one sample per container). In examples of this embodiment, the containers are substantially non-reactive and contain no chemicals that might be transferred into the collected sample (e.g., by leaching) and thereby detected during subsequent sample analysis. By way of example only, containers may be 500 ml (or smaller) pre-cleaned glass bottles. Optionally, such kits may include system(s) for holding the sample containers (e.g., a rack or other device, including for instance providing the containers as part of a single unit such that two or more containers are joined to each other), including for instance for holding the containers during shipping or other transportation. Sample collection containers may be joined to each other, for instance in a plate or sheet configuration. In some instances, the kits include an acidifying agent that is used to acidify the environmental samples (e.g., to pH ~3); an example of such acidifying agent is 6N hydrochloric acid (though one of ordinary skill in the art will recognize that other acidifying agents can be used). The kits may also be formatted to permit chilling of samples once they are collected, for instance chilling to about 4° C.

Capture kits of this relatively simple variety may be used in a remote-analysis system, where the samples are obtained from the environment at one location and then transported (e.g., by shipping the collected samples) to a remote location for analysis. Optionally, such kits are formatted so that the samples are shipped cold (e.g., under ice) so as to maintain a temperature of ~4° C. from soon after collection until the samples are processed for analysis at the remote location (e.g., a centralized analysis center, such as a mail-order analysis site). Kits intended for shipping to a remote analysis site optionally may be provided with mailers, such as pre-paid mailers, and/or instructions for how to ship the samples to the analysis site after collection. It is contemplated that regular sample analysis systems may be employed, for instance where a site is (or set of sites are) sampled on a regular basis and the samples returned to the same analysis site on a daily, weekly, bi-weekly, monthly, quarterly, yearly, or other regular basis. In such instances, for instance where a water processing plant or other utility or agency is taking samples, a shipping system or pick-up/delivery system can be used for transporting the samples from the collection site(s). This may enable highly reliable sample movement, while helping to keep costs down for repeat sample analysis.

Also contemplated are analysis kits, which contemplate and enable the analysis of the sample(s) without needing to engage a remote analysis site. Such kits can be used with the methods described herein to detect (and optionally quantify) one or more EDCs from samples, such as environmental samples. Such analysis kits include (for instance, in addition to one or more components of the capture kits described above—such as sample collection containers) components of a herein described system used to analyze the environmental sample, including for instance one or more (e.g., two, three, four or more) mammalian cell line(s), each of which expresses at least one traceable fusion protein. In one embodiment, the kit implements a system for detecting or quantifying a ligand of a superfamily receptor protein in a water sample, the system comprising a first mammalian cell expressing a first traceable fusion protein, a second mammalian cell expressing a second traceable fusion protein; and (optionally) a detection system for detection of the cytoplasm-to-nuclear translocation of the marker proteins (for instance, detection of the sub-cellular localization of each marker protein), wherein the first and second traceable fusion proteins independently comprise either: (1) a superfamily receptor protein, and a marker protein domain; or (2) the cytoplasmic/nuclear translocation domain of glucocorticoid receptor, the ligand binding domain of a superfamily receptor protein, and a marker protein domain. Optionally, the analysis kit comprises one or more compounds and/or compositions that stably associate with a traceable fusion protein of the kit in the absence of a ligand for the ligand binding domain of the traceable fusion protein, and which compound/composition dissociates from the fusion protein in the presence of a ligand for the ligand binding domain of the traceable fusion protein.

Specifically contemplated are kits that comprising at least four mammalian cell lines each expressing a different traceable fusion protein, wherein at least one traceable fusion protein of the kit binds a glucocorticoid, at least one traceable fusion protein of the kit binds an androgen, at least one traceable fusion protein of the kit binds a progestin, and at least one traceable fusion protein of the kit binds an aryl hydrocarbon.

Optionally, analysis kits provided herein include a portable fluorescence reader programmed to detect and monitor translocation of one or more traceable translocating fusion proteins described herein. Portable in this context may refer to a device that can readily be carried by a person into the field. However, in additional embodiments, the portable fluorescence reader is of a size that requires a transport vehicle, for instance a portable analysis van that can be moved from location to location to provide analysis of environmental samples.

Kits may be provided with instructions, for instance instructions for the collection of environmental samples, instructions for after-collection processing of the samples, for analysis of the samples to detect one or more EDCs using the systems and cells and methods described herein, and so forth. The instructions can provide calibration curves or charts to compare with the determined (e.g., experimentally measured) values.

The following example is provided to illustrate certain particular features and/or embodiments. The example should not be construed to limit the invention to the particular features or embodiments described.

Example 1

Prevalent Glucocorticoid and Androgen Activity in U.S. Water Sources

Contamination of the environment with various endocrine disrupting chemicals (EDCs) is a major health concern. The presence of estrogenic compounds in water and their deleterious effects are well documented. However, effective detection and monitoring of EDCs, including corticosteroids and androgens, is lacking.

Figure 1B:
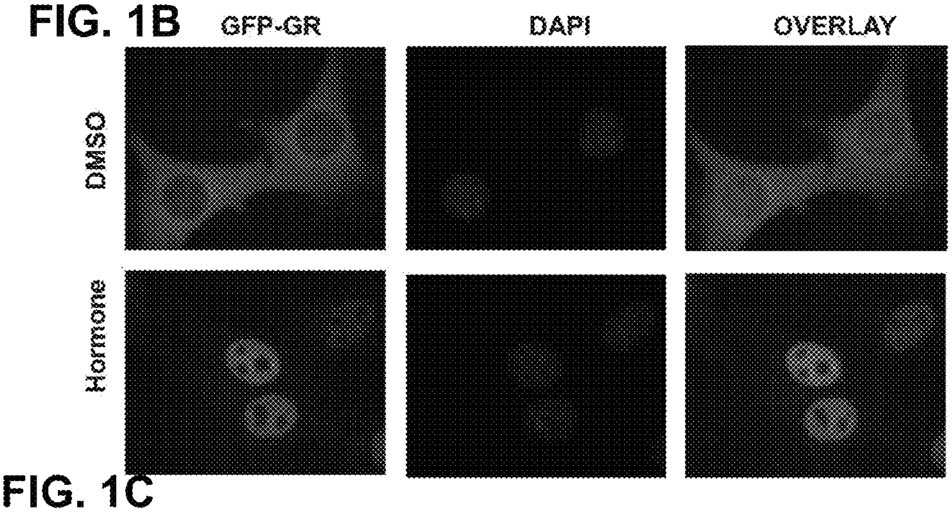

Described in this example is use of a highly sensitive live cell assay based on sub-cellular relocalization of green fluorescent protein (GFP)-tagged nuclear receptors, exemplified by the glucocorticoid receptor (GR) and androgen receptor (AR) to test samples from US water sources for hormonal activity. This assay is based on the fact that unoccupied GR resides in the cytoplasm bound to various heat-shock proteins and immunophilins in a large multi-protein complex (Pratt & Tort, *Endocr. Rev.* 18:306-360, 1997; Pratt et al., *Exp. Pharmacol.* 111-138, 2006). Upon hormone binding, GR dissociates from the chaperones and translocates to the cell nucleus (FIGS. 1A and 1B), where it interacts with GR regulatory elements (GREs) to elicit GR-specific transcription regulation. This cell based assay is used to monitor glucocorticoid and androgen activity in water samples from more than 100 locations in the Northeast United States. Using cell lines expressing GFP-tagged glucocorticoid and androgen receptors (GFP-GR and GFP-AR, respectively) in high a throughput screening, combined with studies on transcription activation, previously unrecognized glucocorticoid activity was discovered in 27%, and androgen activity in 35%, of all tested water sources from 14 states. In addition to nuclear translocation, water samples induced GR and AR-dependent gene expression. Steroids of both classes impact body development, metabolism, and interfere with reproductive, endocrine, and immune systems. This prevalent contamination could negatively affect wildlife and humans.

The levels of steroidal EDCs in the environment are not efficiently monitored and/or regulated at present. One of the reasons is that a high-throughput, reliable, and low-cost detection methods for monitoring of biologically active steroidal EDCs, including corticosteroids, have not been developed and are in demand (Roy & Pereira, *Indian J. Exp. Biol* 43:975-992, 2005).

Chemical methods for detection of EDCs reveal the presence of several classes of steroid hormones in water sources in China (Chang et al., *Environ. Sci. Technol.* 43:7691-7698, 2009). Mass spectrometry data from wastewaters in the Netherlands (Schriks et al., *Environ. Sci. Technol.* 44:4766-4774, 2010) and also China (Chang et al., *Environ. Sci. Technol.* 41:3462-3468, 2007) suggest possible contamination with glucocorticoids and a recent study demonstrated that environmentally relevant concentrations of synthetic glucocorticoids have deleterious effects on fish (Kugathas & Sumpter, *Environ. Sci. Technol.* 45:2377-2383, 2011). However, it is unclear whether in U.S. water sources are also contaminated by EDCs and to what extent. It is also unclear whether the EDCs detected in water sources could elicit steroid-specific biological response(s) in mammalian systems.

Chemical methods for EDCs detection, although sensitive, are expensive, time-consuming, and largely incompatible with a large-scale sample testing. Therefore, it is crucial to develop, test, and implement methods for high-speed, reliable, and low-cost detection of biologically active EDCs in contaminated water and other environmental sources. Here we utilize a highly sensitive cellular assay based on cytoplasm to nucleus translocation to detect glucocorticoid activity in U.S. water sources.

Materials and Methods

Samples Collection

Figure 8:
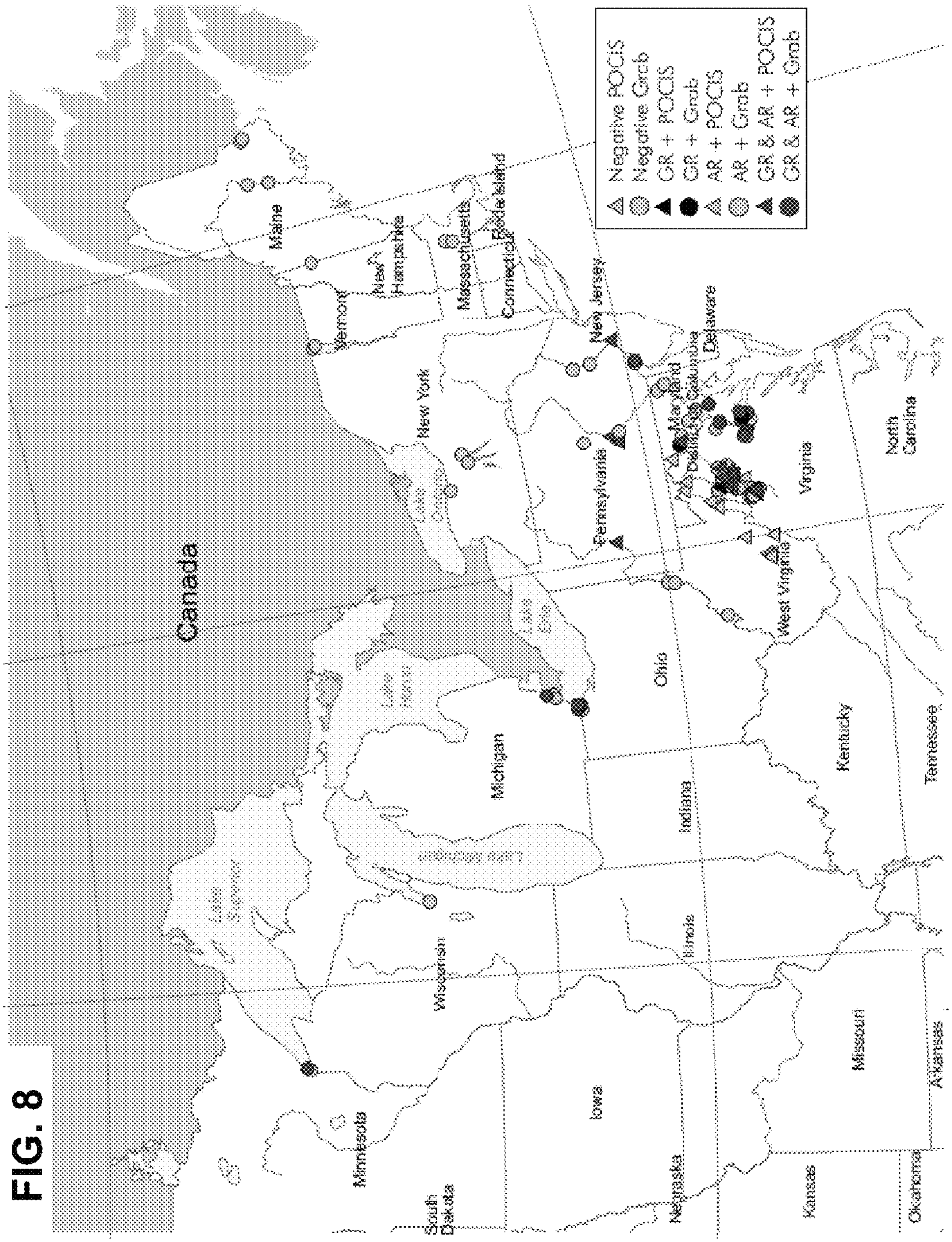
FIG. 8 illustrates geographic locations of the collection sites and their contamination with glucocorticoid and androgenic activity. Negative samples are marked with green color. Samples positive for glucocorticoid activity are marked with black, androgen activity-positive samples are marked with pink, and samples positive for both activities are marked with red. Triangles indicate grab samples, while the circles indicate the use of POCIS membranes. For complete sample description (collection method as well as the time of collection and translocation activity) see Table 5A & 5B.

Environmental water samples were collected as part of ongoing U.S. Geological Survey (USGS) projects that were implemented to monitor the presence and effects of endocrine-disruptors and other contaminants of emerging concern. They were collected between 2005 and 2010 from different geographic locations in the United States (FIG. 8), and included discrete grab water samples, or samples collected via polar organic chemical integrative samplers (POCIS) (see, Miège et al., *J. Environ. Monit.,* 14:626-635, 2012; epub Dec. 22, 2011). Samples in the R series were collected on or around National Wildlife Refuges in the Northeast and the GL series on tributaries of the Great Lakes, both were collected as part of collaborative projects with the US Fish and Wildlife Services. All other samples were collected as part of the USGS Chesapeake Bay Priority Ecosystems Science projects. Grab water samples were processed at the USGS, Leetown Science Center as described below.

POCIS samples: The POCIS membranes were shipped to the USGS, Columbia Environmental Research Center for analyte recovery. The procedures used for preparing the POCIS samples for analysis were described earlier (Alvarez et al., *Environ. Toxicol. Chem.* 28:1084-1095, 2009). Briefly, chemicals of interest were recovered from the POCIS sorbent using 50 mL of 1:1:8 (V:V:V) methanol:toluene:dichloromethane followed by 20 mL of ethyl acetate. The extracts were reduced by rotary evaporation, filtered, and composited into 2-POCIS equivalent samples thereby concentrating the amount of chemical present in each sample to aid in the detection.

Grab Water samples: Grab water samples were collected in 500 ml pre-cleaned amber glass bottles (1-Chem, Rockwood, Tenn.). Water was acidified to pH 3 using 6N hydrochloric acid, held on ice, and stored at 4° C. Within one week of collection, the preserved water samples were filtered through a GF/F filter (0.7 μm) using a solvent rinsed all-glass apparatus. Filters were rinsed with 1 ml of methanol to liberate soluble compounds from the retained suspended solids. Filtered samples and blanks were subjected to solid phase extraction (SPE) using OASIS® HLB (200 mg) glass cartridges (Waters Corporation, Milford, Mass.), following an existing protocol (Ciparis et al., *Sci. Total Environ.* 414:268-276, 2012). In short, cartridges were sequentially pre-conditioned and 400 ml of filtered samples were loaded onto the cartridge at a flow rate of 5-6 ml/minute (continuous vacuum). Analytes were eluted from the cartridge with 100% methanol and concentrated by rotary evaporation.

For biological testing, samples prepared as above were reconstituted in DMSO and diluted in growth media to a final 1,000× concentration from the original water volume while maintaining DMSO at <0.2%. Samples were added to cells for 30 minutes at 100× concentration or as indicated in the text.

Cell Lines and Translocation Assay

The 3617 and 3108 cell lines are derivatives of 3134 mouse mammary adenocarcinoma cell line that express green fluorescent protein (GFP)-tagged GR (GFP-GR) and AR (GFP-AR), respectively from a chromosomal locus under control of the tetracycline-repressible promoter (Walker et al., *Methods* (*Comp. to Meth. Enzym.*) 19:386-393, 1999; Klokk et al., *Mol. Cell. Biol.* 27:1823-1843, 2007). Prior to imaging, cells were grown overnight on 22-mm$^2$ coverslips in DMEM medium containing 10% charcoal stripped serum (Hyclone, Logan, Utah) without tetracycline (to allow the expression of the GFP-GR or GFP-AR, respectively) at a density of $2\times10^5$ per 6-well plate. For the automated experiments conducted in 96 or 384 well plates, cell density was 10,000 or 2,500 cells per well, respectively. Cells were treated with vehicle control, hormones (100 nM) or water samples for 30 min at 37° C. at a final concentration of 100× for water samples (unless otherwise specified). Additional negative controls contained samples that tested the activity of the POCIS membranes themselves.

Upon treatment, cells were fixed with 4% paraformaldehyde in PBS for 15 minutes and washed three times with PBS. Cells on the 22-mm$^2$ coverslips were mounted in VECTASHIELD® mounting media with DAPI (Vector Laboratories, Inc.) and examined on a Leica DMRA microscope with Leica 100×1.3-N.A. oil immersion objective. Images were acquired in green (GFP-GR and GFP-AR) and UV (DAPI) channel with SenSys (Photometrics) camera with KAF1400 chip configured to collect 0.067-μm-diameter pixels. For the automated experiments conducted in 96 or 384 well plates, cells were stained with DRAQ5 (BioStatus Limited) at a dilution of 1:5000 for 15 minutes and after three final washes with PBS were imaged either immediately on the Perkin Elmer Opera Image Screening System or kept in PBS at 4° C. for later imaging.

Automated Imaging and Analysis by Perkin Elmer Opera Image Screening System

A Perkin Elmer Opera Image Screening System was used for fully automated collection of fluorescence images of cells. This system employed a 40× water immersion objective lens, laser illuminated Nipkow disk, and cooled CCD cameras to digitally capture high resolution confocal fluorescence micrographs (300 nm pixel size with 2×2 camera pixel binning). An algorithm was customized using the Acapella image analysis software development kit (Perkin Elmer) to automatically segment both the nucleus and cytoplasm of each cell in the digital micrographs. The algorithm also measured the mean GFP-GR or GFP-AR intensity in both compartments, and translocation was calculated as a ratio of these intensities. Each value was further normalized to the value for the control (DMSO) sample.

Gene Transcription Analysis

For gene transcription studies, 3134 cells or LNCaP cells (expressing endogenous GR and AR, respectively) were plated in 24-well dishes 24 hours before each experiment in DMEM (3134 cells) or RPMI (LNCaP cells) media supplemented with charcoal stripped fetal bovine serum (Hyclone, Logan, Utah). Cells were treated with water samples, vehicle control (DMSO), or GR and AR specific hormones for 30 minutes. To reduce cell stress, these experiments were performed under conditions of stable $CO_2$ and temperature levels throughout the duration of an experiment (though this is not essential for the assay). Cells were lysed in 600 μl of RLT buffer (with β-mercaptoethanol added) followed by syringe/needle shearing. Total RNA was extracted using the RNeasy Mini Kit (Qiagen), including a DNaseI digestion step (RNase free DNase Set, Qiagen). One microgram (μg) of RNA was reverse transcribed (iScript cDNA Synthesis Kit, BioRad) in 20 μl reaction volume and 0.5 μl was used per Q-PCR reaction using SyBr green and Bio-Rad IQ system (BioRad, Hercules, Calif.). Primer sequences were designed to amplify nascent RNA (amplicons that cross an exon/intron boundary). The primer sequences are shown below. PCR was performed as recommended by a manufacturer. Standard curves were created by 10-fold serial dilution of template. The expression data from three or more independent experiments were normalized to the expression of a control gene β-Actin (3134 cells) and GAPDH (LNCaP cells), the mean values and SEM were calculated and displayed as a fold change in relation to the control (DMSO treated) sample.

Primer Sequences for Q-PCR Analysis

| | Sequence | SEQ ID NO: |
|---|---|---|
| Mouse cells (3134) | | |
| Per1 For | CTTCTGGCAATGGCAAGGACTC | 9 |
| Per1 Rev | CAGCATCATGCCATCATACACACA | 10 |
| Tgm2 For | TGTCACCAGGGATGAGAGACGG | 11 |
| Tgm2 Rev | TCCAAATCACACCTCTCCAGGAG | 12 |
| Lcn2 For | ACCTCTCATTTCTTGCAGTTCCG | 12 |
| Lcn2 Rev | CAGGATGGAGGTGACATTGTAGCT | 13 |
| β-Actin For | AGTGTGACGTTGACATCCGTA | 15 |
| β-Actin Rev | GCCAGAGCAGTAATCTCCTTCT | 16 |
| Human cells (LNCaP) | | |
| hNKX3.1 For | TGACAGTGGGCTGTTTGTTC | 17 |
| hNKX3.1 Rev | AAGACCCCAAGTGCCTTTCT | 18 |
| hRHOU For | TTTCAAGGATGCTGGCTCTT | 19 |
| hRHOU Rev | GGCCTCAGCTTGTCAAATTC | 20 |
| GAPDH For | AAGGTGAAGGTCGGAGTCAAC | 21 |
| GAPDH Rev | GGGGTCATTGATGGCAACAATA | 22 |

Statistical Analyses

Data were analyzed using the statistical functions of IBM SPSS Statistics 19 and SigmaPlot 11 (SPSS Inc., Chicago, Ill.). From the repeated experiments, the mean value was calculated for each sample. The mean values were used in a one-way analysis of variance test. If a significant F-value of $P<0.05$ was obtained, a Dunnett's multiple comparison versus the control group analysis was conducted.

TABLE 2

Collection sites and collection time of the first sample set.

| Samples | Date/year | Location | Collection method |
|---|---|---|---|
| Blank | Oct.-Nov. 2005 | | POCIS |
| WV2 | Oct.-Nov. 2005 | South Branch Potomac, Franklin, WV | POCIS |
| WV3 | Oct.-Nov. 2005 | South Branch Potomac, Springfield, WV | POCIS |
| WV4 | Oct.-Nov. 2005 | South Branch Potomac, Moorefield, WV | POCIS |
| WV5 | Oct.-Nov. 2005 | Elk River, WV | POCIS |
| WV6 | Oct.-Nov. 2005 | South Branch Potomac, Petersburg Gap, WV | POCIS |
| WV7 | Oct.-Nov. 2005 | Greenbrier River, WV | POCIS |
| SS83 | Jun. 1, 2007 | | POCIS |
| SS92 | May 3, 2007-Jun. 7, 2007 | Gauley River, WV | POCIS |
| SS93 | Apr. 11, 2007-May 9, 2007 | Lower Conococheague River, MD | POCIS |
| SS94 | Apr. 11, 2007-May 9, 2007 | Upper Conococheague River, MD | POCIS |
| SS95 | Apr. 27, 2007-May 31, 2007 | South Branch Potomac, Petersburg Gap, WV | POCIS |
| SS97 | Apr. 11, 2007-May 9, 2007 | Lower Monocacy River, MD | POCIS |
| SS98 | Apr. 5, 2007-May 9, 2007 | South Fork, Shenandoah River, VA | POCIS |

TABLE 3

Synthetic glucocorticoids surveyed by monitoring the mass spectrometric data for the presence of the corresponding molecular ion in sample SS97

| | |
|---|---|
| 1 | amcinonide |
| 2 | betamethasone |
| 3 | budesonide |
| 4 | clobetasone |
| 5 | clobetasol |
| 6 | propionate |
| 7 | desonide |
| 8 | fluocinonide |
| 9 | fluocinolone acetonide |
| 10 | fluocortolone |
| 11 | fluprednidene acetate |
| 12 | halcinonide |
| 13 | hydrocortisone |
| 14 | hydrocortisone-17-butyrate |
| 15 | methylprednisolone |
| 16 | mometasone |
| 17 | mometasone furoate |
| 18 | prednicarbate |
| 19 | prednisolone |
| 20 | prednisone |
| 21 | triamcinolone acetonide |

TABLE 4

Figure 1C:
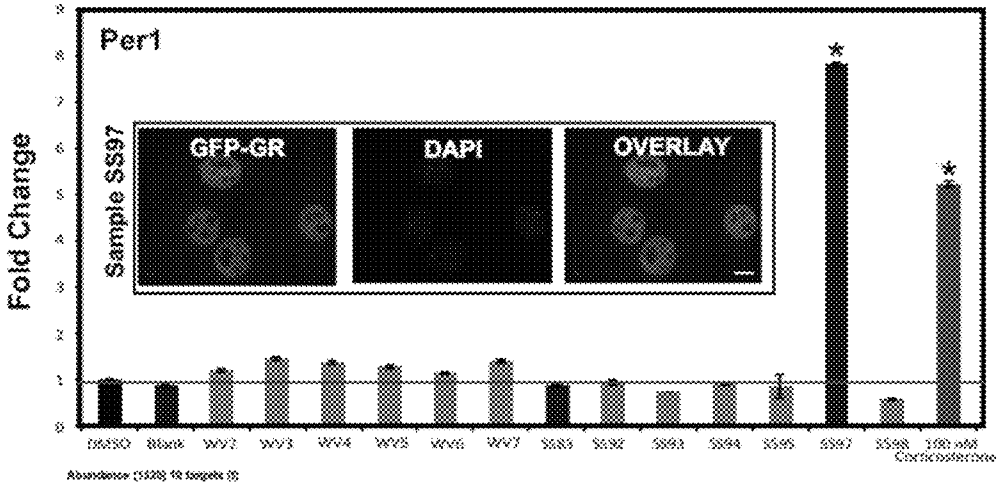
Figure 1D:
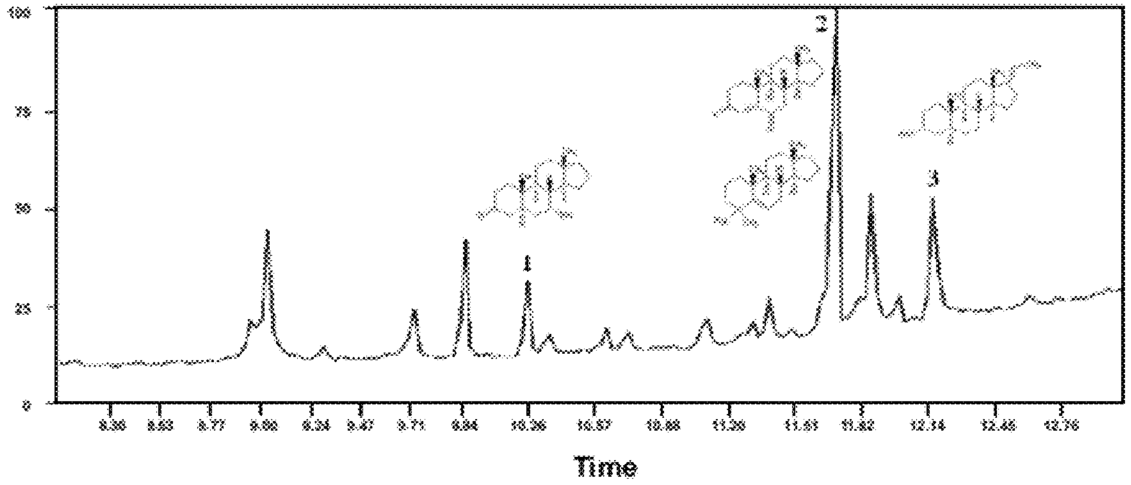

Closest EIMS library matches of the mass spectra of chromatographic peaks 1-3 in FIG. 1D.

| Peak # | ~Ob-served MW | Closest EIMS Library Match | Structure |
|---|---|---|---|
| 1 | 272 | 7α-Hydroxy-5α-androstan-3-one MW 290 | 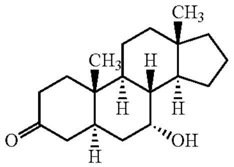 |
| 2 | 286 | Androst-4-en-3,6-dione MW 286 | 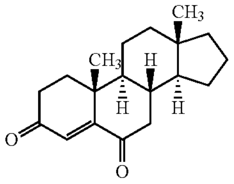 |

TABLE 4-continued

Closest EIMS library matches of the mass spectra of chromatographic peaks 1-3 in FIG. 1D.

| Peak # | ~Ob-served MW | Closest EIMS Library Match | Structure |
|---|---|---|---|
| | | or 4,4-Dimethyl-androst-5-ene MW 286 | 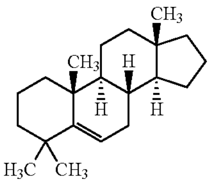 |
| 3 | 272 ? | eα-Hydroxy-17-ethylidene-5α-androstane MW 302 | 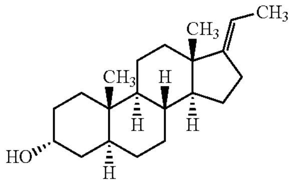 |

Table 5A-5B contains information about additional samples tested for GFP-GR and GFP-AR translocation efficiency.

TABLE 5A

Geographic location, time and methods of collection of the water samples.

| Samples | Date/year | Location | Collection method |
|---|---|---|---|
| | | Plate 1 | |
| R1 | Sept. 2, 2008 | Ohio River, Wheeling WV | Grab sample |
| R2 | Sept. 3, 2008 | Ohio River, Parkersburg, WV | Grab sample |
| R3 | Sept. 3, 2008 | Upstream Brighton Dam, Tridelphia reservoir, MD | Grab sample |
| R4A | Sept. 10, 2008 | Patuxent/Western Branch, MD | Grab sample |
| R4E | Sept. 10, 2008 | Patuxent/Western Branch, MD (WWTP effluent) | Grab sample |
| R5 | Sept. 15, 2008 | Seneca River, NY | Grab sample |
| R6 | Sept. 16, 2008 | Seneca River, NY | Grab sample |
| R7 | Sept. 22, 2008 | St. Croix River, ME | Grab sample |
| R8 | Sept. 23, 2008 | St. Croix River, ME | Grab sample |
| R9 | Oct. 2, 2008 | Sudbury river, MA | Grab sample |
| R10 | Oct. 3, 2008 | Sudbury river, MA | Grab sample |
| R13 | Oct. 15, 2008 | Rappahanock River, VA | Grab sample |
| R14 | Oct. 15, 2008 | Rappahanock River, VA | Grab sample |
| R15 | Oct. 6, 2008 | Rappahanock River, VA | Grab sample |
| R16 | Oct. 27, 2008 | Darby Creek, PA | Grab sample |
| R16W | Oct. 27, 2008 | Darby Creek, PA (WWTP effluent) | Grab sample |
| R21 | Sept. 1, 2009 | Missisquoi River, VT | Grab sample |
| R22 | Sept. 1, 2009 | Missisquoi River, VT | Grab sample |
| R22W | Sept. 1, 2009 | Missisquoi River, VT (WWTP effluent) | Grab sample |
| R23 | Sept. 14, 2009 | Penobscot River, ME | Grab sample |
| R24 | Sept. 15, 2009 | Penobscot River, ME | Grab sample |
| R26 | Sept. 22, 2009 | Peconic Lake, NY | Grab sample |
| R27 | Sept. 28, 2009 | Potomac River, Pohick, VA | Grab sample |
| R27W | Sept. 28, 2009 | Potomac River, Pohick, VA (WWTP effluent) | Grab sample |
| R28 | Sept. 29, 2009 | Burke Lake, VA | Grab sample |
| R29 | Oct. 5, 2009 | Delaware River, Cherry Valley, DE | Grab sample |
| R30 | Oct. 6, 2009 | Delaware River, Easton, PA | Grab sample |
| R31 | Oct. 13, 2009 | Susquehanna River, Garret Island, PA | Grab sample |
| R32 Broad | Oct. 14, 2009 | Susquehanna River, Conowingo Dam, PA | Grab sample |
| R32 CON | Oct. 14, 2009 | Susquehanna River, Conowingo Dam, PA | Grab sample |
| PSS2a | May 14, 2010 | Gooney Run, VA | Grab sample |
| PSS2b | Jun. 14, 2010 | Gooney Run, VA | Grab sample |
| PSS3a | May 14, 2010 | Passage Creek, VA | Grab sample |
| PSS3b | Jun. 15, 2010 | Passage Creek, VA | Grab sample |
| PSS4a | May 14, 2010 | Stony Creek (upstream), VA | Grab sample |
| PSS4b | Jun. 15, 2010 | Stony Creek (upstream), VA | Grab sample |
| PSS5a | May 14, 2010 | Stony Creek (downstream), VA | Grab sample |
| PSS5b | Jun. 15, 2010 | Stony Creek (downstream), VA | Grab sample |
| PSS6a | May 13, 2010 | Mill Creek, VA | Grab sample |

TABLE 5A-continued

Geographic location, time and methods of collection of the water samples.

| Samples | Date/year | Location | Collection method |
| --- | --- | --- | --- |
| PSS6b | Jun. 14, 2010 | Mill Creek, VA | Grab sample |
| PSS7a | May 14, 2010 | Hawksbill Creek, VA | Grab sample |
| PSS7b | Jun. 14, 2010 | Hawksbill Creek, VA | Grab sample |
| PSS8a | May 13, 2010 | Smith Creek (downstream), VA | Grab sample |
| PSS8b | Jun. 14, 2010 | Smith Creek (downstream), VA | Grab sample |
| PSS9a | May 12, 2010 | Naked Creek, VA | Grab sample |
| PSS9b | Jun. 15, 2010 | Naked Creek, VA | Grab sample |
| PSS10a | May 13, 2010 | Briery Branch, VA | Grab sample |
| PSS10b | Jun. 15, 2010 | Briery Branch, VA | Grab sample |
| PSS11a | May 13, 2010 | Smith Creek (upstream), VA | Grab sample |
| PSS11b | Jun. 14, 2010 | Smith Creek (upstream), VA | Grab sample |
| PSS12a | May 13, 2010 | Long Glade Creek, VA | Grab sample |
| PSS12b | Jun. 14, 2010 | Long Glade Creek, VA | Grab sample |
| PSS13a | May 13, 2010 | Linville Creek, VA | Grab sample |
| PSS13b | Jun. 14, 2010 | Linville Creek, VA | Grab sample |
| PSS14a | May 13, 2010 | Long Meadow Run, VA | Grab sample |
| PSS14b | Jun. 14, 2010 | Long Meadow Run, VA | Grab sample |
| PSS15a | May 13, 2010 | Muddy Creek, VA | Grab sample |
| PSS15b | Jun. 15, 2010 | Muddy Creek, VA | Grab sample |
| PSS16a | May 12, 2010 | Cooks Creek, VA | Grab sample |
| PSS16b | Jun. 14, 2010 | Cooks Creek, VA | Grab sample |
| Dairy | Sept. 28, 2010 | North Fork Shenandoah at Woodstock, VA | Grab sample |
| LF1a | Oct. 15, 2008 | WWTP1 effluent, Rappahannock river, Little Falls, VA | Grab sample |
| LF2a | Oct. 15, 2008 | WWTP2 effluent, Rappahannock river, Little Falls, VA | Grab sample |
| LF3a | Oct. 15, 2008 | WWTP3 effluent, Rappahannock river, Little Falls, VA | Grab sample |
| LF4a | Oct. 15, 2008 | WWTP4 effluent, Rappahannock river, Little Falls, VA | Grab sample |
| SUS1 | May 12, 2009 | Susquehanna river at Mahantango Access, PA | Grab sample |
| SUS2 | May 13, 2009 | West Branch Susquehanna river, PA | Grab sample |
| | | Plate 2 | |
| SUS5 | Apr. 21, 2010-Jun. 1, 2010 | Juniata River, Newport, PA | POCIS |
| SUS6 | Apr. 21, 2010-Jun. 1, 2010 | Susquehanna River at Mahantango Creek, PA | POCIS |
| DE1 | Apr. 19, 2010-Jun. 3, 2010 | Delaware River, Yardley, PA | POCIS |
| AL1 | Apr. 28, 2010-Jun. 7, 2010 | Allegheny River, Kittanning, PA | POCIS |
| PSS16 | May 12, 2010-Jun. 14, 2010 | Cooks Creek, VA | POCIS |
| PSS09 | May 12, 2010-Jun. 15, 2010 | Naked Creek, VA | POCIS |
| PSS15 | May 13, 2010-Jun. 15, 2010 | Muddy Creek, VA | POCIS |
| PSS10 | May 13, 2010-Jun. 15, 2010 | Briery Branch, VA | POCIS |
| PSS12 | May 13, 2010-Jun. 14, 2010 | Long Glade Creek, VA | POCIS |
| PSS11 | May 13, 2010-Jun. 14, 2010 | Smith Creek (upstream), VA | POCIS |
| PSS13 | May 13, 2010-Jun. 14, 2010 | Linville Creek, VA | POCIS |
| PSS14 | May 13, 2010-Jun. 14, 2010 | Long Meadow Run, VA | POCIS |
| PSS08 | May 13, 2010-Jun. 14, 2010 | Smith Creek (downstream), VA | POCIS |
| PSS06 | May 13, 2010-Jun. 14, 2010 | Mill Creek, VA | POCIS |
| PSS02 | May 14, 2010-Jun. 14, 2010 | Gooney Run, VA | POCIS |
| PSS07 | May 14, 2010-Jun. 14, 2010 | Hawksbill Creek, VA | POCIS |
| PSS03 | May 14, 2010-Jun. 14, 2010 | Passage Creek, VA | POCIS |
| PSS05 | May 14, 2010-Jun. 14, 2010 | Stony Creek (downstream), VA | POCIS |
| PSS04 | May 14, 2010-Jun. 14, 2010 | Stony Creek (upstream), VA | POCIS |
| FAB | Jun. 1, 2010 | Blank | POCIS |
| 1FB | Jun. 1, 2010 | Blank | POCIS |
| 2FB | Jun. 1, 2010 | Blank | POCIS |
| 3FB | Jun. 1, 2010 | Blank | POCIS |
| 4FV | Jun. 1, 2010 | Blank | POCIS |
| 5FB | Jun. 1, 2010 | Blank | POCIS |
| 6FB | Jun. 1, 2010 | Blank | POCIS |

TABLE 5A-continued

| Geographic location, time and methods of collection of the water samples. | | | |
|---|---|---|---|
| Samples | Date/year | Location | Collection method |
| 7FB | Jun. 1, 2010 | Blank | POCIS |
| 8FB | Jun. 1, 2010 | Blank | POCIS |
| 9FB | Jun. 1, 2010 | Blank | POCIS |
| 10FB | Jun. 1, 2010 | Blank | POCIS |
| 11FB | Jun. 1, 2010 | Blank | POCIS |
| 12FB | Jun. 1, 2010 | Blank | POCIS |
| 13FB | Jun. 1, 2010 | Blank | POCIS |
| 14FB | Jun. 1, 2010 | Blank | POCIS |
| 15FB | Jun. 1, 2010 | Blank | POCIS |
| 16FB | Jun. 1, 2010 | Blank | POCIS |
| 17FB | Jun. 1, 2010 | Blank | POCIS |
| 18FB | Jun. 1, 2010 | Blank | POCIS |
| 19FB | Jun. 1, 2010 | Blank | POCIS |
| BLANK | Jun. 1, 2010 | Blank | POCIS |
| R38 | Sept. 20, 2010 | PA Erie (Pond H) | Grab sample |
| R39 | Sept. 28, 2010 | NJ Great Swamp (Hidden Valley Nursery) | Grab sample |
| R40 | Oct. 4, 2010 | VA Back Bay | Grab sample |
| R41 | Oct. 5, 2010 | VA Wilna Pond | Grab sample |
| R42 | Oct. 6, 2010 | VA Chandler's Mill Pond | Grab sample |
| R43 | Oct. 13, 2010 | MD Patuxent (Snowden Pond) | Grab sample |
| R44 | Oct. 13, 2010 | MD Patuxent (Cash Lake) | Grab sample |
| GL1 | Oct. 1, 2010 | Genesee River, NY | Grab sample |
| GL2W | Oct. 1, 2010 | St. Louis River, Duluth, MN (WWTP effluent) | Grab sample |
| GL2P | Oct. 1, 2010 | St. Louis River, Duluth, MN (Power Plant effluent) | Grab sample |
| GL5 | Oct. 1, 2010 | Fox river, Green Bay, WI | Grab sample |
| GL4CSOa | Oct. 1, 2010 | Swan Creek, Ohio | Grab sample |
| GL4CSOb | Oct. 1, 2010 | Swan Creek, Ohio | Grab sample |
| GL4CSOc | Oct. 1, 2010 | Swan Creek, Ohio | Grab sample |
| GL3a | Oct. 1, 2010 | Detroit River, MI | Grab sample |
| GL3b | Oct. 1, 2010 | Detroit River, MI | Grab sample |
| GL3c | Oct. 1, 2010 | Detroit River, MI | Grab sample |
| R36 | Sept. 14, 2010 | Missisquoi River (Gander Bay & Goose Bay), VT | Grab sample |
| R37 | Sept. 16, 2010 | Lake Umbagog, MA | Grab sample |

TABLE 5B

Activity of the samples in the GFP-GR and GFP-AR translocation assays (P < 0.01 and P < 0.05, asterisks).

| Samples | GR translocation P < 0.01 | GR translocation P < 0.05 | AR translocation P < 0.01 | AR translocation P < 0.05 |
|---|---|---|---|---|
| Plate 1 | | | | |
| R1 | FALSE | FALSE | FALSE | FALSE |
| R2 | FALSE | FALSE | FALSE | FALSE |
| R3 | FALSE | FALSE | FALSE | FALSE |
| R4A | * | * | * | * |
| R4E | * | * | * | * |
| R5 | FALSE | FALSE | FALSE | FALSE |
| R6 | FALSE | FALSE | FALSE | FALSE |
| R7 | FALSE | FALSE | FALSE | FALSE |
| R8 | FALSE | FALSE | * | * |
| R9 | FALSE | FALSE | * | * |
| R10 | FALSE | FALSE | * | * |
| R13 | FALSE | FALSE | FALSE | FALSE |
| R14 | FALSE | FALSE | FALSE | FALSE |
| R15 | FALSE | FALSE | * | * |
| R16 | FALSE | FALSE | * | * |
| R16W | * | * | FALSE | * |
| R21 | FALSE | FALSE | FALSE | FALSE |
| R22 | FALSE | FALSE | FALSE | FALSE |
| R22W | FALSE | FALSE | FALSE | FALSE |
| R23 | FALSE | FALSE | FALSE | FALSE |
| R24 | FALSE | FALSE | FALSE | FALSE |
| R26 | FALSE | FALSE | FALSE | FALSE |
| R27 | * | * | FALSE | FALSE |
| R27W | FALSE | FALSE | FALSE | FALSE |
| R28 | FALSE | FALSE | FALSE | FALSE |
| R29 | FALSE | FALSE | FALSE | FALSE |
| R30 | FALSE | FALSE | FALSE | FALSE |

TABLE 5B-continued

Activity of the samples in the GFP-GR and GFP-AR translocation assays (P < 0.01 and P < 0.05, asterisks).

| Samples | GR translocation P < 0.01 | GR translocation P < 0.05 | AR translocation P < 0.01 | AR translocation P < 0.05 |
|---|---|---|---|---|
| R31 | FALSE | FALSE | FALSE | FALSE |
| R32 Broad | FALSE | FALSE | FALSE | FALSE |
| R32 CON | FALSE | FALSE | FALSE | FALSE |
| PSS2a | FALSE | FALSE | FALSE | FALSE |
| PSS2b | FALSE | FALSE | FALSE | FALSE |
| PSS3a | FALSE | FALSE | FALSE | FALSE |
| PSS3b | FALSE | FALSE | FALSE | FALSE |
| PSS4a | FALSE | FALSE | FALSE | FALSE |
| PSS4b | FALSE | FALSE | FALSE | FALSE |
| PSS5a | FALSE | FALSE | FALSE | FALSE |
| PSS5b | FALSE | FALSE | FALSE | FALSE |
| PSS6a | FALSE | FALSE | FALSE | FALSE |
| PSS6b | FALSE | FALSE | * | * |
| PSS7a | FALSE | FALSE | FALSE | FALSE |
| PSS7b | FALSE | FALSE | FALSE | FALSE |
| PSS8a | FALSE | FALSE | FALSE | FALSE |
| PSS8b | FALSE | FALSE | FALSE | FALSE |
| PSS9a | FALSE | FALSE | FALSE | FALSE |
| PSS9b | FALSE | FALSE | FALSE | FALSE |
| PSS10a | FALSE | FALSE | FALSE | FALSE |
| PSS10b | FALSE | FALSE | FALSE | FALSE |
| PSS11a | FALSE | FALSE | FALSE | FALSE |
| PSS11b | FALSE | FALSE | FALSE | * |
| PSS12a | FALSE | FALSE | FALSE | FALSE |
| PSS12b | FALSE | FALSE | * | * |
| PSS13a | FALSE | FALSE | FALSE | FALSE |
| PSS13b | FALSE | FALSE | * | * |
| PSS14a | FALSE | FALSE | FALSE | FALSE |
| PSS14b | FALSE | FALSE | * | * |

TABLE 5B-continued

Activity of the samples in the GFP-GR and GFP-AR translocation assays (P < 0.01 and P < 0.05, asterisks).

| | GR translocation | | AR translocation | |
|---|---|---|---|---|
| Samples | P < 0.01 | P < 0.05 | P < 0.01 | P < 0.05 |
| PSS15a | FALSE | FALSE | * | * |
| PSS15b | FALSE | FALSE | FALSE | FALSE |
| PSS16a | FALSE | FALSE | FALSE | FALSE |
| PSS16b | FALSE | FALSE | * | * |
| Dairy | FALSE | FALSE | FALSE | FALSE |
| LF1a | FALSE | * | * | * |
| LF2a | * | * | * | * |
| LF3a | * | * | FALSE | FALSE |
| LF4a | * | * | FALSE | * |
| SUS1 | FALSE | FALSE | FALSE | FALSE |
| SUS2 | FALSE | FALSE | FALSE | FALSE |
| | | Plate2 | | |
| SUS5 | * | * | * | * |
| SUS6 | * | * | * | * |
| DE1 | * | * | * | * |
| AL1 | * | * | * | * |
| PSS16 | * | * | * | * |
| PSS09 | * | * | * | * |
| PSS15 | * | * | * | * |
| PSS10 | * | * | * | * |
| PSS12 | * | * | * | * |
| PSS11 | * | * | FALSE | * |
| PSS13 | * | * | * | * |
| PSS14 | * | * | * | * |
| PSS08 | * | * | FALSE | * |
| PSS06 | * | * | * | * |
| PSS02 | * | * | * | * |
| PSS07 | * | * | * | * |
| PSS03 | FALSE | FALSE | FALSE | FALSE |
| PSS05 | * | * | * | * |
| PSS04 | * | * | FALSE | FALSE |
| FAB | FALSE | FALSE | FALSE | FALSE |
| 1FB | FALSE | FALSE | FALSE | FALSE |
| 2FB | FALSE | FALSE | FALSE | FALSE |
| 3FB | FALSE | FALSE | FALSE | FALSE |
| 4FV | FALSE | FALSE | FALSE | FALSE |
| 5FB | FALSE | FALSE | FALSE | FALSE |
| 6FB | FALSE | FALSE | FALSE | FALSE |
| 7FB | FALSE | FALSE | FALSE | FALSE |
| 8FB | FALSE | FALSE | FALSE | FALSE |
| 9FB | FALSE | FALSE | FALSE | FALSE |
| 10FB | FALSE | FALSE | FALSE | FALSE |
| 11FB | FALSE | FALSE | FALSE | FALSE |
| 12FB | FALSE | FALSE | FALSE | FALSE |
| 13FB | FALSE | FALSE | FALSE | FALSE |
| 14FB | FALSE | FALSE | FALSE | FALSE |
| 15FB | FALSE | FALSE | FALSE | FALSE |
| 16FB | FALSE | FALSE | FALSE | FALSE |
| 17FB | FALSE | FALSE | FALSE | FALSE |
| 18FB | FALSE | FALSE | FALSE | FALSE |
| 19FB | FALSE | FALSE | FALSE | FALSE |
| BLANK | FALSE | FALSE | FALSE | FALSE |
| R38 | FALSE | FALSE | FALSE | FALSE |
| R39 | FALSE | FALSE | FALSE | FALSE |
| R40 | FALSE | FALSE | FALSE | FALSE |
| R41 | FALSE | FALSE | FALSE | FALSE |
| R42 | FALSE | FALSE | FALSE | FALSE |
| R43 | FALSE | FALSE | FALSE | FALSE |
| R44 | FALSE | FALSE | FALSE | FALSE |
| GL1 | FALSE | FALSE | FALSE | FALSE |
| GL2W | * | * | FALSE | * |
| GL2P | FALSE | FALSE | FALSE | FALSE |
| GL5 | FALSE | FALSE | FALSE | FALSE |
| GL4CSOa | FALSE | * | * | * |
| GL4CSOb | * | * | * | * |
| GL4CSOc | FALSE | FALSE | * | * |
| GL3a | FALSE | FALSE | FALSE | FALSE |
| GL3b | FALSE | FALSE | FALSE | FALSE |
| GL3c | * | * | FALSE | FALSE |
| R36 | FALSE | FALSE | FALSE | FALSE |
| R37 | FALSE | FALSE | FALSE | FALSE |

Results & Discussion

Figure 2A:
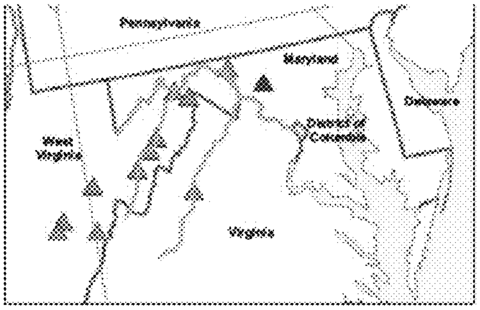
FIG. 2A-C illustrates collection sites of the first sample set and testing of HPLC fractions from sample SS97 for GR translocation.
Figure 2B:
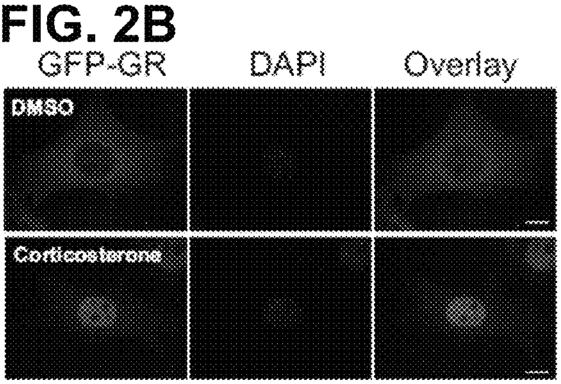

Accumulated data hint at an unacknowledged and potentially wide spread contamination with glucocorticoids (GCs) at biologically-relevant concentrations. To directly examine this possibility, 10 water samples collected from different locations (FIG. 2A and Table 2) were tested for GC activity using GFP-GR translocation assay. The presence of GC activity in one of these samples (SS97) was revealed by the accumulation of GFP-GR in the nucleus within 30 minutes (FIG. 1C, images). Furthermore, this sample induced transcriptional activity as measured by an increase of the nascent transcript of the GR-regulated gene, Per1, to a significantly higher level than the positive control, corticosterone (at a physiologically relevant dose of 100 nM) (FIG. 1C, graph).

Figure 2C:
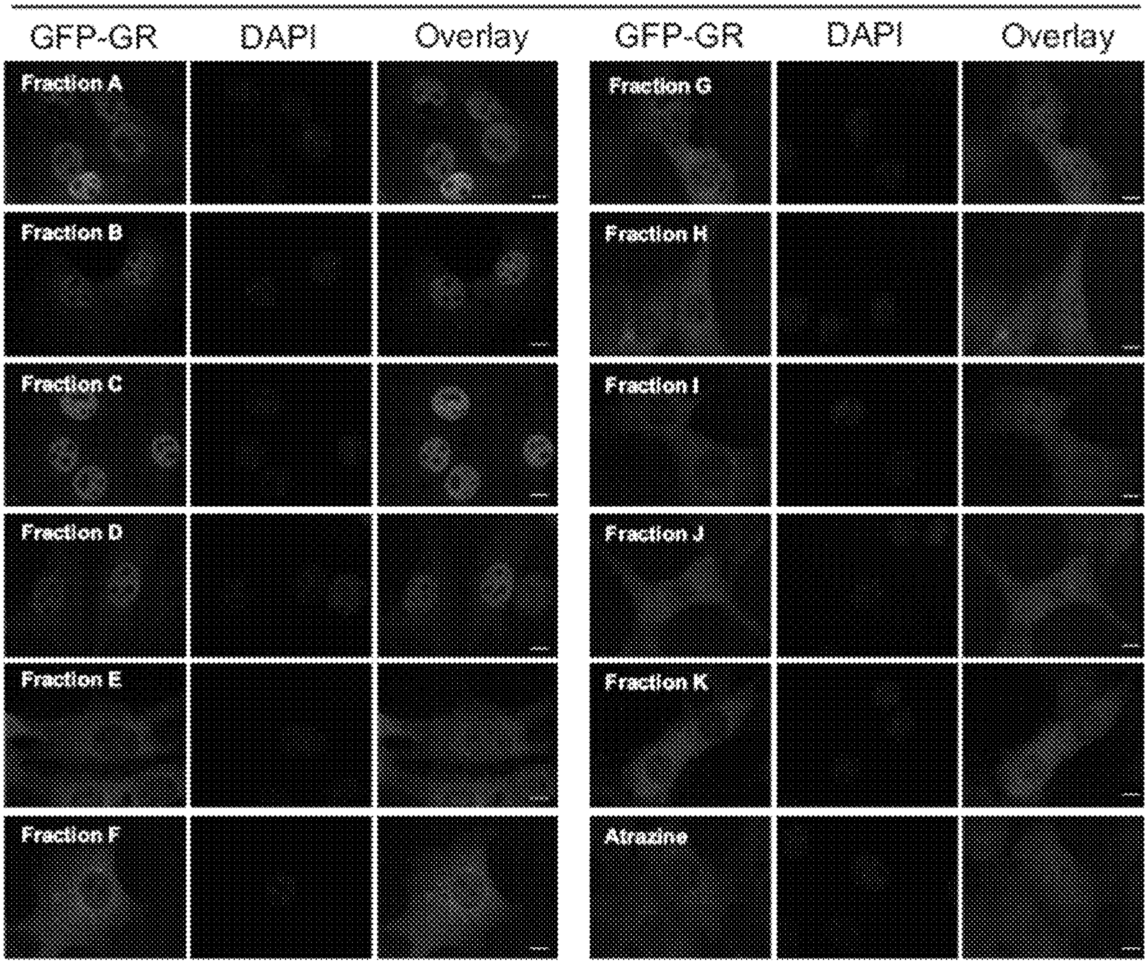

In an attempt to determine the active constituent(s) in sample SS97, known corticosteroids (dexamethasone and corticosterone) were tested by high performance liquid chromatography/mass spectrometry (HPLC/MS) analysis to establish chromatographic retention times on a C18 HPLC column using published techniques (Chang et al., *Environ. Sci. Technol.* 43, 7691-7698, 2009). In addition, 20 other synthetic GCs were surveyed by monitoring the mass spectrometric data for the presence of the corresponding molecular ions (Table 3). Under these assay conditions, sample SS97 showed no evidence of any known compounds tested. Next, sample SS97 was subjected to HPLC fractionation followed by biological testing. Four of the eleven HPLC fractions showed activity in the nuclear translocation assay (FIG. 2C). Again, when these fractions were tested by ultra-performance liquid chromatography/mass spectrometry (UPLC/MS), no known GCs compounds were detected. The active fractions were also analyzed by gas chromatography/MS (GC/MS) (Mansilha et al., *J. Chromatogr. A* 1217(43):6681-6691, 2010), and appeared similar in composition to volatile components. The mass spectra extracted from the GC/MS analysis were searched in both the NIST/EPA/NIH Mass Spectral Library 1998 and in the Wiley Mass Spectra Database of Androgens, Estrogens, and other Steroids 2010 (AES 2010), yielding no hits of high certainty for any of the peaks.

Visual comparison of the mass spectra of chromatographic peaks 1-3 (FIG. 1D) with standard spectra from the AES 2010 database (FIG. 3) suggested similarities to known androstane-class compounds (FIG. 1D, Table 4). One of these compounds, androst-4-en-3,6-dione (peak 2), was synthesized (Hunter & Priest, *Steroids* 71, 30, 2006) and further tested for biological activity. Androst-4-en-3,6-dione did not induce GFP-GR translocation (data not shown) whereas it induced GFP-tagged androgen receptor (GFP-AR) translocation (FIG. 1E) using a GFP-AR expressing cell line, 3108 (Klokk et al., *Mol. Cell. Biol.* 27:1823-1843, 2007). These data suggest that, in addition to GCs, sample SS97 also contains androgenic activity.

Figure 1E:
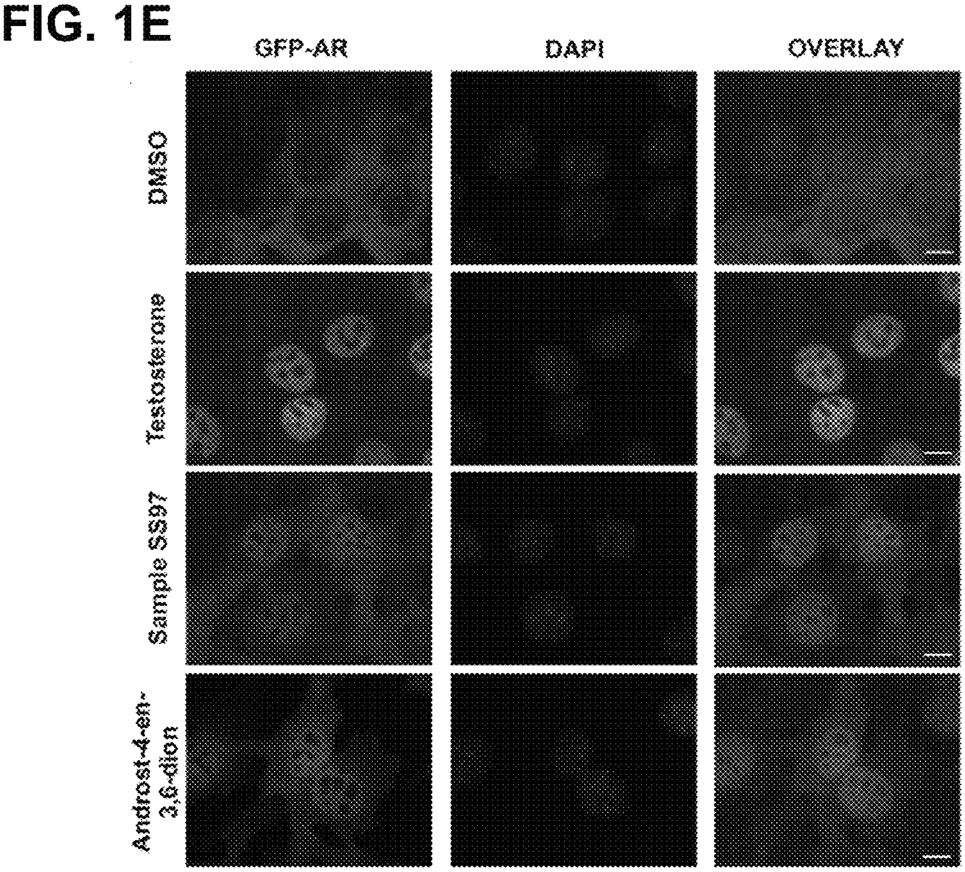

Androgens are the original anabolic steroids and the precursor of all estrogens, the female sex hormones. Through their binding to androgen receptor (AR), they control the development and maintenance of male characteristics in vertebrates (Gottlieb et al., *Reprod. Biomed. Online.* 10:42-48, 2005). Similarly to the GR, AR is largely cytoplasmic in the absence of its ligand, and rapidly translocates to the nucleus in response to testosterone (Klokk et al., *Mol. Cell. Biol.* 27:1823-1843, 2007) (FIG. 1E).

We conclude that environmental degradation and metabolic processes alter the structure of the glucocorticoid(s) in water samples, producing bioactive chemical structures which are not contained in the existing databases. Rapid transformation of hormonal steroids by aquatic microorganisms has been reported previously (Yin et al., *Environ. Int.* 28:545-551, 2002). We also conclude that, in contrast to the traditional chemical analysis, the translocation assay described herein is faster, cheaper, and also detects biologically relevant hormonal activity which cannot readily be discerned by chemical methods. Translocation assay allows unbiased "non-candidate" approach for detection of EDCs and could be used in a powerful combination with fractionation methods and "forensic chemistry" in the discovery of novel bioactive ligands.

Figure 3:
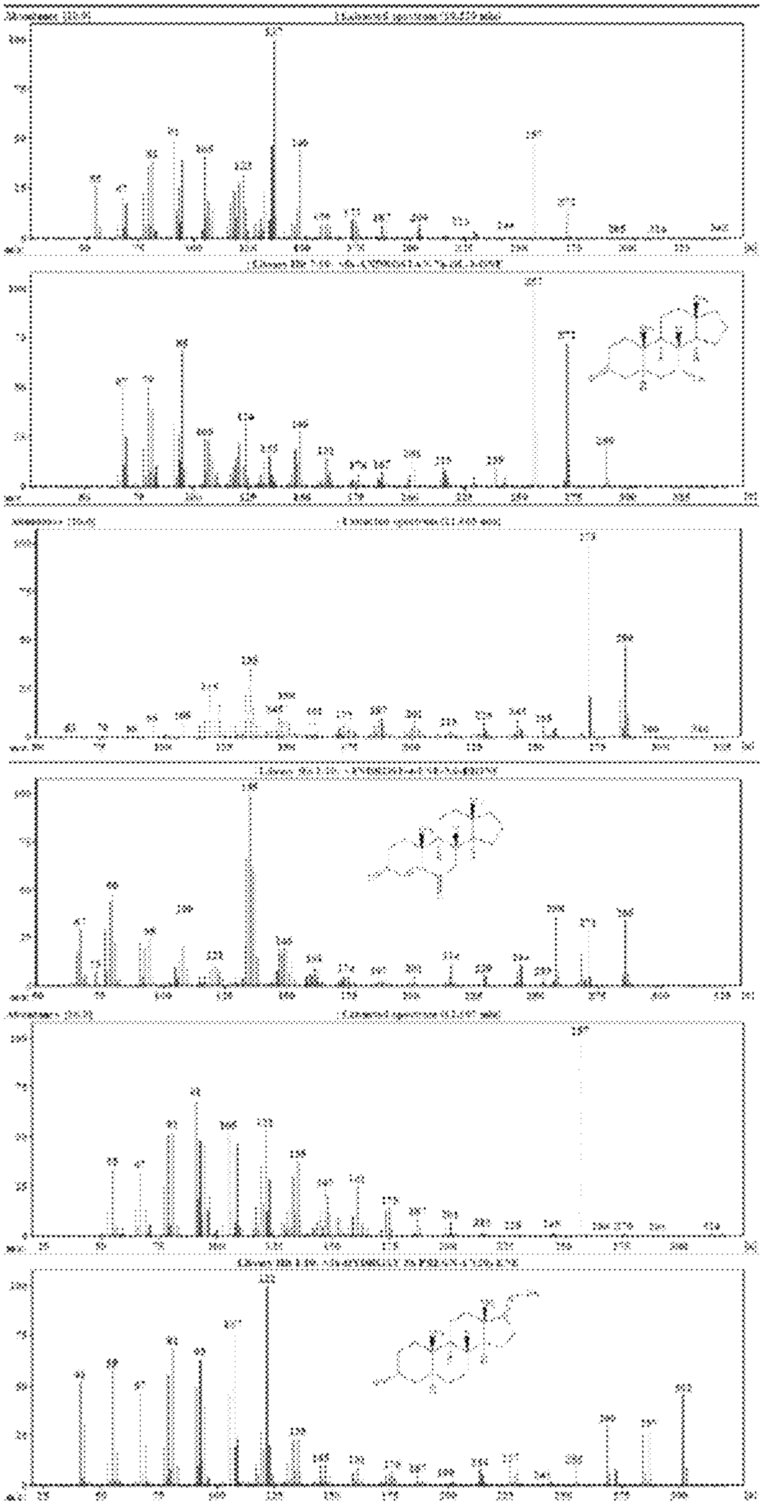
FIG. 3 illustrates that database searching of the extracted MS chromatographic peaks 1-3 (FIG. 1D) suggests that the compounds were similar in structure to known androstane-type steroids. Visual comparison of the mass spectra of chromatographic peaks 1-3 (FIG. 1D) with standard spectra from the AES 2010 database suggests similarities to known androstane-class compounds.
Figure 4D:
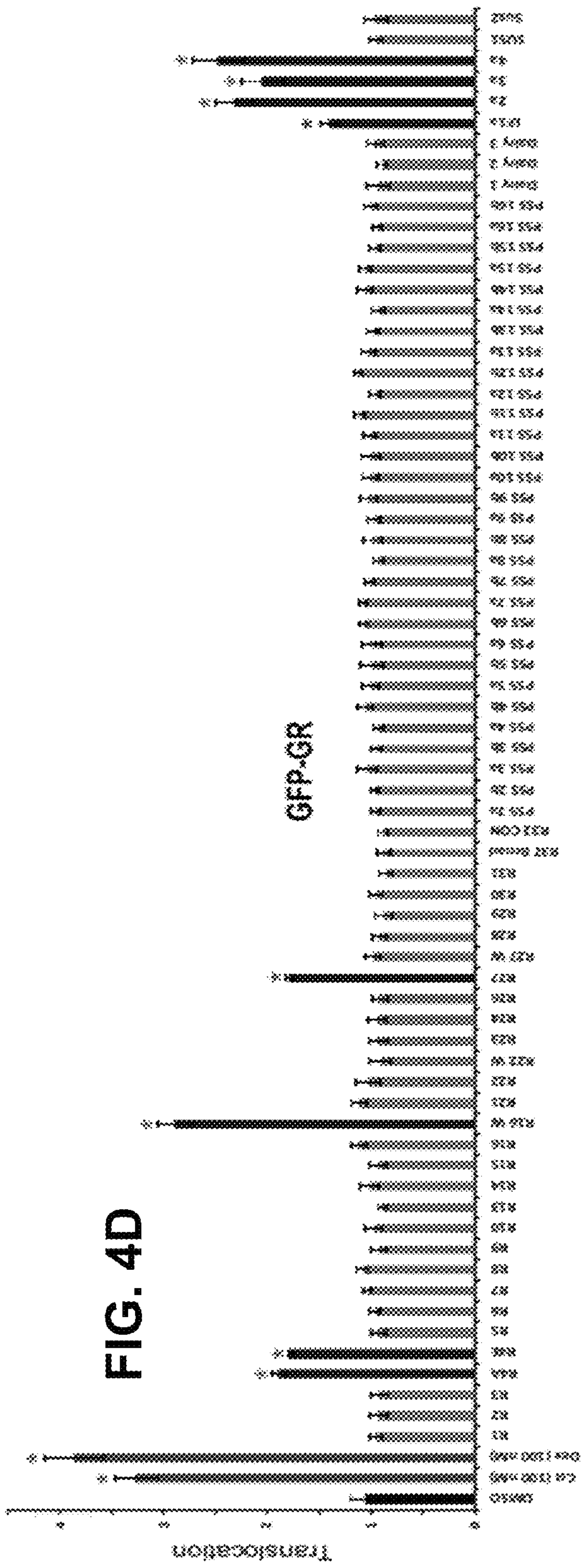
Figure 4E:
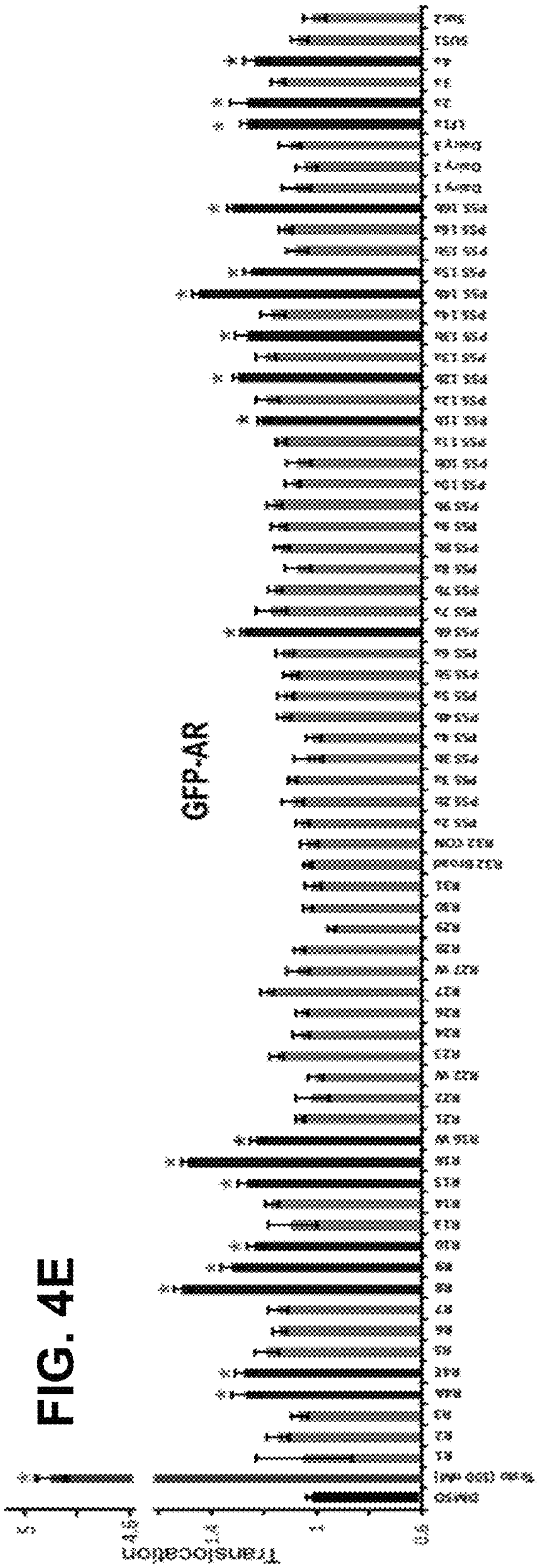
Figure 5A:
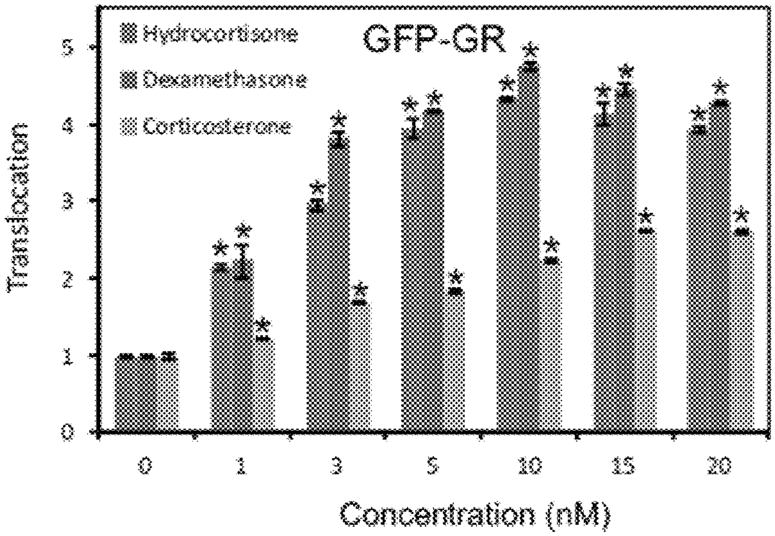
FIG. 5A-C illustrates concentration-dependent translocation of GFP-GR and GFP-AR in response to their respective hormones as detected by the Opera (Perkin Elmer) automated imaging analysis system.
Figure 5B:
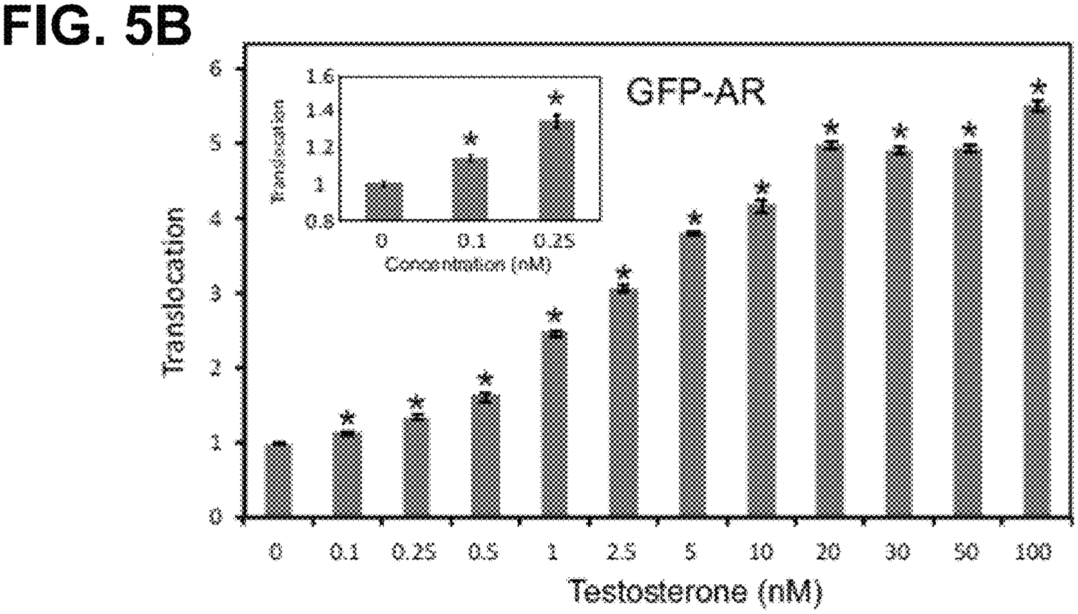
Figure 5C:
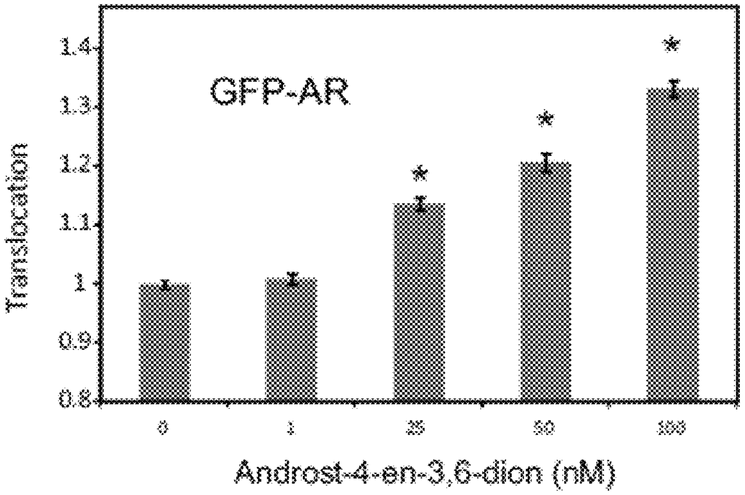
Figure 6A:
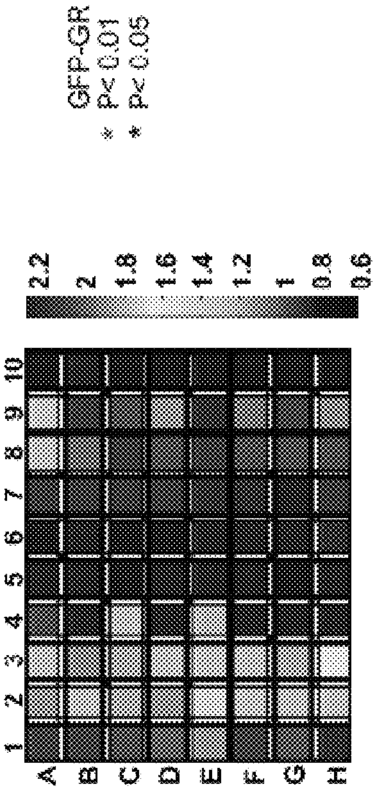
FIG. 6A-B illustrates additional samples screened for GFP-GR nuclear translocation.
Figure 6B:
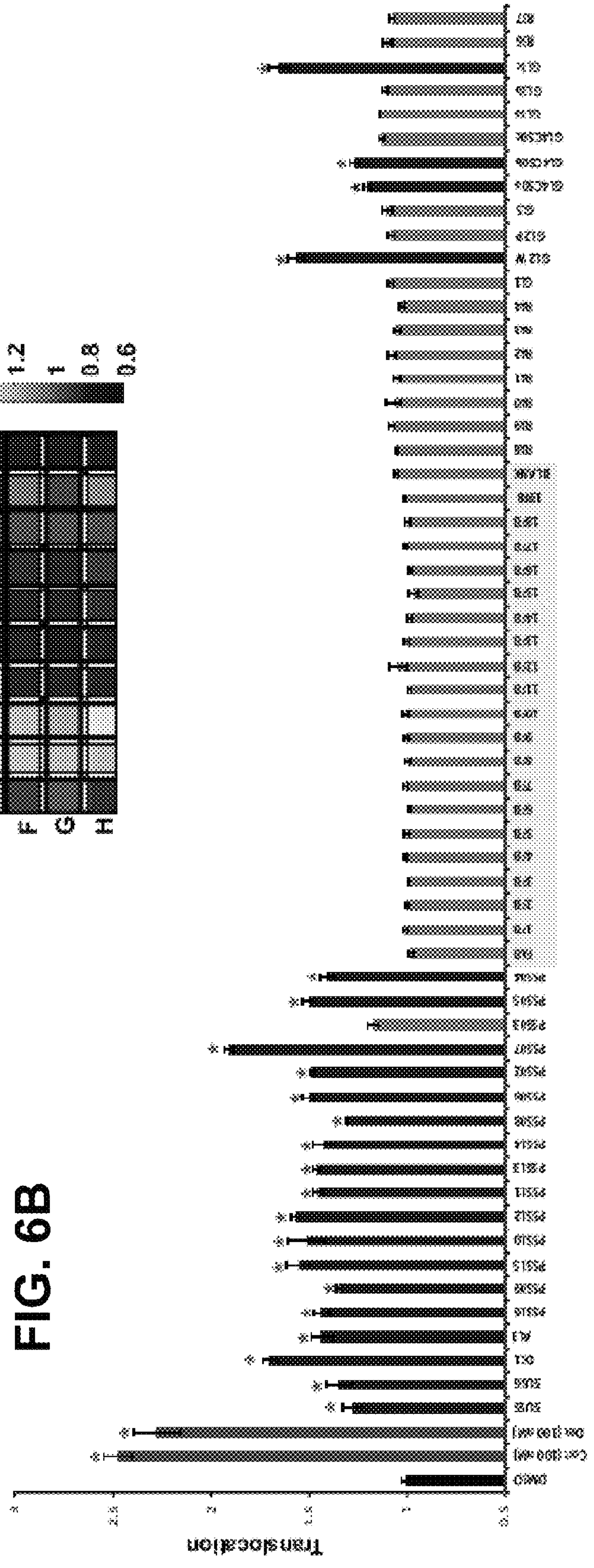
Figures 7A, 7B:
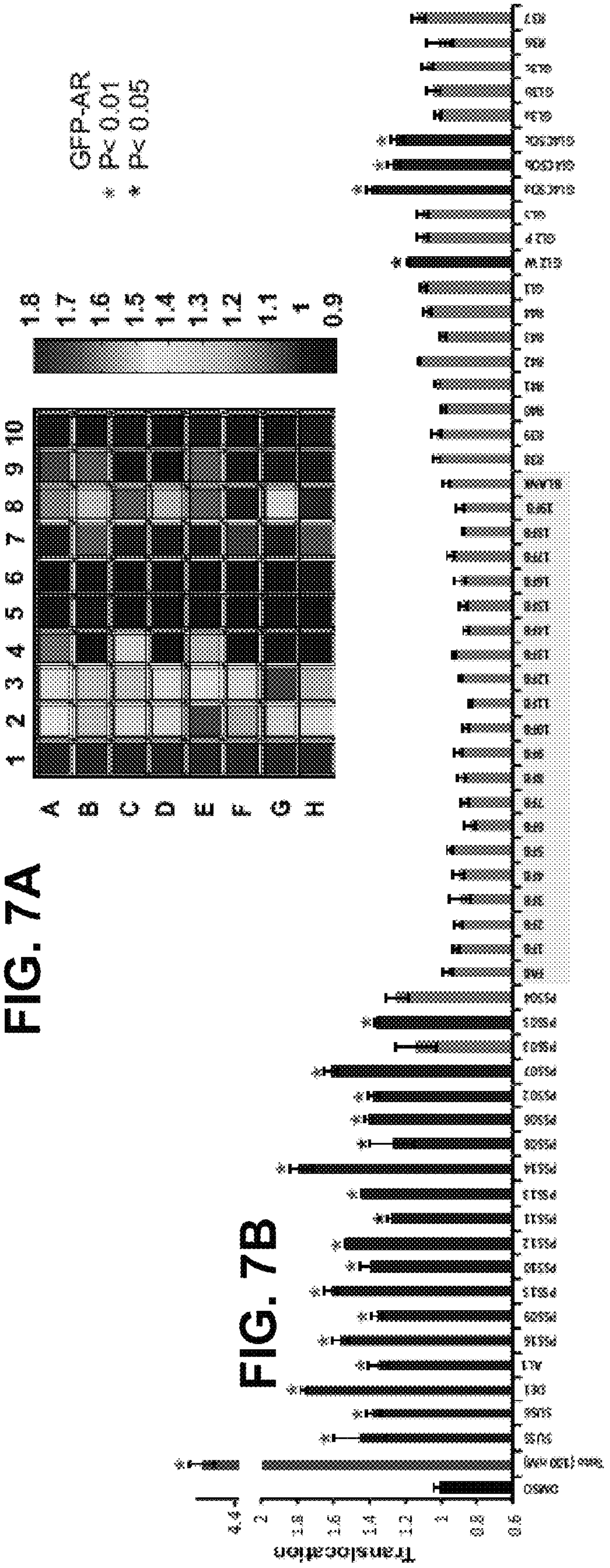
FIG. 7A-B illustrates additional samples screened for GFP-AR nuclear translocation.

Next, the search was expanded to screen over 100 additional samples from water sources throughout 14 states in the US (Table 5A) for both, glucocorticoid and androgen activities. To accomplish this screening, the GFP-GR- and GFP-AR-expressing cell lines (Walker et al., *Methods* (*Comp. to Meth. Enzym.*) 19:386-393, 1999; Klokk et al., *Mol. Cell. Biol.* 27:1823-1843, 2007) were implemented in an automated imaging analysis system (Perkin Elmer Opera Image Screening System) and an algorithm for cytoplasm and nuclear segmentation was used to calculate translocation efficiency (FIGS. 4A and 4B). To test the sensitivity and reproducibility of the automated assay, translocation efficiency in response to known concentrations of the respective hormones was measured. GFP-GR translocated to the nucleus in a concentration-dependent manner in response to the rodent, human, as well as synthetic hormones (corticosterone, hydrocortisone, and dexamethasone, respectively) (FIG. 5A). The GFP-tagged AR also translocated to the nucleus in concentration-dependent manner in response to testosterone as well as synthesized androst-4-en-3,6-dione (FIGS. 5B and 5C). Confident in the sensitivity of the translocation assay, the additional water samples were tested after being divided into two plates: plate one [P1, (FIGS. 4D, 4E)] and plate two [P2, (FIGS. 6 and 6)]. Glucocorticoid activity was evident in over 28% (FIG. 4D and FIG. 6) and androgen activity in 37% (FIG. 4E and FIG. 7) of the 105 samples subjected to the high throughput screening (Tables 5A and 5B). When combined with the results obtained from the first manual screen of 10 samples (Table 2), glucocorticoid and androgen activity remained in the same range (27% and 35%, respectively). These results unambiguously demonstrate a wide spread contamination of the US water sources from 14 different states with both, glucocorticoid and androgenic activities (FIG. 3, Tables 5A and 5B).

Figure 9A:
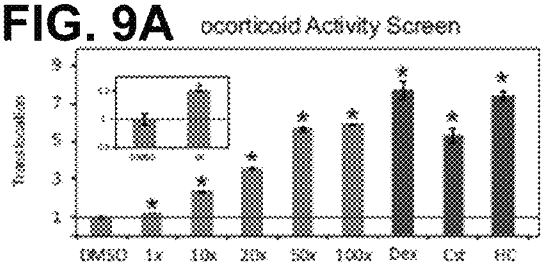
FIG. 9A-F illustrates concentration-dependent translocation and transcriptional activation induced by newly collected grab samples at location SS97.
Figure 9B:
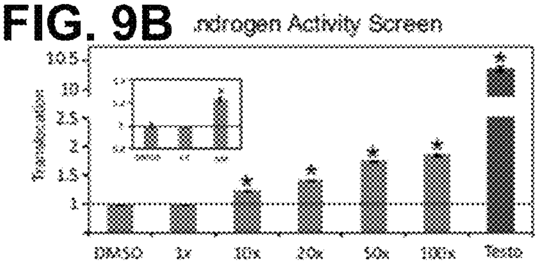
Figure 9C:
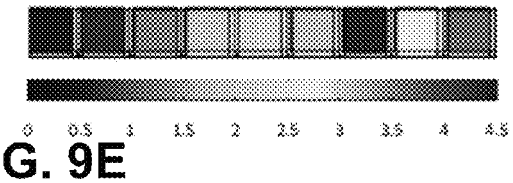
Figure 9D:
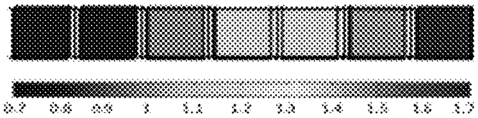
Figure 9E:
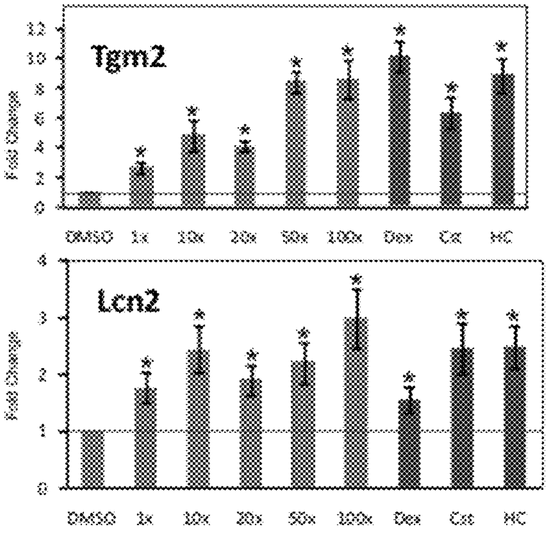

Considering that the tested samples were collected over a span of several years (Tables 2 and 5A), we sought to determine whether the observed contaminations persist over time. Two of the previously identified contaminated sites (SS97 and GL2W) were revisited and new grab water samples were collected. As shown in FIGS. 4A and B (as well as in FIGS. S6, S7, S8, S9) both newly collected samples induced GFP-GR and GFP-AR nuclear translocation in a concentration-dependent manner, suggesting high and persisting water contamination at these sites. Tenfold concentrated samples from both locations were active in GR and AR translocation assays, and induced transcriptional activity. Moreover, at 1× concentration, sample SS97 induced significant GFP-GR translocation (FIG. 9A-*insert*) and activation of gene transcription from GR-responsive genes (FIG. 9E). These results indicate that the water at the SS97 location has biologically relevant glucocorticoid activity that is persistent over time.

Figure 9F:
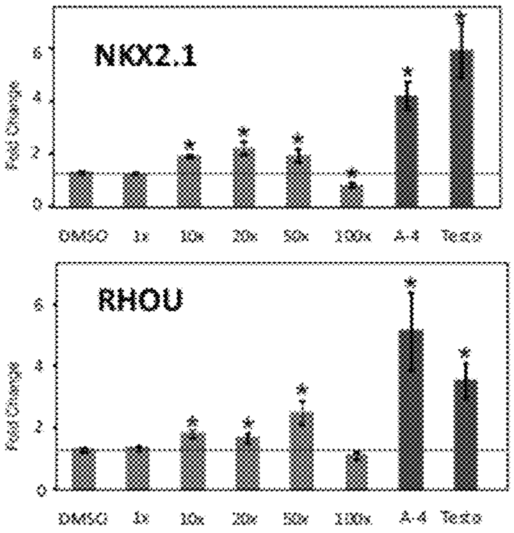
Figures 10A, 10B:
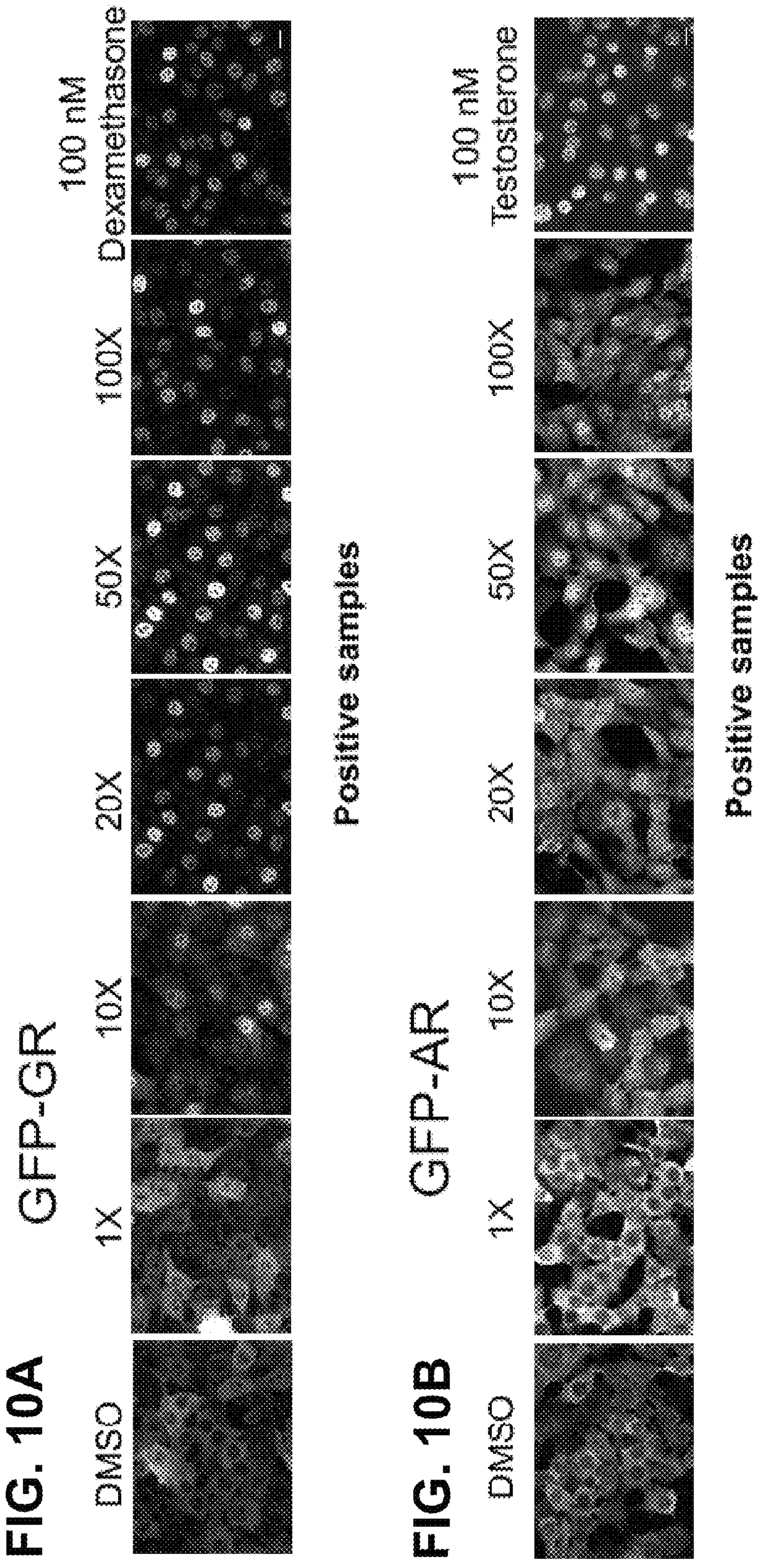
FIG. 10A-B illustrates concentration-dependent GFP-GR and GFP-AR translocation induced by the newly collected sample from the same location as SS97.
Figures 11A, 11B:
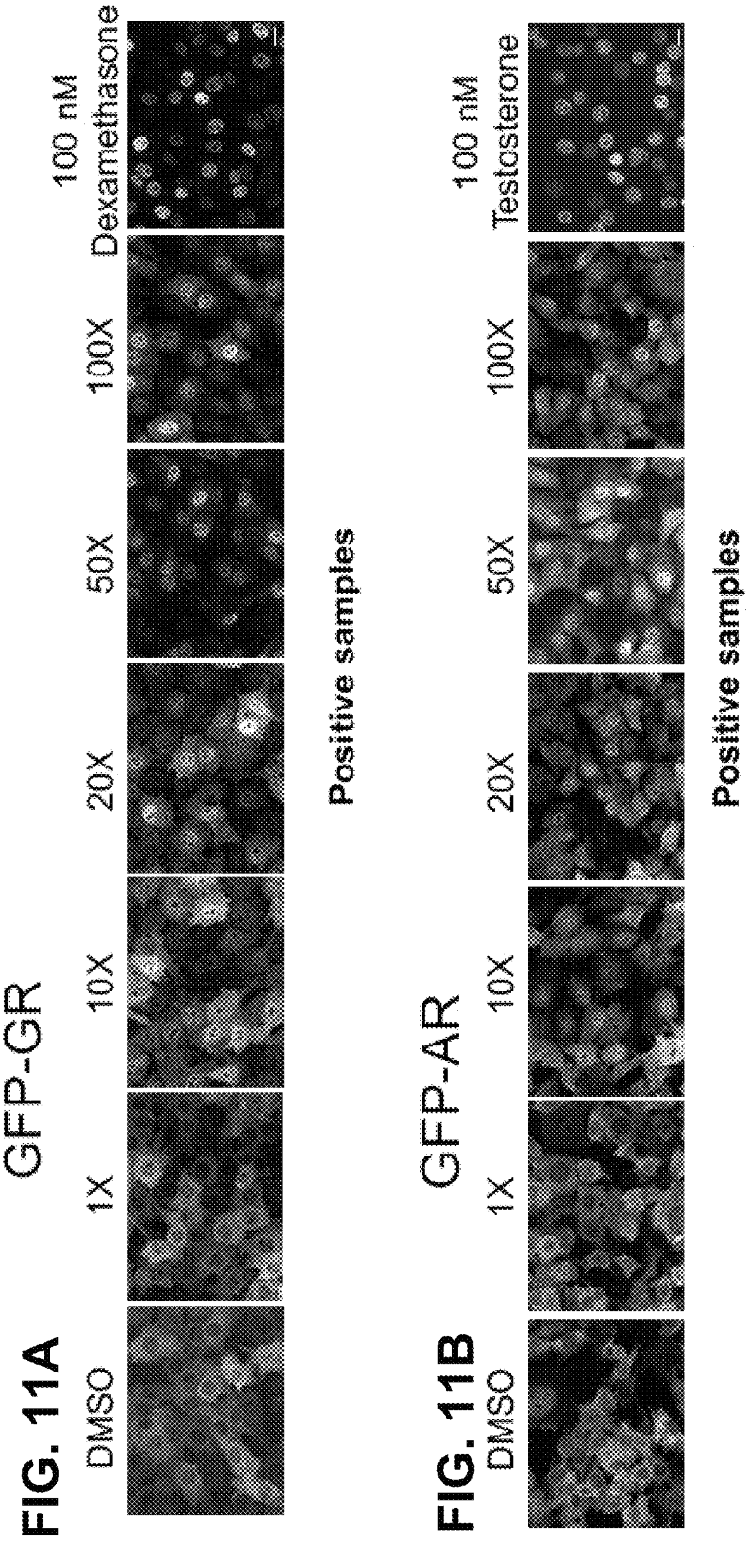
FIG. 11A-B illustrates concentration-dependent GFP-GR and GFP-AR translocation induced by the newly collected sample from the same location as GL2W.
Figure 12A:
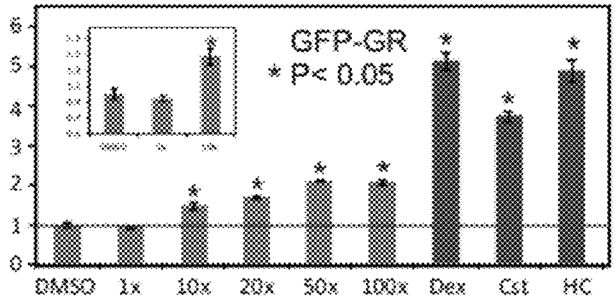
FIG. 12A-C illustrates concentration-dependent GFP-GR translocation and transcriptional activation of GR-regulated genes in response to the newly collected sample from the same location as GL2W.
Figure 12B:
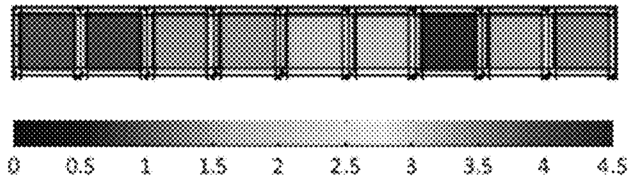
Figure 12C:
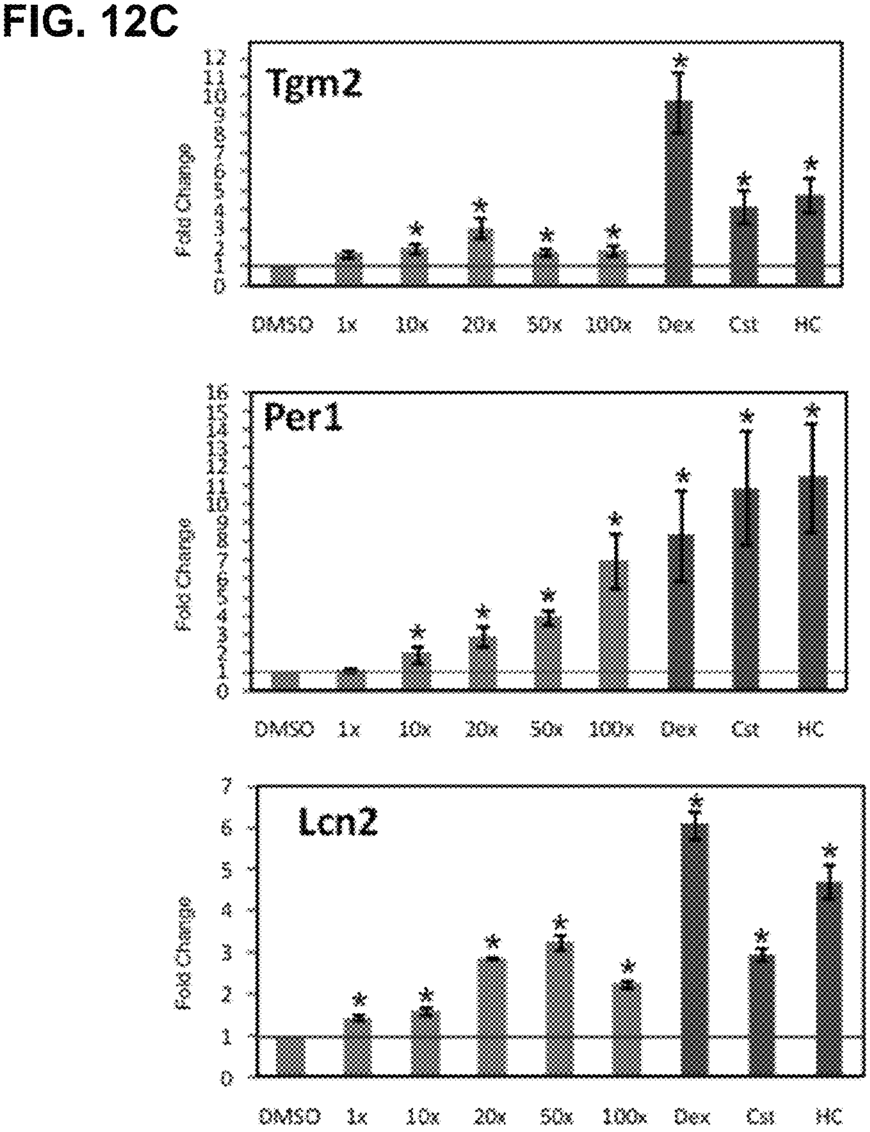
Figure 13A:
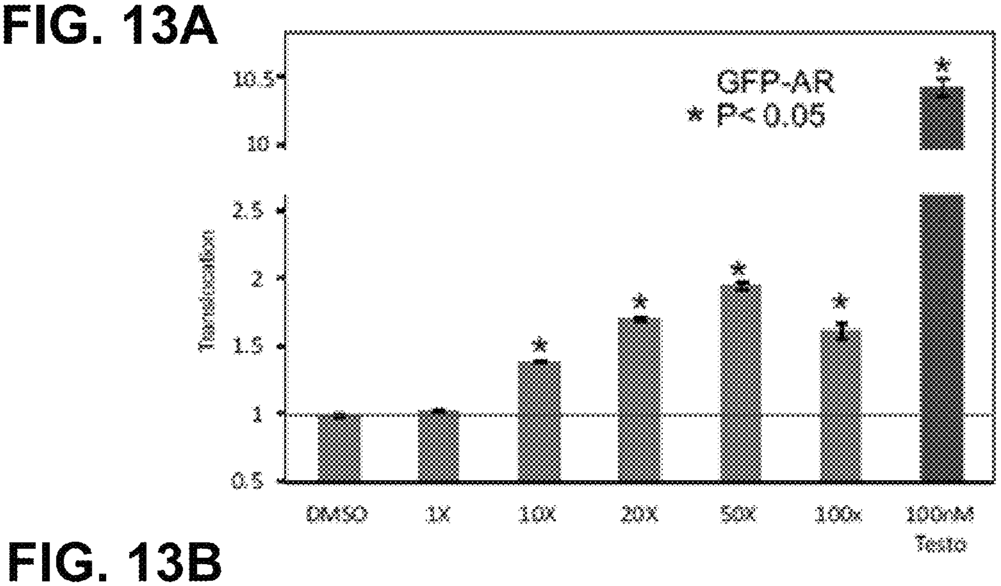
FIG. 13A-C illustrates concentration-dependent GFP-AR translocation and transcriptional activation of AR-regulated genes in response to the newly collected sample from GL2W site.
Figure 13B:
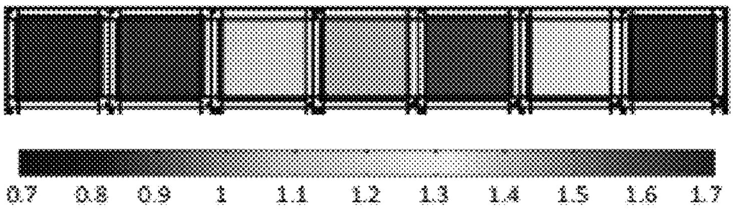
Figure 13C:
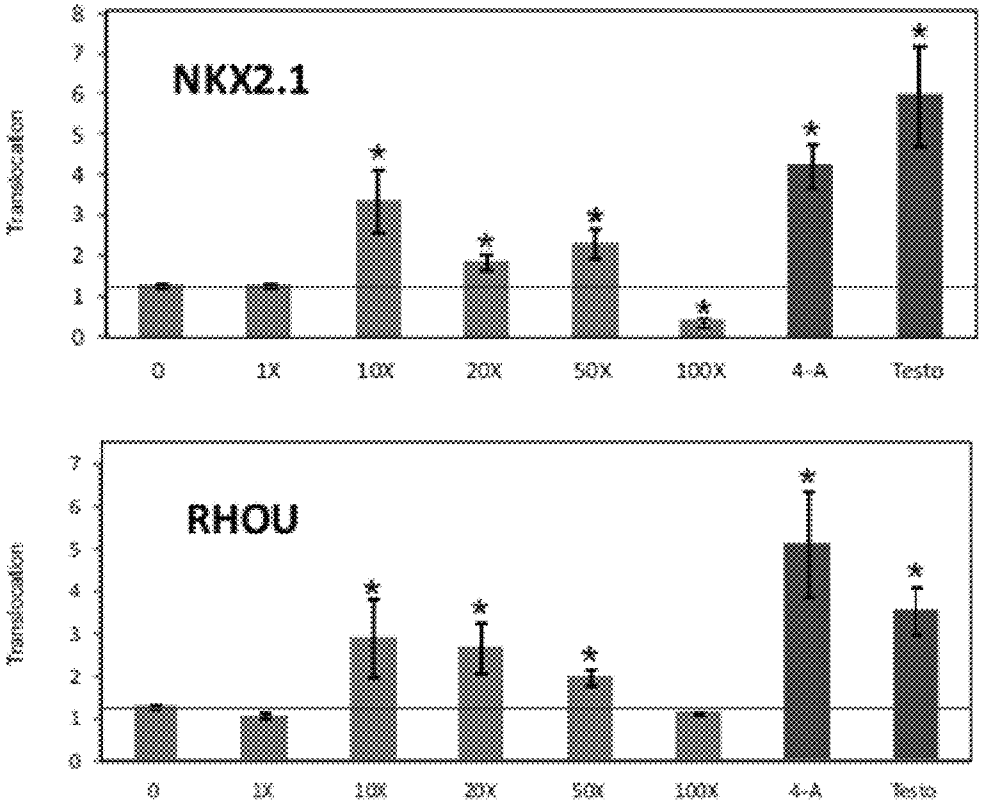

Interestingly, 100× concentration of samples SS97 (FIG. 9F) and GL2W (FIG. 13C) were less potent than the lower doses in inducing gene transcription from AR-regulated genes. This could be an example of the well-known phenomenon of non-monotonic dose-response where the effects of the low doses of EDCs cannot be predicted by the effects observed at high doses (Vandenberg et al., *Endocr. Rev.*, e-published ahead of printing on Mar. 14, 2012 as doi: 10.1210/er.2011-1050). These results underscore the importance of examining the effects of a range of concentrations when using gene transcription analyses as a readout for the biological effect of EDCs. However, presence of inhibitory components or anti-estrogens cannot be ruled out and may warrant further investigation. In contrast, the GFP-GR and GFP-AR translocation assays were applicable to a wider range of concentrations including 100× doses. Thus, the translocation assay described herein is largely devoid of the non-monotonic dose-response effects observed by other detection methods, which makes it suitable for high-throughput screening.

SUMMARY

In conclusion, mammalian cell lines expressing GFP-tagged nuclear receptor constructs were utilized in an automated, highly reproducible, and low cost assay for detection of biologically active glucocorticoids and androgens in water sources. Using this high-throughput screening, combined with studies on transcriptional activation, glucocorticoid and androgen activities were discovered in water sources from 8 of 14 states in the US. This level of wide-spread contamination with steroids of both classes is a possible health hazard not only for the aquatic ecosystems, but may also negatively impact the human population. Largely unrestricted human activity with respect to many potential endocrine disruptors is of concern, and represents one of the main reasons for these wide-spread contaminations. Considering the largely unrestricted human activity in respect to many potential endocrine disruptors and limited methods (Roy & Pereira, *Indian J. Exp. Biol* 43:975-992, 2005) for their detection in the environment, there is an urgent need of better assays for EDC screening. The results discussed here not only highlight the prevalence of contamination of water sources with glucocorticoid and androgen activities, but also introduce a novel approach for monitoring the quality of water. This approach can be readily extended to other nuclear receptors and applied to detection of various classes of EDCs in the environment.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for detecting or quantifying endocrine disruptor chemical (EDC) ligands in an environmental sample, the method comprising:

contacting with the environmental sample:

a first mammalian cell expressing a first traceable fusion protein;

a second mammalian cell expressing a second traceable fusion protein;

a third mammalian cell expressing a third traceable fusion protein;

a fourth mammalian cell expressing a fourth traceable fusion protein; and a fifth mammalian cell expressing a fifth traceable fusion protein, wherein the first, second, third, fourth, and fifth traceable fusion proteins independently comprise either:

(1) a superfamily receptor protein, and a marker protein domain; or (2) the cytoplasmic/nuclear translocation domain of glucocorticoid receptor, the ligand binding domain of a superfamily receptor protein, and a marker protein domain; and detecting cytoplasmic to nuclear translocation of the first, second, third, fourth, and/or fifth fusion proteins in response to one or more ligands of the ligand binding domain in the environmental sample, wherein the first, second, third, fourth, and fifth traceable fusion proteins each bind a different ligand or class of ligands.

2. The method of claim 1, wherein the environmental sample comprises a water sample, soil sample, or air sample.

3. The method of claim 2, wherein the sample comprises a water sample comprising surface water, sub-surface (ground) water, rain, run-off, well water, spring water, drinking water (processed or not), river water, estuary water, ocean water, effluent, treated sewage or untreated sewage.

4. The method of claim 1, wherein detecting the cytoplasmic to nuclear translocation of the first, second, third, fourth, and/or fifth fusion proteins in response to one or more ligands of the ligand binding domain in the environmental sample comprises:

scanning one or more of the mammalian cell(s) to obtain signal data from the marker of the traceable fusion protein;

converting the signal data to obtain the cellular location of the traceable fusion protein in the mammalian cell(s); and analyzing the signal data using an analysis system having an algorithm to calculate changes in distribution of the labeled traceable protein between the cytoplasm and the nucleus of the mammalian cell(s), the analysis system having the capability of providing an accurate reading of the presence in the environmental sample of the ligand(s) which binds to that traceable fusion protein.

5. The method of claim 1, wherein the marker protein domain of each traceable fusion protein is different.

6. The method of claim 1, wherein the marker protein domain is a fluorescent protein domain.

7. The method of claim 1, wherein the first, second, third, fourth and/or fifth mammalian cell is a human cell.

8. The method of claim 1, wherein at least one traceable fusion protein binds a glucocorticoid, at least one traceable fusion protein binds an androgen, at least one traceable fusion protein binds a progestin, at least one traceable fusion protein binds an aryl hydrocarbon, and at least one traceable fusion protein binds a thyroid hormone.

* * * * *